US010780174B2

(12) United States Patent
Ciufolini et al.

(10) Patent No.: US 10,780,174 B2
(45) Date of Patent: Sep. 22, 2020

(54) LIPID-LINKED PRODRUGS

(71) Applicant: The University of British Columbia, Vancouver, BC (CA)

(72) Inventors: Marco A. Ciufolini, Vancouver (CA); Pieter R. Cullis, Vancouver (CA); Yuen Yi Tam, Vancouver (CA); Joshua Zaifman, Vancouver (CA)

(73) Assignee: The University of British Columbia, Vancouver, BC (CA)

( * ) Notice: Subject to any disclaimer, the term of this patent is extended or adjusted under 35 U.S.C. 154(b) by 0 days.

(21) Appl. No.: 16/063,666

(22) PCT Filed: Dec. 22, 2016

(86) PCT No.: PCT/CA2016/000322
§ 371 (c)(1),
(2) Date: Jun. 18, 2018

(87) PCT Pub. No.: WO2017/106957
PCT Pub. Date: Jun. 29, 2017

(65) Prior Publication Data
US 2019/0151458 A1   May 23, 2019

Related U.S. Application Data

(60) Provisional application No. 62/387,160, filed on Dec. 23, 2015.

(51) Int. Cl.
| | | |
|---|---|---|
| *A61K 31/573* | (2006.01) | |
| *A61K 31/337* | (2006.01) | |
| *A61K 31/58* | (2006.01) | |
| *A61K 31/495* | (2006.01) | |
| *A61K 31/519* | (2006.01) | |
| *A61K 31/436* | (2006.01) | |
| *A61K 47/54* | (2017.01) | |
| *C07J 5/00* | (2006.01) | |
| *C07J 41/00* | (2006.01) | |
| *C07D 475/08* | (2006.01) | |
| *C07J 31/00* | (2006.01) | |
| *C07D 305/14* | (2006.01) | |
| *C07J 43/00* | (2006.01) | |
| *C07D 487/04* | (2006.01) | |
| *C07D 295/185* | (2006.01) | |
| *A61P 29/00* | (2006.01) | |
| *A61P 35/00* | (2006.01) | |

(52) U.S. Cl.
CPC .......... *A61K 47/543* (2017.08); *A61K 31/337* (2013.01); *A61K 31/436* (2013.01); *A61K 31/495* (2013.01); *A61K 31/519* (2013.01); *A61K 31/573* (2013.01); *A61K 31/58* (2013.01); *A61P 29/00* (2018.01); *A61P 35/00* (2018.01); *C07D 295/185* (2013.01); *C07D 305/14* (2013.01); *C07D 475/08* (2013.01); *C07D 487/04* (2013.01); *C07J 5/0038* (2013.01); *C07J 5/0076* (2013.01); *C07J 31/006* (2013.01); *C07J 41/005* (2013.01); *C07J 43/003* (2013.01)

(58) Field of Classification Search
CPC .... A61K 31/573; A61K 31/337; A61K 31/58; A61K 31/495; A61K 31/519; A61K 31/436; A61K 47/54; C07J 5/00
See application file for complete search history.

(56) References Cited

U.S. PATENT DOCUMENTS

| 5,952,499 A | 9/1999 | Whittaker et al. |
|---|---|---|
| 6,090,800 A | 7/2000 | Unger et al. |
| 6,444,660 B1 | 9/2002 | Unger et al. |
| 2010/0240883 A1 | 9/2010 | Wu et al. |
| 2013/0245253 A1 | 9/2013 | Marx et al. |
| 2014/0256660 A1 | 9/2014 | Sinha et al. |

FOREIGN PATENT DOCUMENTS

| CN | 104211760 A | 12/2014 |
|---|---|---|
| CN | 104211762 A | 12/2014 |
| WO | 2009070761 | 6/2009 |
| WO | 2011163594 | 12/2011 |
| WO | 2015153345 | 10/2015 |

OTHER PUBLICATIONS

Berezovskaya et al., (2001) "Creating Novel Molecular Transport Systems: The Synthesis and Antiviral Activity of Mixed Succinates of Deoxynucleotides and Hydrophobic Molecules," Pharmaceutical Chemistry Journal, 35(3): 134-138.
Chhikara et al. (2012) "Synthesis Anticancer Activities, and Cellualr Uptake Studies of Lipophilic Derivatives of Doxorubicin Succinate," J. Med Chem. 55: 1500-1510.
Kuznetsova et al., (2012) "Hemocompatibility of liposomes loaded with lipophilic prodrugs of methotrexate and melphalan in the lipid bilayer," Journal of Controlled Release 160: 394-400.
Scriba et al., (1995) "Anticonvulsant Activity of Phenytoin-lipid Conjugates, a New Class of Phenytoin Prodrugs," J. Pharm. Pharmacol., 47: 197-203 XP008064305.
Vodovozova et al., (1996) "Lipid Derivatives of Sarcolysine, Mathotrexate, and Rubomycin," Bioorganicheskaya Khimiya, 22(7): 548-556 XP-002793501 ISSN: 0132-3423.
Vodovozova et al.., (2007) "A Diglyceride Derivative of Methotrexate: Synthesis and Cytotoxic Activity in Addressed Liposomes," Pharmaceutical Chemistry Journal, 41(6) 297-301.

(Continued)

*Primary Examiner* — Brenda L Coleman
(74) *Attorney, Agent, or Firm* — Rudy J. Ng; Bozicevic, Field & Francis LLP

(57) ABSTRACT

This invention provides lipid-linked prodrugs having structures as set out herein. Uses of such lipid-linked prodrug compounds for treatment of various indications, and methods for making and using lipid-linked prodrugs are also provided.

16 Claims, 15 Drawing Sheets

(56) References Cited

OTHER PUBLICATIONS

Wasner et al., (1996) "Synthesis and Characterization pf Monomeric Cordycepin-Vitamin and Cordycepin-Conjugates Lipid Model Substances for Biodegradable Ester and Carbonate Linkages in Conjugates and Potential Inhibitors of HIV-1 Replication," Helvetica Chimica Acta, 79: 609-618 XP-001189644.

LIPID-LINKED PRODRUGS

CROSS REFERENCE TO RELATED APPLICATIONS

This application is a national phase entry under 35 U.S.C. § 371 of International Application No. PCT/CA2016/000322, filed on 22 Dec. 2016, which claims the benefit of U.S. Provisional Patent Application Ser. No. 62/387,160 filed on 23 Dec. 2015, entitled "LIPID-LINKED PRODRUGS", the disclosures of each of which are incorporated herein by reference.

TECHNICAL FIELD

This invention relates to a conjugate of a therapeutic compound and a lipid moiety, compositions thereof, and methods for their use in the delivery of therapeutic compounds. In particular the invention relates to lipid-linked prodrugs, wherein the linker covalently bound to the prodrug is biodegradable. Methods for making and using the conjugates also are provided.

BACKGROUND

Drug selectivity for a target tissue is an important consideration during drug design. Selective delivery of a drug to its target may allow for lower dosages and reduced side effects. Selectivity for a given target tissue may be particularly significant when the therapeutic agents being delivered are chemotherapeutics for the treatment of cancer. In particular, cytotoxic drug therapies are meant to target rapidly dividing cells, but may often be limited by the toxic side effects of the chemotherapeutic on healthy cells. Furthermore, other therapeutic moieties may benefit from selective targeting and improved pharmacokinetic characteristics (i.e. in vivo stability, cellular uptake (for example, lipophilicity), etc.)

Fatty acids have been used to improve selectivity of drugs for their target tissues (for example, U.S. Pat. Nos. 7,235,583; 8,552,054; 6,090,800; US 2012/0264810; US 2013/0330401). Fatty acids previously have been conjugated with drugs to help the drugs as conjugates cross the blood brain barrier (for example, U.S. Pat. No. 4,933,324).

Lipid molecules, including fatty acids or fatty amines, also have been conjugated with drugs to render the conjugates more lipophilic than the unconjugated drugs. Fatty amines are lipid molecules that terminate in an amino group (unlike fatty acids which terminate in a carboxylic acid group). Fatty acids are naturally occurring whereas fatty amines are not a common tissue component in animals.

SUMMARY

This invention is based in part on the fortuitous discovery that conjugates of therapeutic compounds and lipid moieties described herein show improved selective delivery. Furthermore, some of the conjugates of therapeutic compounds and lipid moieties show improved loading, reduced toxicity, improved targeting, improved in vivo potency or improved in vivo stability.

In accordance with one embodiment, there is provided a compound, the compound having the structure of Formula I:

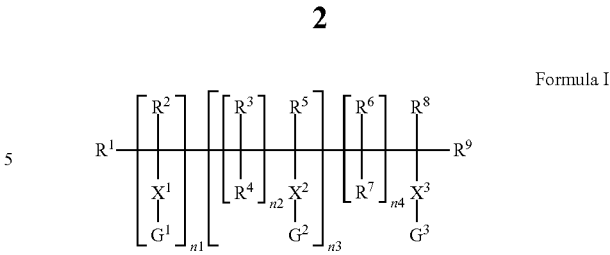

Formula I wherein:
R$^1$ may be H, a linear, branched or cyclic C$_1$-C$_{20}$ alkyl, optionally having one or more cis or trans C=C double bonds of E or Z geometry, wherein the C$_1$-C$_{10}$ alkyl may optionally be substituted with F, Cl, Br, I, OH, C$_1$-C$_6$ O-Alkyl, or C$_1$-C$_6$ O-Acyl, wherein the C$_1$-C$_6$ O-Alkyl or the C$_1$-C$_6$ O-Acyl may optionally be substituted with F, Cl, Br, I or OH;

R$^2$ may be H, a C$_1$-C$_6$ primary amine, C$_1$-C$_6$ secondary amine or a C$_1$-C$_6$ tertiary amine, a linear, branched or cyclic C$_1$-C$_{10}$ alkyl, optionally having one or more cis or trans C=C double bonds of E or Z geometry, wherein the C$_1$-C$_{10}$ alkyl may optionally be substituted with F, Cl, Br, I, OH, C$_1$-C$_6$ O-Alkyl, or C$_1$-C$_6$ O-Acyl, wherein the C$_1$-C$_6$ O-Alkyl or the C$_1$-C$_6$ O-Acyl may optionally be substituted with F, Cl, Br, I or OH;

X$^1$ may be O, S or NR$^{10}$, wherein R$^{10}$ may be H, a linear, branched or cyclic C$_1$-C$_{10}$ alkyl, optionally having one or more cis or trans C=C double bonds of E or Z geometry, wherein the C$_1$-C$_{10}$ alkyl may optionally be substituted with F, Cl, Br, I, OH, C$_1$-C$_6$ O-Alkyl, or C$_1$-C$_6$ O-Acyl, wherein the C$_1$-C$_6$ O-Alkyl or the C$_1$-C$_6$ O-Acyl may optionally be substituted with F, Cl, Br, I or OH;

G$^1$ may be

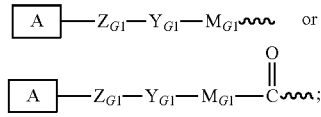

wherein:
A-Z$_{G1}$ may be a drug moiety, wherein Z$_{G1}$ may be an electronegative atom selected from N and O, such that the drug moiety was derived from a drug having the formula A-Z$_{G1}$—H when Z$_{G1}$ has lost an H to covalently bind to Y$_{G1}$;

Y$_{G1}$ may be CH$_2$, O, S, C(=O), PO$_3^{2-}$, or NR$^{11}$ wherein R$^{11}$ may be H, a linear, branched or cyclic C$_1$-C$_{10}$ alkyl, optionally having one or more cis or trans C=C double bonds of E or Z geometry, wherein the C$_1$-C$_{10}$ alkyl may optionally be substituted with F, Cl, Br, I, OH, C$_1$-C$_6$ O-Alkyl, or C$_1$-C$_6$ O-Acyl, and wherein the C$_1$-C$_6$ O-Alkyl or the C$_1$-C$_6$ O-Acyl may optionally be substituted with F, Cl, Br, I or OH;

M$_{G1}$ may be 0-12 atoms selected from C, N, O or S, wherein two or more C atoms optionally have one or more cis or trans C=C double bonds of E or Z geometry and wherein the C atoms may optionally be substituted with F, Cl, Br, I, OH, =O, C$_1$-C$_6$ O-Alkyl, C$_1$-C$_6$ O-Acyl or C$_1$-C$_6$ S-Alkyl;

alternatively, G$^1$ may be H, R$^{13}$ or R$^{13}$—C(=O)—, wherein R$^{13}$ may be C$_9$-C$_{29}$ linear or branched carbon chain, optionally having one or more, cis or trans C=C double bonds and optionally substituted with OH;

alternatively, $G^1$ may be an ionizable moiety selected from: —COOH; —NH$^+$; —OH; —NH$_3^+$; —NH$_2^+$; —SH; —NMe$_2$; —NHMe; and $R^{18}$ wherein $R^{18}$ may be C$_1$-C$_{10}$ alkyl optionally substituted with one or more of COOH, —NH$^+$, —OH, —NH$_3^+$, —NH$_2^+$, —SH, —NMe$_2$, —NHMe;

n1 may be 0, 1, 2, 3, 4 or 5;

$R^3$ may be H, a linear, branched or cyclic C$_1$-C$_{10}$ alkyl, optionally having one or more cis or trans C=C double bonds of E or Z geometry, wherein the C$_1$-C$_{10}$ alkyl may optionally be substituted with F, Cl, Br, I, OH, C$_1$-C$_6$ O-Alkyl, or C$_1$-C$_6$ O-Acyl, wherein the C$_1$-C$_6$ O-Alkyl or the C$_1$-C$_6$ O-Acyl may optionally be substituted with F, Cl, Br, I or OH;

$R^4$ may be H, a linear, branched or cyclic C$_1$-C$_{10}$ alkyl, optionally having one or more cis or trans C=C double bonds of E or Z geometry, wherein the C$_1$-C$_{10}$ alkyl may optionally be substituted with F, Cl, Br, I, OH, C$_1$-C$_6$ O-Alkyl, or C$_1$-C$_6$ O-Acyl, wherein the C$_1$-C$_6$ O-Alkyl or the C$_1$-C$_6$ O-Acyl may optionally be substituted with F, Cl, Br, I or OH;

n2 may be 0, 1, 2, 3, 4 or 5;

$R^5$ may be H, C$_1$-C$_6$ primary amine, C$_1$-C$_6$ secondary amine or C$_1$-C$_6$ tertiary amine, a linear, branched or cyclic C$_1$-C$_{10}$ alkyl, optionally having one or more cis or trans C=C double bonds of E or Z geometry, wherein the C$_1$-C$_{10}$ alkyl may optionally be substituted with F, Cl, Br, I, OH, C$_1$-C$_6$ O-Alkyl, or C$_1$-C$_6$ O-Acyl, wherein the C$_1$-C$_6$ O-Alkyl or the C$_1$-C$_6$ O-Acyl may optionally be substituted with F, Cl, Br, I or OH;

$X^2$ may be O, S or NR$^{14}$, wherein R$^{14}$ may be H, a linear, branched or cyclic C$_1$-C$_{10}$ alkyl, optionally having one or more cis or trans C=C double bonds of E or Z geometry, wherein the C$_1$-C$_{10}$ alkyl may optionally be substituted with F, Cl, Br, I, OH, C$_1$-C$_6$ O-Alkyl, or C$_1$-C$_6$ O-Acyl, wherein the C$_1$-C$_6$ O-Alkyl or the C$_1$-C$_6$ O-Acyl may optionally be substituted with F, Cl, Br, I or OH;

$G^2$ is

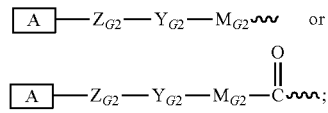

wherein:

A-$Z_{G2}$ may be a drug moiety, wherein $Z_{G2}$ may be an electronegative atom selected from N and O, such that the drug moiety was derived from a drug having the formula A-$Z_{G2}$-H when $Z_{G2}$ has lost an H to covalently bind to $Y_{G2}$;

$Y_{G2}$ may be CH$_2$, O, S, C(=O), PO$_3^{2-}$, or NR$^{11}$ wherein R$^{11}$ may be H, a linear, branched or cyclic C$_1$-C$_{10}$ alkyl, optionally having one or more cis or trans C=C double bonds of E or Z geometry, wherein the C$_1$-C$_{10}$ alkyl may optionally be substituted with F, Cl, Br, I, OH, C$_1$-C$_6$ O-Alkyl, or C$_1$-C$_6$ O-Acyl, and wherein the C$_1$-C$_6$ O-Alkyl or the C$_1$-C$_6$ O-Acyl may optionally be substituted with F, Cl, Br, I or OH;

$M_{G2}$ may be 0-12 atoms selected from C, N, O or S, wherein two or more C atoms optionally have one or more cis or trans C=C double bonds of E or Z geometry and wherein the C atoms may optionally be substituted with F, Cl, Br, I, OH, =O, C$_1$-C$_6$ O-Alkyl, C$_1$-C$_6$ O-Acyl or C$_1$-C$_6$ S-Alkyl;

alternatively, $G^2$ may be H or R$^{16}$—C(=O)—, wherein R$^{16}$ may be a C$_9$-C$_{29}$ linear or branched carbon chain, optionally having one or more, cis or trans C=C double bonds and optionally substituted with OH;

alternatively, $G^2$ may be an ionizable moiety selected from: —COOH; —NH$^+$; —OH; —NH$_3^+$; —NH$_2^+$; —SH; —NMe$_2$; —NHMe; and R$^{18}$ wherein R$^{18}$ may be a C$_1$-C$_{10}$ alkyl optionally substituted with one or more of COOH, —NH$^+$, —OH, —NH$_3^+$, —NH$_2^+$, —SH, —NMe$_2$, —NHMe;

n3 may be 0, 1, 2, 3, 4 or 5;

$R^6$ may be H, a linear, branched or cyclic C$_1$-C$_{10}$ alkyl, optionally having one or more cis or trans C=C double bonds of E or Z geometry, wherein the C$_1$-C$_{10}$ alkyl may optionally be substituted with F, Cl, Br, I, OH, C$_1$-C$_6$ O-Alkyl, or C$_1$-C$_6$ O-Acyl, wherein the C$_1$-C$_6$ O-Alkyl or the C$_1$-C$_6$ O-Acyl may optionally be substituted with F, Cl, Br, I or OH;

$R^7$ may be H, a linear, branched or cyclic C$_1$-C$_{10}$ alkyl, optionally having one or more cis or trans C=C double bonds of E or Z geometry, wherein the C$_1$-C$_{10}$ alkyl may optionally be substituted with F, Cl, Br, I, OH, C$_1$-C$_6$ O-Alkyl, or C$_1$-C$_6$ O-Acyl, wherein the C$_1$-C$_6$ O-Alkyl or the C$_1$-C$_6$ O-Acyl may optionally be substituted with F, Cl, Br, I or OH;

n4 may be 0, 1, 2, 3, 4 or 5;

$R^8$ may be H, C$_1$-C$_6$ primary amine, C$_1$-C$_6$ secondary amine or C$_1$-C$_6$ tertiary amine, linear, branched or cyclic C$_1$-C$_{10}$ alkyl, optionally having one or more cis or trans C=C double bonds of E or Z geometry, wherein the C$_1$-C$_{10}$ alkyl may optionally be substituted with F, Cl, Br, I, OH, C$_1$-C$_6$ O-Alkyl, or C$_1$-C$_6$ O-Acyl, wherein the C$_1$-C$_6$ O-Alkyl or the C$_1$-C$_6$ O-Acyl may optionally be substituted with F, Cl, Br, I or OH;

$X^3$ may be O, S or NR$^{17}$, wherein R$^{17}$ may be H, a linear, branched or cyclic C$_1$-C$_{10}$ alkyl, optionally having one or more cis or trans C=C double bonds of E or Z geometry, wherein the C$_1$-C$_{10}$ alkyl may optionally be substituted with F, Cl, Br, I, OH, C$_1$-C$_6$ O-Alkyl, or C$_1$-C$_6$ O-Acyl, wherein the C$_1$-C$_6$ O-Alkyl or the C$_1$-C$_6$ O-Acyl may optionally be substituted with F, Cl, Br, I or OH;

$G^3$ may be

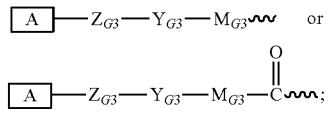

wherein:

A-$Z_{G3}$ may be a drug moiety, wherein $Z_{G3}$ may be an electronegative atom selected from N and O, such that the drug moiety was derived from a drug having the formula A-$Z_{G3}$-H when $Z_{G3}$ has lost an H to covalently bind to $Y_{G3}$;

$Y_{G3}$ may be CH$_2$, O, S, C(=O), PO$_3^{2-}$, or NR$^{11}$ wherein R$^{11}$ may be H, a linear, branched or cyclic C$_1$-C$_{10}$ alkyl, optionally having one or more cis or trans C=C double bonds of E or Z geometry, wherein the C$_1$-C$_{10}$ alkyl may optionally be substituted with F, Cl, Br, I, OH, C$_1$-C$_6$ O-Alkyl, or C$_1$-C$_6$ O-Acyl, and wherein the C$_1$-C$_6$ O-Alkyl or the C$_1$-C$_6$ O-Acyl may optionally be substituted with F, Cl, Br, I or OH;

$M_{G3}$ may be 0-12 atoms selected from C, N, O or S, wherein two or more C atoms optionally have one or more cis or trans C=C double bonds of E or Z geometry and wherein the C atoms may optionally be substituted with F, Cl, Br, I, an OH, =O, $C_1$-$C_6$ O-Alkyl, $C_1$-$C_6$ O-Acyl or $C_1$-$C_6$ S-Alkyl;

alternatively, $G^3$ may be H, $R^{19}$ or $R^{19}$—C(=O)—, wherein $R^{19}$ may be a $C_9$-$C_{29}$ linear or branched carbon chain, optionally having at least one or more, cis or trans C=C double bonds and optionally substituted with OH;

alternatively, $G^3$ may be an ionizable moiety selected from: —COOH; —$NH^+$; —OH; —$NH_3^+$; —$NH_2^+$, —SH; —$NMe_2$; —NHMe; and $R^{18}$ wherein $R^{18}$ may be a $C_1$-$C_{10}$ alkyl optionally substituted with one or more of COOH; —$NH^+$; —OH; —$NH_3^+$; —$NH_2^+$, —SH; —$NMe_2$; —NHMe;

$R^9$ may be H, a $C_1$-$C_6$ primary amine, a $C_1$-$C_6$ secondary amine or a $C_1$-$C_6$ tertiary amine, a linear, branched or cyclic $C_1$-$C_{10}$ alkyl, optionally having one or more cis or trans C=C double bonds of E or Z geometry, wherein the $C_1$-$C_{10}$ alkyl may optionally be substituted with a F, Cl, Br, I, an OH, a $C_1$-$C_6$ O-Alkyl, or a $C_1$-$C_6$ O-Acyl, wherein the $C_1$-$C_6$ O-Alkyl or the $C_1$-$C_6$ O-Acyl may optionally be substituted with a F, Cl, Br, I or OH;

alternatively, wherein n1, n2, n3, n4 may be 0 and $R^1$ may be H, then $R^9$ may be $R^{20}$—C(=O)—, wherein $R^{20}$ may be a $C_7$-$C_{29}$ linear or branched carbon chain, optionally having one or more, cis or trans C=C double bonds and optionally substituted with OH; and provided that at least one of $G^1$, $G^2$ or $G^3$ may be a drug moiety, wherein the drug moiety is selected from

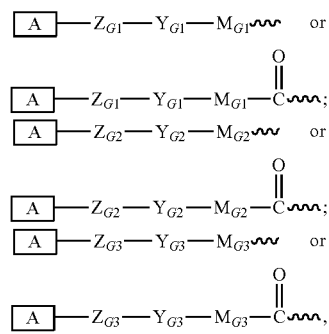

respectively.

In accordance with another embodiment, there is provided a compound, the compound having the structure of Formula I:

Formula I

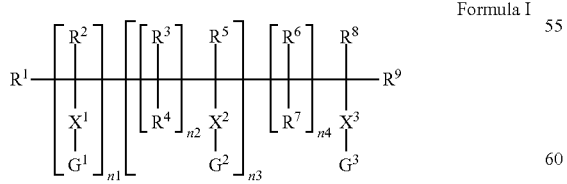

wherein:

$R^1$ may be H or a linear, branched $C_1$-$C_{20}$ alkyl, optionally having one or more cis or trans C=C double bonds of E or Z geometry, wherein the $C_1$-$C_{10}$ alkyl may optionally be substituted with a F, Cl, Br, or I;

$R^2$ may H or a linear, branched $C_1$-$C_{20}$ alkyl, optionally having one or more cis or trans C=C double bonds of E or Z geometry, wherein the $C_1$-$C_{10}$ alkyl is optionally substituted with a F, Cl, Br, or I;

$X^1$ may be O, S or $NR^{10}$, wherein $R^{10}$ may be H, a linear, branched or cyclic $C_1$-$C_6$ alkyl, optionally having one or more cis or trans C=C double bonds of E or Z geometry, wherein the $C_1$-$C_6$ alkyl may optionally be substituted with F, Cl, Br, I, or OH;

$G^1$ may be

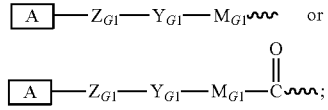

wherein:

A-$Z_{G1}$ may be a drug moiety, wherein $Z_{G1}$ may be an electronegative atom selected from N and O, such that the drug moiety was derived from a drug having the formula A-$Z_{G1}$-H when $Z_{G1}$ has lost an H to covalently bind to $Y_{G1}$;

$Y_{G1}$ may be $CH_2$, O, S, C(=O), $PO_3^{2-}$, or $NR^{11}$ wherein $R^{11}$ may be H, a linear, branched or cyclic $C_1$-$C_{10}$ alkyl, optionally having one or more cis or trans C=C double bonds of E or Z geometry, wherein the $C_1$-$C_{10}$ alkyl may optionally be substituted with F, Cl, Br, I, OH, $C_1$-$C_6$ O-Alkyl, or $C_1$-$C_6$ O-Acyl, and wherein the $C_1$-$C_6$ O-Alkyl or the $C_1$-$C_6$ O-Acyl may optionally be substituted with F, Cl, Br, I or OH;

$M_{G1}$ may be 0-12 atoms selected from C, N, O or S, wherein two or more C atoms optionally have one or more cis or trans C=C double bonds of E or Z geometry and wherein the C atoms may optionally be substituted with F, Cl, Br, I, OH, a =O, $C_1$-$C_6$ O-Alkyl, $C_1$-$C_6$ O-Acyl or $C_1$-$C_6$ S-Alkyl;

alternatively, $G^1$ may be H, $R^{13}$ or $R^{13}$—C(=O)—, wherein $R^{13}$ may be a $C_9$-$C_{29}$ linear or branched carbon chain, having at least one, cis or trans C=C double bond and optionally substituted with OH;

alternatively, $G^1$ may be an ionizable moiety selected from: —COOH; —$NH^+$; —OH; —$NH_3^+$; —$NH^{2+}$; —SH; —$NMe_2$; —NHMe; and $R^{18}$ wherein $R^{18}$ may be a $C_1$-$C_{10}$ alkyl optionally substituted with one or more of COOH, —$NH^+$; —OH, —$NH_3^+$, —$NH_2^+$, —SH, —$NMe_2$, —NHMe;

n1 may be 0, 1 or 2;

$R^3$ may be H, OH, or a linear, branched $C_1$-$C_{10}$ alkyl, optionally having one or more cis or trans C=C double bonds of E or Z geometry, wherein the $C_1$-$C_{10}$ alkyl may optionally be substituted with F, Cl, Br, or I;

$R^4$ may be H, OH, or a linear, branched $C_1$-$C_{10}$ alkyl, optionally having one or more cis or trans C=C double bonds of E or Z geometry, wherein the $C_1$-$C_{10}$ alkyl may optionally be substituted with F, Cl, Br, or I;

n2 may be 0, 1 or 2;

$R^5$ may be H, OH, or a linear, branched $C_1$-$C_{10}$ alkyl, optionally having one or more cis or trans C=C double bonds of E or Z geometry, wherein the $C_1$-$C_{10}$ alkyl may optionally be substituted with F, Cl, Br, or I;

$X^2$ may be O, S or $NR^{10}$, wherein $R^{10}$ may be H, a linear, branched or cyclic $C_1$-$C_6$ alkyl, optionally having one or more cis or trans C=C double bonds of E or Z geometry, wherein the $C_1$-$C_6$ alkyl may optionally be substituted with F, Cl, Br, I, or OH;

$G^2$ may be

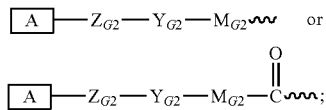

wherein:
- A-$Z_{G2}$ may be a drug moiety, wherein $Z_{G2}$ may be an electronegative atom selected from N and O, such that the drug moiety was derived from a drug having the formula A-$Z_{G2}$-H when $Z_{G2}$ has lost an H to covalently bind to $Y_{G2}$;
- $Y_{G2}$ may be $CH_2$, O, S, C(=O), $PO_3^{2-}$, or $NR^{11}$ wherein $R^{11}$ may be H, a linear, branched or cyclic $C_1$-$C_{10}$ alkyl, optionally having one or more cis or trans C=C double bonds of E or Z geometry, wherein the $C_1$-$C_{10}$ alkyl may optionally be substituted with F, Cl, Br, I, OH, $C_1$-$C_6$ O-Alkyl, or $C_1$-$C_6$ O-Acyl, and wherein the $C_1$-$C_6$ O-Alkyl or the $C_1$-$C_6$ O-Acyl may optionally be substituted with F, Cl, Br, I or OH;
- $M_{G2}$ may be 0-12 atoms selected from C, N, O or S, wherein two or more C atoms optionally have one or more cis or trans C=C double bonds of E or Z geometry and wherein the C atoms may optionally be substituted with F, Cl, Br, I, OH, =O, $C_1$-$C_6$ O-Alkyl, $C_1$-$C_6$ O-Acyl or $C_1$-$C_6$ S-Alkyl;
- alternatively, $G^2$ may be H or $R^{16}$≠C(=O)—, wherein $R^{16}$ may be a $C_9$-$C_{29}$ linear or branched carbon chain, optionally having at least one, cis or trans C=C double bond and optionally substituted with OH;
- alternatively, $G^2$ may be an ionizable moiety selected from: —COOH; —$NH^+$; —OH; —$NH_3^+$; —$NH_2^+$; —SH; —$NMe_2$; —NHMe; and $R^{18}$ wherein $R^{18}$ may be a $C_1$-$C_{10}$ alkyl optionally substituted with one or more of COOH, —$NH^+$, —OH, —$NH_3^+$, —$NH_2^+$, —SH, —$NMe_2$, —NHMe;
- n3 may be 0, 1, or 2;
- $R^6$ may be H, OH, or a linear, branched $C_1$-$C_{10}$ alkyl, optionally having one or more cis or trans C=C double bonds of E or Z geometry, wherein the $C_1$-$C_{10}$ alkyl may optionally be substituted with F, Cl, Br, or I;
- $R^7$ may be H, OH, or a linear, branched $C_1$-$C_{10}$ alkyl, optionally having one or more cis or trans C=C double bonds of E or Z geometry, wherein the $C_1$-$C_{10}$ alkyl may optionally be substituted with F, Cl, Br, or I;
- n4 may be 0, 1, or 2;
- $R^8$ may be H, OH, or a linear, branched $C_1$-$C_{10}$ alkyl, optionally having one or more cis or trans C=C double bonds of E or Z geometry, wherein the $C_1$-$C_{10}$ alkyl may optionally be substituted with F, Cl, Br, or I;
- $X^3$ may be O, S or $NR^{10}$, wherein $R^{10}$ may be H, a linear, branched or cyclic $C_1$-$C_6$ alkyl, optionally having one or more cis or trans C=C double bonds of E or Z geometry, wherein the $C_1$-$C_6$ alkyl may optionally be substituted with F, Cl, Br, I, or OH;
- $G^3$ may be

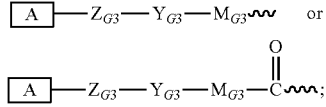

wherein:
- A-$Z_{G3}$ may be a drug moiety, wherein $Z_{G3}$ may be an electronegative atom selected from N and O, such that the drug moiety was derived from a drug having the formula A-$Z_{G3}$-H when $Z_{G3}$ has lost an H to covalently bind to $Y_{G3}$;
- $Y_{G3}$ may be $CH_2$, O, S, C(=O), $PO_3^{2-}$, or $NR^{11}$ wherein $R^{11}$ may be H, a linear, branched or cyclic $C_1$-$C_{10}$ alkyl, optionally having one or more cis or trans C=C double bonds of E or Z geometry, wherein the $C_1$-$C_{10}$ alkyl may optionally be substituted with F, Cl, Br, I, OH, $C_1$-$C_6$ O-Alkyl, or $C_1$-$C_6$ O-Acyl, and wherein the $C_1$-$C_6$ O-Alkyl or the $C_1$-$C_6$ O-Acyl may optionally be substituted with F, Cl, Br, I or OH;
- $M_{G3}$ may be 0-12 atoms selected from C, N, O or S, wherein two or more C atoms optionally have one or more cis or trans C=C double bonds of E or Z geometry and wherein the C atoms may optionally be substituted with F, Cl, Br, I, OH, =O, $C_1$-$C_6$ O-Alkyl, $C_1$-$C_6$ O-Acyl or $C_1$-$C_6$ S-Alkyl;
- alternatively, $G^3$ may be H, $R^{19}$ or $R^{19}$—C(=O)—, wherein $R^{19}$ may be a $C_9$-$C_{29}$ linear or branched carbon chain, optionally having at least one, cis or trans C=C double bond and optionally substituted with OH;
- alternatively, $G^3$ may be an ionizable moiety selected from: —COOH; —$NH^+$; —OH; —$NH_3^+$; —$NH^{2+}$; —SH; —$NMe_2$; —NHMe; and $R^{18}$ wherein $R^{18}$ may be a $C_1$-$C_{10}$ alkyl optionally substituted with one or more of COOH, —$NH^+$, —OH, —$NH_{3+}$, —$NH_2^+$, —SH, —$NMe_2$, —NHMe;
- $R^9$ may be H, $C_1$-$C_6$ primary amine, $C_1$-$C_6$ secondary amine or $C_1$-$C_6$ tertiary amine, linear, branched or cyclic $C_1$-$C_{10}$ alkyl, optionally having one or more cis or trans C=C double bonds of E or Z geometry, wherein the $C_1$-$C_{10}$ alkyl may optionally be substituted with F, Cl, Br, I, OH, $C_1$-$C_6$ O-Alkyl, or $C_1$-$C_6$ O-Acyl, wherein the $C_1$-$C_6$ O-Alkyl or the $C_1$-$C_6$ O-Acyl may optionally be substituted with F, Cl, Br, I or OH;
- alternatively, wherein n1, n2, n3, n4 may be O and $R^1$ may be H, then $R^9$ may be $R^{20}$—C(=O)—, wherein $R^{20}$ may be a $C_7$-$C_{29}$ linear or branched carbon chain, optionally having one or more, cis or trans C=C double bonds and optionally substituted with OH; and
- provided that at least one of $G^1$, $G^2$ or $G^3$ may be drug moiety, wherein the drug moiety is selected from:

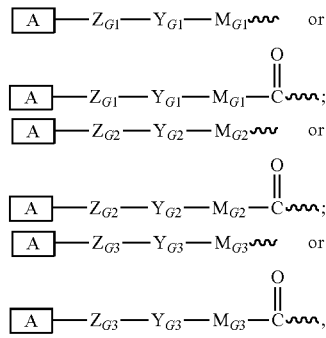

respectively.

In accordance with another embodiment, there is provided a compound, the compound having the structure of Formula III:

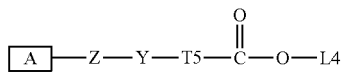

III wherein:
- A-Z may be a drug moiety, wherein Z may be an electronegative atom selected from N or O, such that the drug moiety was derived from a drug having the formula A-Z—H when Z has lost an H to covalently bind to Y;
- Y may be $CH_2$, $C(=O)$, $PO_3^{2-}$ or NH;
- T5 may be 0-6 carbon atoms; and
- L4 may be $C_9$-$C_{29}$ linear or branched carbon chain, optionally having one or more, cis or trans C=C double bonds and optionally substituted with OH or has the Formula V:

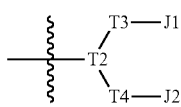

V wherein,
- T2 may be 1-4 carbon atoms;
- T3 may be 0-4 carbon atoms;
- T4 may be 0-4 carbon atoms;
- J1 may be —O—C(=O)-L1;
- J2 may be —O—C(=O)-L2, —COOH, —NH$^+$, —OH, —NH$_3^+$, —NH$_2^+$, —SH, —NMe$_2$, —NHMe, or

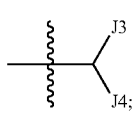

- J3 may be NMe$_2$, —CH$_2$NHMe or H;
- J4 may be —O—C(=O)-L3
- L1 may be $C_9$-$C_{29}$ linear or branched carbon chain, optionally having one or more, cis or trans C=C double bonds and may be optionally substituted with OH;

- L2 may be $C_9$-$C_{29}$ linear or branched carbon chain, optionally having one or more, cis or trans C=C double bonds and may be optionally substituted with OH; and
- L3 may be $C_9$-$C_{29}$ linear or branched carbon chain, optionally having one or more, cis or trans C=C double bonds and may be optionally substituted with OH;

alternatively, Z, Y and T5 may be absent and A may be a drug moiety, having an electronegative atom O preceded by a C(=O), having lost an H to covalently bind to L4. Y may be $CH_2$, $C(=O)$ or $PO_3^{2-}$. Y may be $CH_2$ or $C(=O)$. Y may be $PO_3^{2-}$. Y may be $CH_2$. Y may be $C(=O)$;

provided that when A-Z is a steroid drug then $R^{20}$ is a $C_7$-$C_{29}$ has one or more, cis or trans C=C double bonds;

and provided the compound is not

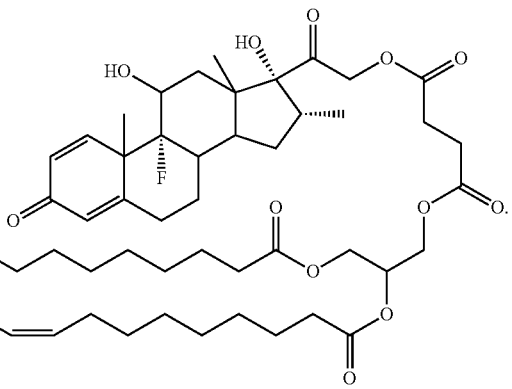

In accordance with another embodiment, there is provided a compound having the structure of Formula II:

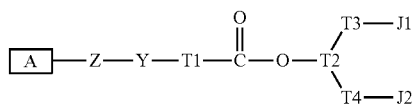

II wherein:
- A-Z may be a drug moiety, wherein Z may be an electronegative atom selected from N or O, such that the drug moiety was derived from a drug having the formula A-Z—H when Z has lost an H to covalently bind to Y;
- Y may be $CH_2$, $C(=O)$, $PO_3^{2-}$, or NH;
- T1 may be 0-6 carbon atoms;
- T2 may be 1-4 carbon atoms;
- T3 may be 0-4 carbon atoms;
- T4 may be 0-4 carbon atoms;
- J1 may be —O—C(=O)-L1;
- J2 may be —O—C(=O)-L2, —COOH, —NH$^+$, —OH, —NH$_3^+$, —NH$_2^+$, —SH, —NMe$_2$, —NHMe, or

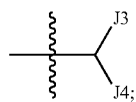

J3 may be NMe$_2$, —CH$_2$NHMe or H;

J4 may be —O—C(=O)-L3

L1 may be C$_9$-C$_{29}$ linear or branched carbon chain, optionally having one or more, cis or trans C=C double bonds and may be optionally substituted with OH;

L2 may be C$_9$-C$_{29}$ linear or branched carbon chain, optionally having one or more, cis or trans C=C double bonds and may be optionally substituted with OH; and L3 may be C$_9$-C$_{29}$ linear or branched carbon chain, optionally having one or more, cis or trans C=C double bonds and may be optionally substituted with OH;

provided that when A-Z is a steroid drug then R$^{20}$ is a C$_7$-C$_{29}$ has one or more, cis or trans C=C double bonds;

and provided the compound is not

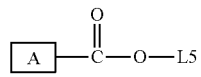

wherein:

A may be a drug moiety, having an electronegative atom O preceded by a C(=O), and having lost an H to covalently bind to L5; and L5 may be C$_9$-C$_{29}$ linear or branched carbon chain, optionally having one or more, cis or trans C=C double bonds and may be optionally substituted with OH.

T5 may be 0-5 carbon atoms. T5 may be 0-4 carbon atoms. T5 may be 0-3 carbon atoms.

T5 may be 0-2 carbon atoms. T5 may be 0-1 carbon atoms. T5 may be 0 carbon atoms. T5 may be 1-6 carbon atoms. T5 may be 1-5 carbon atoms. T5 may be 1-4 carbon atoms. T5 may be 1-3 carbon atoms. T5 may be 1-2 carbon atoms. T5 may be 2 carbon atoms. T5 may be 1 carbon atom. T5 may be 3 carbon atoms.

L4 may be C$_9$-C$_{29}$ linear or branched carbon chain, optionally having one or more, cis or trans C=C double

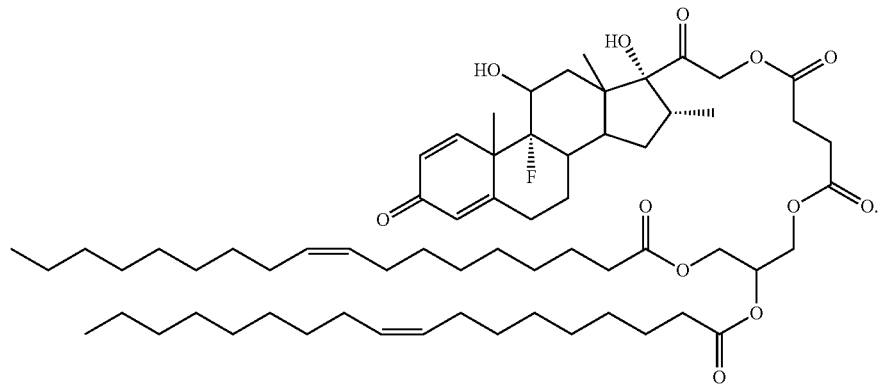

In accordance with another embodiment, there is provided a compound having the structure of Formula III:

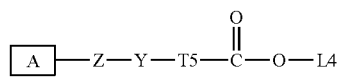

wherein:

A-Z may be a drug moiety, wherein Z may be an electronegative atom selected from N or O, such that the drug moiety was derived from a drug having the formula A-Z—H when Z has lost an H to covalently bind to Y;

Y may be CH$_2$, C(=O), PO$_3^{2-}$, or NH;

T5 may be 0-6 carbon atoms; and

L4 may be C$_9$-C$_{29}$ linear or branched carbon chain, optionally having one or more, cis or trans C=C double bonds and optionally substituted with OH.

In accordance with another embodiment, there is provided a compound having the structure of Formula N:

bonds and optionally substituted with OH. L4 may be C$_9$-C$_{29}$ linear or branched carbon chain, optionally having one or more, cis or trans C=C double bonds. L4 may be C$_9$-C$_{25}$ linear or branched carbon chain, optionally having one or more, cis or trans C=C double bonds and optionally substituted with OH. L4 may be C$_9$-C$_{22}$ linear or branched carbon chain, optionally having one or more, cis or trans C=C double bonds and optionally substituted with OH. L4 may be C$_9$-C$_{20}$ linear or branched carbon chain, optionally having one or more, cis or trans C=C double bonds and optionally substituted with OH. L4 may be C$_9$-C$_{18}$ linear or branched carbon chain, optionally having one or more, cis or trans C=C double bonds and optionally substituted with OH. L4 may be C$_9$-C$_{16}$ linear or branched carbon chain, optionally having one or more, cis or trans C=C double bonds and optionally substituted with OH.

L4 may have the Formula V:

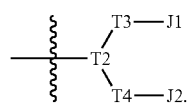

T2 may be 1-4 carbon atoms. T2 may be 1-3 carbon atoms. T2 may be 1-2 carbon atoms. T2 may be 2-4 carbon atoms. T2 may be 3-4 carbon atoms. T2 may be 1 carbon atom. T2 may be 2 carbon atoms. T2 may be 3 carbon atoms. T3 may be 0-4 carbon atoms. T3 may be 0-3 carbon atoms. T3 may be 0-2 carbon atoms. T3 may be 0-1 carbon atoms. T3 may be 1-4 carbon atoms. T3 may be 1-3 carbon atoms. T3 may be 1-2 carbon atoms. T3 may be 2 carbon atoms. T3 may be 3 carbon atoms. T3 may be 4 carbon atoms. T4 may be 0-4 carbon atoms. T4 may be 0-3 carbon atoms. T4 may be 0-2 carbon atoms. T4 may be 0-1 carbon atoms. T4 may be 1-4 carbon atoms. T4 may be 1-3 carbon atoms. T4 may be 1-2 carbon atoms. T4 may be 2 carbon atoms. T4 may be 3 carbon atoms. T4 may be 4 carbon atoms. J1 may be —O—C(=O)-L1. J2 may be —O—C(=O)-L2, —COOH, —NH$^+$, —OH, —NH$_3^+$, —NH$_2^+$, —SH, —NMe$_2$, —NHMe, or

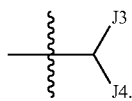

J2 may be —O—C(=O)-L2, —COOH, —NH$^+$, —OH, —NH$_3^+$, —NH$_2^+$, —SH, —NMe$_2$, or —NHMe. J2 may be —O—C(=O)-L2, —COOH, —NH$^+$, —OH, —NH$_3^+$, —NH$_2^+$, —SH, or —NMe$_2$. J2 may be

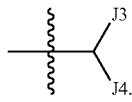

J2 may be —O—C(=O)-L2, —COOH, —NH$^+$, —OH, —NH$_3^+$ or —NH$_2^+$. J2 may be O—C(=O)-L2. J2 may be —O—C(=O)-L2, —COOH, —NH$^+$, or —OH. J2 may be —COOH, —NH$^+$ or —OH. J3 may be NMe$_2$, —CH$_2$NHMe or H. J3 may be —CH$_2$NHMe. J3 may be H. J3 may be NMe$_2$. J4 may be —O—C(=O)-L3.

L1 may be $C_9$-$C_{29}$ linear or branched carbon chain, optionally having one or more, cis or trans C=C double bonds. L2 may be $C_9$-$C_{29}$ linear or branched carbon chain, optionally having one or more, cis or trans C=C double bonds. L3 may be $C_9$-$C_{29}$ linear or branched carbon chain, optionally having one or more, cis or trans C=C double bonds.

T1 may be 0-5 carbon atoms. T1 may be 0-4 carbon atoms. T1 may be 0-3 carbon atoms. T1 may be 0-2 carbon atoms. T1 may be 0-1 carbon atoms. T1 may be 0 carbon atoms. T1 may be 1-6 carbon atoms. T1 may be 1-5 carbon atoms. T1 may be 1-4 carbon atoms. T1 may be 1-3 carbon atoms. T1 may be 1-2 carbon atoms. T1 may be 2 carbon atoms. T1 may be 1 carbon atom. T1 may be 3 carbon atoms. L5 may be $C_9$-$C_{29}$ linear or branched carbon chain, optionally having one or more, cis or trans C=C double bonds. L5 may be $C_9$-$C_{29}$ linear or branched carbon chain, optionally having one or more, cis or trans C=C double bonds and optionally substituted with OH. L5 may be $C_9$-$C_{29}$ linear or branched carbon chain, optionally having one or more, cis or trans C=C double bonds. L5 may be $C_9$-$C_{25}$ linear or branched carbon chain, optionally having one or more, cis or trans C=C double bonds and optionally substituted with OH. L5 may be $C_9$-$C_{22}$ linear or branched carbon chain, optionally having one or more, cis or trans C=C double bonds and optionally substituted with OH. L5 may be $C_9$-$C_{20}$ linear or branched carbon chain, optionally having one or more, cis or trans C=C double bonds and optionally substituted with OH. L5 may be $C_9$-$C_{18}$ linear or branched carbon chain, optionally having one or more, cis or trans C=C double bonds and optionally substituted with OH. L5 may be $C_9$-$C_{16}$ linear or branched carbon chain, optionally having one or more, cis or trans C=C double bonds and optionally substituted with OH.

Alternatively, Z, Y and T5 may be absent and A may be a drug moiety, having an electronegative atom O preceded by a C(=O), having lost an H to covalently bind to L4. A may be selected from one or more of Tacrolimus, Dexamethasone, SN-38, Docetaxel, Methotrexate, NPC$_1$I, Amprenavir, Amphotericin B, Bexarotene, Calcitrol, Cyclosporin A, Digoxin, Doxercalciferol, Dronabinol, Etoposide, Fulvestrant, Paricalcitol, Teniposide, Isotretinoin, Sirolimus, Tretinoin, Valproic acid, Paclitaxel, Valrubicin, Propofol, Prednisone, Prednisolone, Mycophenolic acid, Lovastatin, Lamivudine, Zidovudine, Abacavir, Emitricitabine, Atazanavir, Cobicistat, Elvitegravir, Isonazid, Albendazole, Lisinapril, Amlodipine, Isotretinoin, Baclofen, Benznidazole, Nifurtimox, Mefloquine, Sulfadoxine, Pyrimethamine, Chlorproguanil, 6-Mercaptopurine, 1-Thyroxine, Glyburide, MCC950, Parthenolide, Tauroursodeoxycholic acid Ruxolitinib and Tofacitinib.

Alternatively, A may be selected from one or more of Docetaxel, Methotrexate, SN-38, NPC$_1$I, Amprenavir, Amphotericin B, Bexarotene, Calcitrol, Cyclosporin A, Digoxin, Doxercalciferol, Dronabinol, Etoposide, Fulvestrant, Paricalcitol, Teniposide, Isotretinoin, Tretinoin, Valproic acid, Paclitaxel, Valrubicin, Propofol, Mycophenolic acid, Lovastatin, Lamivudine, Zidovudine, Abacavir, Emitricitabine, Atazanavir, Cobicistat, Elvitegravir, Isonazid, Albendazole, Lisinapril, Amlodipine, Isotretinoin, Baclofen, Benznidazole, Nifurtimox, Mefloquine, Sulfadoxine, Pyrimethamine, Chlorproguanil, 6-Mercaptopurine, 1-Thyroxine, Glyburide, MCC950, Parthenolide, Tauroursodeoxycholic acid, Ruxolitinib, Tofacitinib, Cyclosporine, Tacrolimus, Everolimus, Sirolimus, Azathioprine, Leflunomide, Mycophenolate, Dexamethasone, Budesonide, Prednisone, Prednisolone, Methylprednisolone, Hydrocortisone, Cortisone, Fludrocortisone, Betamethasone, Triamcinolone, Triamcinolone acetonide, Flunisolide, Beclamethasone, Fluticasone, Mometasone, Flumethasone, Isoflupredone, Corticosterone, Desoxycortone acetate, Desoxycortone enanthate, n-Deoxycorticosterone, 11-Deoxycortisol, and Aldosterone.

Alternatively, A may be selected from one or more of Docetaxel, Methotrexate, SN-38, NPC$_1$I, Amprenavir, Amphotericin B, Bexarotene, Calcitrol, Cyclosporin A, Digoxin, Doxercalciferol, Dronabinol, Etoposide, Fulvestrant, Paricalcitol, Teniposide, Isotretinoin, Tretinoin, Valproic acid, Paclitaxel, Valrubicin, Propofol, Mycophenolic acid, Lovastatin, Lamivudine, Zidovudine, Abacavir, Emitricitabine, Atazanavir, Cobicistat, Elvitegravir, Isonazid, Albendazole, Lisinapril, Amlodipine, Isotretinoin, Baclofen, Benznidazole, Nifurtimox, Mefloquine, Sulfadoxine, Pyrimethamine, Chlorproguanil, 6-Mercaptopurine, 1-Thyroxine, Glyburide, MCC950, Parthenolide, Tauroursodeoxycholic acid, Ruxolitinib, Tofacitinib, Cyclosporine, Tacrolimus, Everolimus, Sirolimus, Azathioprine, Leflunomide and Mycophenolate.

Alternatively, A may be selected from one or more of Docetaxel, Methotrexate, SN-38, NPC$_1$I, Amprenavir, Amphotericin B, Bexarotene, Calcitrol, Cyclosporin A, Digoxin, Doxercalciferol, Dronabinol, Etoposide, Fulvestrant, Paricalcitol, Teniposide, Isotretinoin, Tretinoin, Valproic acid, Paclitaxel, Valrubicin, Propofol, Mycophenolic acid, Lovastatin, Lamivudine, Zidovudine, Abacavir, Emitricitabine, Atazanavir, Cobicistat, Elvitegravir, Isonazid, Albendazole, Lisinapril, Amlodipine, Isotretinoin, Baclofen, Benznidazole, Nifurtimox, Mefloquine, Sulfadoxine, Pyrimethamine, Chlorproguanil, 6-Mercaptopurine, 1-Thyroxine, Glyburide, MCC950, Parthenolide, Tauroursodeoxycholic acid, Ruxolitinib and Tofacitinib.

Alternatively, A may be selected from one or more of Docetaxel, Methotrexate, SN-38, $NPC_1I$, Amprenavir, Amphotericin B, Bexarotene, Calcitrol, Cyclosporin A, Digoxin, Doxercalciferol, Dronabinol, Etoposide, Fulvestrant, Paricalcitol, Teniposide, Isotretinoin, Tretinoin, Valproic acid, Paclitaxel, Valrubicin, Propofol, Mycophenolic acid, Lovastatin, Lamivudine, Zidovudine, Abacavir, Emitricitabine, Atazanavir, Cobicistat, Elvitegravir, Isonazid, Albendazole, Lisinapril, Amlodipine, Isotretinoin, Baclofen, Benznidazole, Nifurtimox, Mefloquine, Sulfadoxine, Pyrimethamine, Chlorproguanil, 6-Mercaptopurine, 1-Thyroxine, Glyburide, MCC950, Parthenolide, Tauroursodeoxycholic acid, Ruxolitinib, Tofacitinib, Dexamethasone, Budesonide, Prednisone, Prednisolone, Methylprednisolone, Hydrocortisone, Cortisone, Fludrocortisone, Betamethasone, Triamcinolone, Triamcinolone acetonide, Flunisolide, Beclamethasone, Fluticasone, Mometasone, Flumethasone, Isoflupredone, Corticosterone, Desoxycortone acetate, Desoxycortone enanthate, n-Deoxycorticosterone, 11-Deoxycortisol, and Aldosterone. Alternatively, A may be selected from one or more of Cyclosporine, Tacrolimus, Everolimus, Sirolimus, Azathioprine, Leflunomide, Mycophenolate, Dexamethasone, Budesonide, Prednisone, Prednisolone, Methylprednisolone, Hydrocortisone, Cortisone, Fludrocortisone, Betamethasone, Triamcinolone, Triamcinolone acetonide, Flunisolide, Beclamethasone, Fluticasone, Mometasone, Flumethasone, Isoflupredone, Corticosterone, Desoxycortone acetate, Desoxycortone enanthate, n-Deoxycorticosterone, u-Deoxycortisol, and Aldosterone.

Alternative drugs may be incorporated based on the methods set out herein.

$Y_{G1}$, $Y_{G2}$ or $Y_{G3}$ may be independently selected from $CH_2$, O, S, C(=O), $PO_3^{2-}$, or $NR^{11}$ wherein $R^{11}$ may be H, a linear, branched or cyclic $C_1$-$C_8$ alkyl, may optionally have one or more cis or trans C=C double bonds of E or Z geometry, wherein the $C_1$-$C_8$ alkyl may optionally be substituted with F, Cl, Br, I, OH, $C_1$-$C_6$ O-Alkyl, or $C_1$-$C_6$ O-Acyl, and wherein the $C_1$-$C_6$ O-Alkyl or the $C_1$-$C_6$ O-Acyl may optionally be substituted with F, Cl, Br, I or OH.

Y may be $CH_2$, O, S, C(=O), $PO_3^{2-}$, or $NR^{11}$ wherein $R^{11}$ may be H, a linear, branched or cyclic $C_1$-$C_6$ alkyl, optionally having one or more cis or trans C=C double bonds of E or Z geometry, wherein the $C_1$-$C_6$ alkyl may optionally be substituted with F, Cl, Br, I or OH.

$Y_{G1}$, $Y_{G2}$ or $Y_{G3}$ may be independently selected from $CH_2$, O, S, C(=O), $PO_3^{2-}$, or NH. $Y_{G1}$, $Y_{G2}$ or $Y_{G3}$ may be independently selected from may be $CH_2$, O, S, C(=O), or NH. $Y_{G1}$, $Y_{G2}$ or $Y_{G3}$ may be independently selected from $CH_2$, C(=O) or $PO_3^{2-}$.

M may be 0-10 atoms selected from C, N, O or S, wherein two or more C atoms may optionally have one or more cis or trans C=C double bonds of E or Z geometry and wherein the C or N atoms may optionally be substituted with F, Cl, Br, I, OH, =O, $C_1$-$C_6$ O-Alkyl, $C_1$-$C_6$ O-Acyl or $C_1$-$C_6$ S-Alkyl. M may be 0-8 atoms selected from C, N, O or S, wherein two or more C atoms may optionally have one or more cis or trans C=C double bonds of E or Z geometry and wherein the C or N atoms may optionally be substituted with F, Cl, Br, I, OH, =O, $C_1$-$C_6$ O-Alkyl, $C_1$-$C_6$ O-Acyl or $C_1$-$C_6$ S-Alkyl. M may be 0-8 atoms selected from C, N, O or S, wherein two or more C atoms optionally may have one or more cis or trans C=C double bonds of E or Z geometry, wherein the C or N atoms may optionally be substituted with F, Cl, Br, or I. M may be 0-6 atoms selected from C, N, O or S, wherein two or more C atoms optionally have one or more cis or trans C=C double bonds of E or Z geometry, wherein the C or N atoms may optionally be substituted with F, Cl, Br, or I. M may be 0-5 atoms selected from C, N, O or S, wherein two or more C atoms may optionally have one or more cis or trans C=C double bonds of E or Z geometry, wherein the C or N atoms may optionally be substituted with F, Cl, Br, or I. M may be 0-5 atoms selected from C, N, O or S, wherein the C or N atoms may optionally be substituted with F, Cl, Br, or I.

$G^1$ may be H, $R^{13}$ or $R^{13}$—C(=O), wherein $R^{13}$ may be a $C_9$-$C_{29}$ linear or branched carbon chain, may have at least one, cis or trans C=C double bond. $G^1$ may be H, $R^{13}$ or $R^{13}$—C(=O)—. $G^1$ may be H or $R^{13}$. $G^1$ may be H or $R^{13}$—C(=O). $G^1$ may be H. $G^1$ may be $R^{13}$—C(=O)—. $G^1$ may be $R^{13}$. $G^1$ may be an ionizable moiety selected from: —COOH; —$NH^+$; —OH; —$NH_3^+$; —$NH_2^+$; —SH; —$NMe_2$; and —NHMe. $R^{13}$ may be a $C_9$-$C_{29}$ linear or branched carbon chain, may have at least one, cis or trans C=C double bond.

$G^2$ may be H or $R^{16}$—C(=O)—, wherein $R^{16}$ is a $C_9$-$C_{29}$ linear or branched carbon chain, optionally having at least one, cis or trans C=C double bond. $G^2$ may be an ionizable moiety selected from: —COOH; —$NH^+$; —OH; —$NH_3^+$; —$NH_2^+$; —SH; —$NMe_2$; and —NHMe.

$G^3$ may be H, $R^{19}$ or $R^{19}$—C(=O)—, wherein $R^{19}$ may be a $C_9$-$C_{29}$ linear or branched carbon chain, optionally having at least one, cis or trans C=C double bond. $G^3$ may be H, $R^{19}$ or $R^{19}$—C(=O)—. $G^3$ may be H or $R^{19}$. $G^3$ may be H or $R^{19}$—C(=O)—. $G^3$ may be H. $G^3$ may be $R^{19}$ or $R^{19}$—C(=O)—. $G^3$ may be $R^{19}$. $G^3$ may be $R^{19}$—C(=O)—. $R^{19}$ may be a $C_9$-$C_{29}$ linear or branched carbon chain, optionally having at least one, cis or trans C=C double bond. $G^3$ may be an ionizable moiety selected from: —COOH; —$NH^+$; —OH; —$NH_3^+$; —$NH_2^+$; —SH; —$NMe_2$; and —NHMe.

$R^1$ may be H, OH, or a linear, branched $C_1$-$C_8$ alkyl, optionally having one or more cis or trans C=C double bonds of E or Z geometry, wherein the $C_1$-$C_8$ alkyl may be optionally substituted with a F, Cl, Br or I. $R^1$ may be H, OH, or a linear, branched $C_1$-$C_8$ alkyl, wherein the $C_1$-$C_8$ alkyl may be optionally substituted with a F, Cl, Br or I. $R^1$ may be H, OH, or a linear, branched $C_1$-$C_8$ alkyl, may optionally have one or more cis or trans C=C double bonds of E or Z geometry. Alternatively, $R^1$ may be H, OH, or a linear, branched $C_1$-$C_{10}$ alkyl, optionally having one or more cis or trans C=C double bonds of E or Z geometry, wherein the $C_1$-$C_{10}$ alkyl may optionally be substituted with a F, Cl, Br, or I. Alternatively, $R^1$ may be H, OH, or a linear, branched $C_1$-$C_{10}$ alkyl, optionally having one or more cis or trans C=C double bonds of E or Z geometry. Alternatively, $R^1$ may be H, OH, or a linear, branched $C_1$-$C_5$ alkyl, optionally having one or more cis or trans C=C double bonds of E or Z geometry, wherein the $C_1$-$C_{10}$ alkyl may optionally be substituted with a F, Cl, Br, or I. $R^2$ may be OH.

$X^1$ may be O, S or $NR^{10}$, wherein $R^{10}$ may be H, a linear, branched or cyclic $C_1$-$C_6$ alkyl, and may optionally have one or more cis or trans C=C double bonds of E or Z geometry. $X^1$ may be O, S or $NR^{10}$, wherein $R^{10}$ may be H, a linear, branched or cyclic $C_1$-$C_6$ alkyl, wherein the $C_1$-$C_6$ alkyl may optionally be substituted with F, Cl, Br, I, or OH. $X^1$ may be O or S.

n1 may be 1 or 2. n1 may be 0.

$R^3$ may be H, OH, or a linear, branched $C_1$-$C_{10}$ alkyl, optionally may have one or more cis or trans C=C double bonds of E or Z geometry. $R^3$ may be H, OH, or a linear, branched $C_1$-$C_{10}$ alkyl, wherein the $C_1$-$C_{10}$ alkyl may optionally be substituted with F, Cl, Br, or I. $R^3$ may be H or OH.

$R^4$ may be H, OH, or a linear, branched alkyl, wherein the $C_1$-$C_{10}$ alkyl may optionally be substituted with F, Cl, Br, or I. $R^4$ may be H, OH, or a linear, branched $C_1$-$C_{10}$ alkyl, and may optionally have one or more cis or trans C=C double bonds of E or Z geometry. $R^4$ may be H or OH.

n2 may be 1 or 2. n2 may be 0.

$R^5$ may be H, OH, or a linear, branched $C_1$-$C_{10}$ alkyl, and may optionally have one or more cis or trans C=C double bonds of E or Z geometry. $R^5$ may be H, OH, or a linear, branched $C_1$-$C_{10}$ alkyl, wherein the $C_1$-$C_{10}$ alkyl may optionally be substituted with F, Cl, Br, or I. $R^5$ may be H or OH.

$X^2$ may be O, S or $NR^{10}$, wherein $R^{10}$ may be H, a linear, wherein the $C_1$-$C_6$ alkyl may optionally be substituted with F, Cl, Br, I, or OH. $X^2$ may be O, S or $NR^{10}$, wherein $R^{10}$ may be H, a linear, branched or cyclic $C_1$-$C_6$ alkyl, may optionally have one or more cis or trans C=C double bonds of E or Z geometry. $X^2$ may be O or S.

n3 may be 1, or 2. n3 may be 0.

$R^6$ may be H, OH, or a linear, branched $C_1$-$C_{10}$ alkyl, wherein the $C_1$-$C_{10}$ alkyl may optionally be substituted with F, Cl, Br, or I. $R^6$ may be H, OH, or a linear, branched $C_1$-$C_{10}$ alkyl, and may optionally have one or more cis or trans C=C double bonds of E or Z geometry. $R^6$ may be H or OH.

$R^7$ may be H, OH, or a linear, branched $C_1$-$C_{10}$ alkyl, wherein the $C_1$-$C_{10}$ alkyl may optionally be substituted with F, Cl, Br, or I. $R^7$ may be H, OH, or a linear, branched $C_1$-$C_{10}$ alkyl, and may optionally have one or more cis or trans C=C double bonds of E or Z geometry. $R^7$ may be H or OH.

n4 may be 1, or 2. n4 may be 0.

$R^8$ may be H, OH, or a linear, branched $C_1$-$C_{10}$ alkyl, wherein the $C_1$-$C_{10}$ alkyl may optionally be substituted with F, Cl, Br, or I. $R^8$ may be H, OH, or a linear, branched $C_1$-$C_{10}$ alkyl, and may optionally have one or more cis or trans C=C double bonds of E or Z geometry. $R^8$ may be H or OH.

$X^3$ may be O, S or $NR^{10}$, wherein $R^{10}$ may be H, a linear, branched or cyclic $C_1$-$C_6$ alkyl, wherein the $C_1$-$C_6$ alkyl may optionally be substituted with F, Cl, Br, I, or OH. $X^3$ may be O, S or $NR^{10}$, wherein $R^{10}$ is H, a linear, branched or cyclic $C_1$-$C_6$ alkyl, and may optionally have one or more cis or trans C=C double bonds of E or Z geometry. $X^3$ may O or S.

$R^9$ may be $R^{20}$—C(=O)—, wherein $R^{20}$ may be a $C_9$-$C_{29}$ linear or branched carbon chain, optionally having one or more, cis or trans C=C double bonds and optionally substituted with OH. $R^9$ may be $R^{20}$—C(=O)—, wherein $R^{20}$ may be a $C_8$-$C_{29}$ linear or branched carbon chain, optionally having one or more, cis or trans C=C double bonds and optionally substituted with OH. $R^9$ may be $R^{20}$—C(=O)—, wherein $R^{20}$ may be a $C_7$-$C_{29}$ linear or branched carbon chain, optionally having one or more, cis or trans C=C double bonds and optionally substituted with OH. $R^9$ may be $R^{20}$—C(=O)—, wherein $R^{20}$ may be a $C_6$-$C_{29}$ linear or branched carbon chain, optionally having one or more, cis or trans C=C double bonds and optionally substituted with OH. $R^9$ may be $R^{20}$—C(=O), wherein $R^{20}$ may be a $C_5$-$C_{29}$ linear or branched carbon chain, optionally having one or more, cis or trans C=C double bonds and optionally substituted with OH. $R^9$ may be H, $C_1$-$C_6$ primary amine, $C_1$-$C_6$ secondary amine or $C_1$-$C_6$ tertiary amine, linear, branched or cyclic $C_1$-$C_{10}$ alkyl, wherein the $C_1$-$C_{10}$ alkyl may optionally be substituted with F, Cl, Br, I, OH, $C_1$-$C_6$ O-Alkyl, or $C_1$-$C_6$ O-Acyl, wherein the $C_1$-$C_6$ O-Alkyl or the $C_1$-$C_6$ O-Acyl may optionally be substituted with F, Cl, Br, I or OH. $R^9$ may be H, $C_1$-$C_6$ primary amine, $C_1$-$C_6$ secondary amine or $C_1$-$C_6$ tertiary amine, linear, branched or cyclic $C_1$-$C_{10}$ alkyl, and may optionally have one or more cis or trans C=C double bonds of E or Z geometry, wherein the $C_1$-$C_{10}$ alkyl may optionally be substituted with F, Cl, Br, I, OH, $C_1$-$C_6$ O-Alkyl, or $C_1$-$C_6$ O-Acyl, wherein the $C_1$-$C_6$ O-Alkyl or the $C_1$-$C_6$ O-Acyl. $R^9$ may be H.

The compound may be selected from one or more of the following:

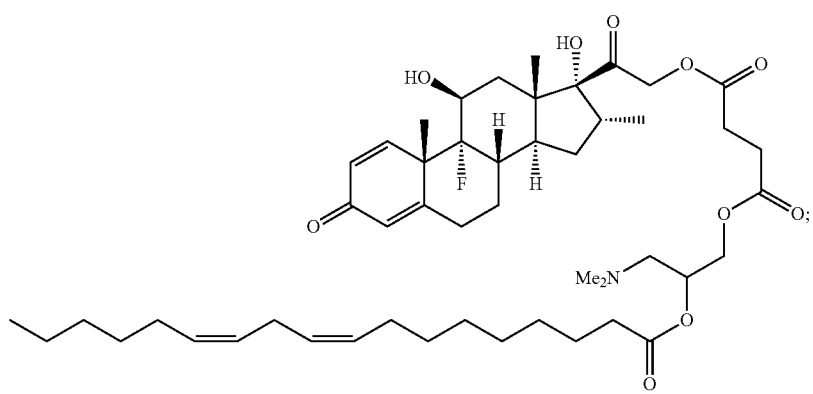

-continued
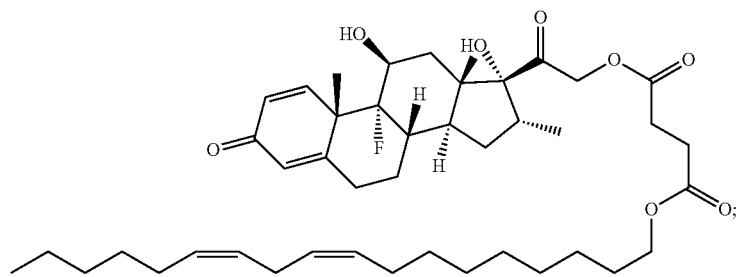
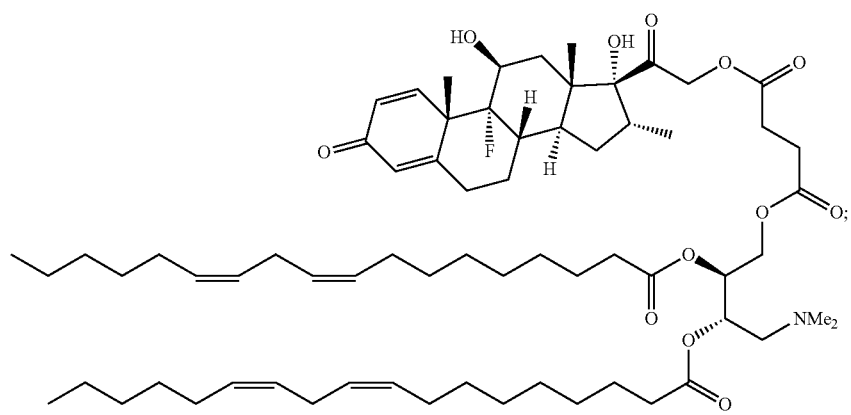
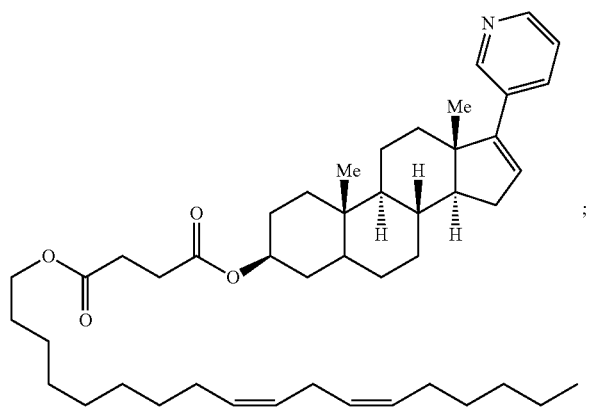
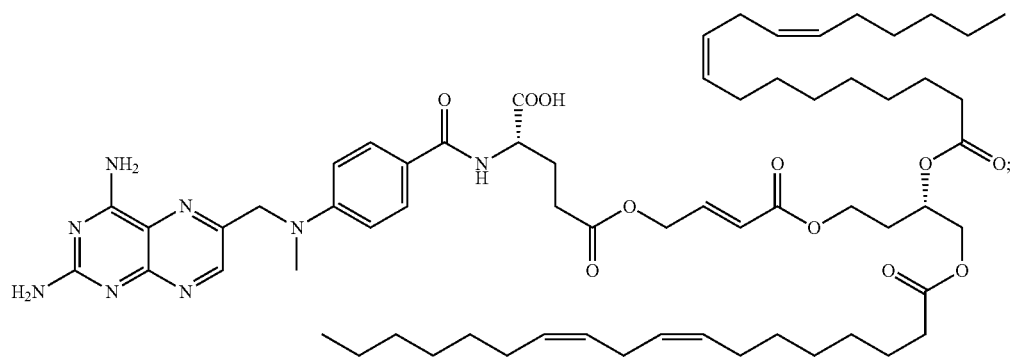

-continued
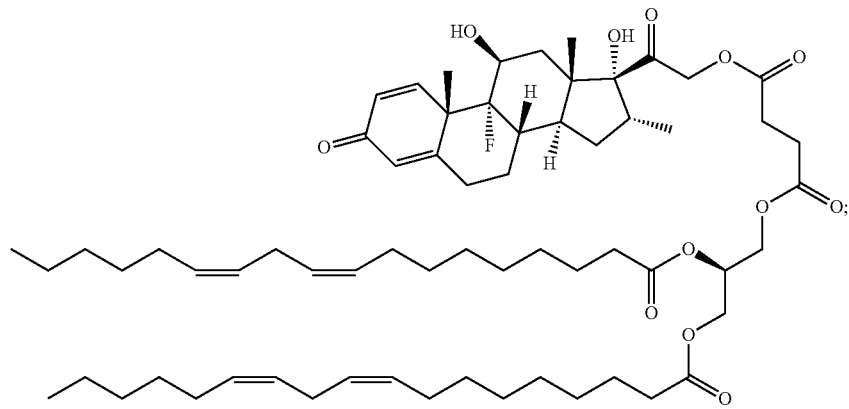
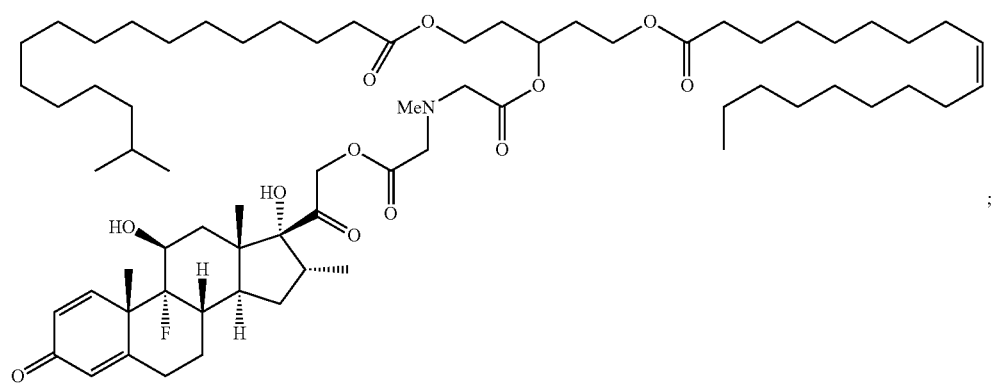
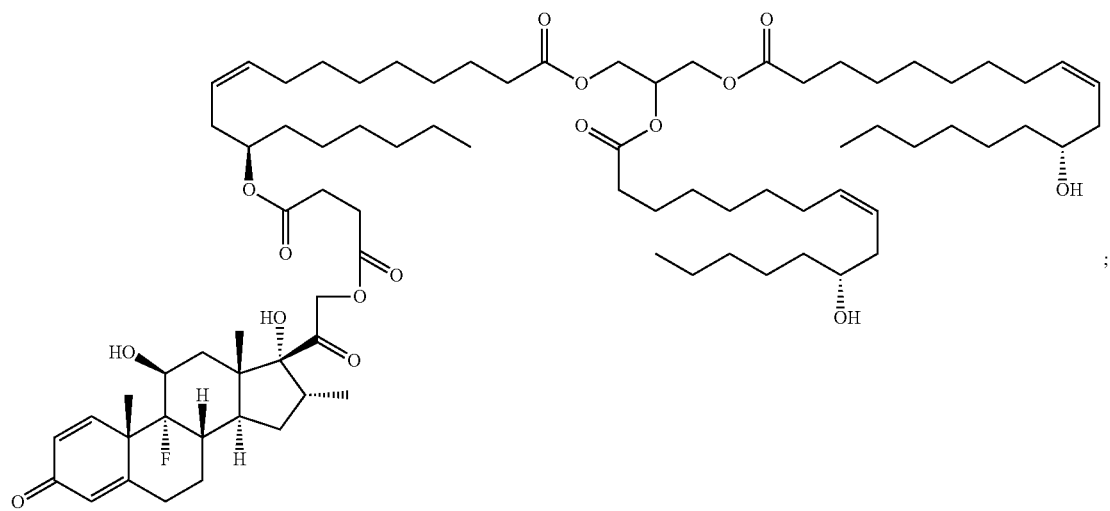

-continued
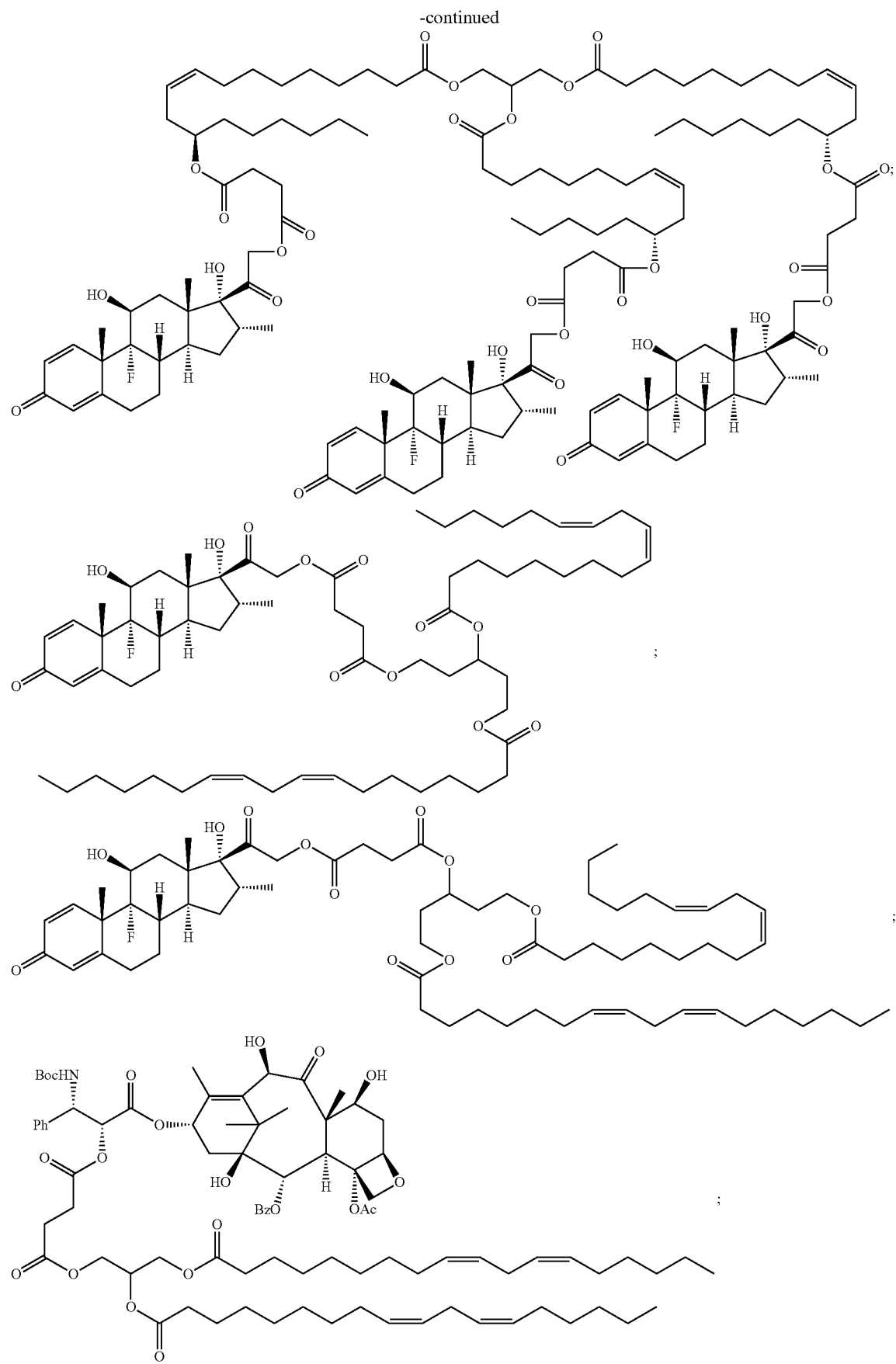

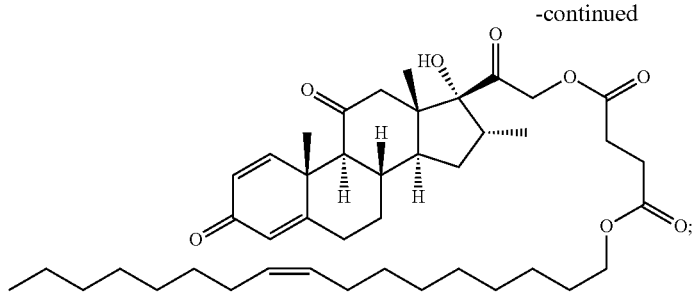
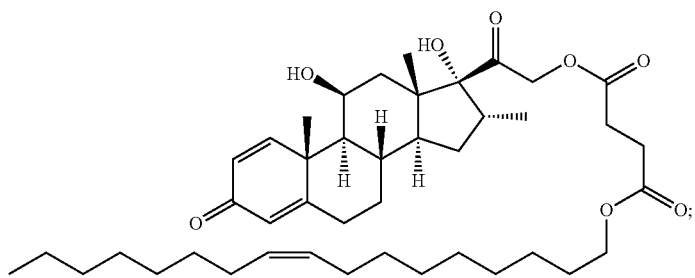
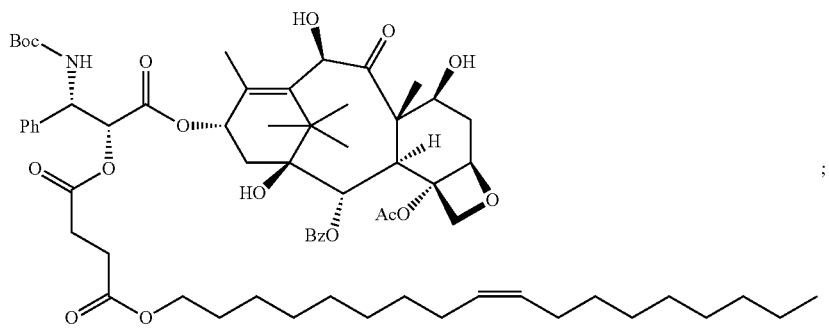
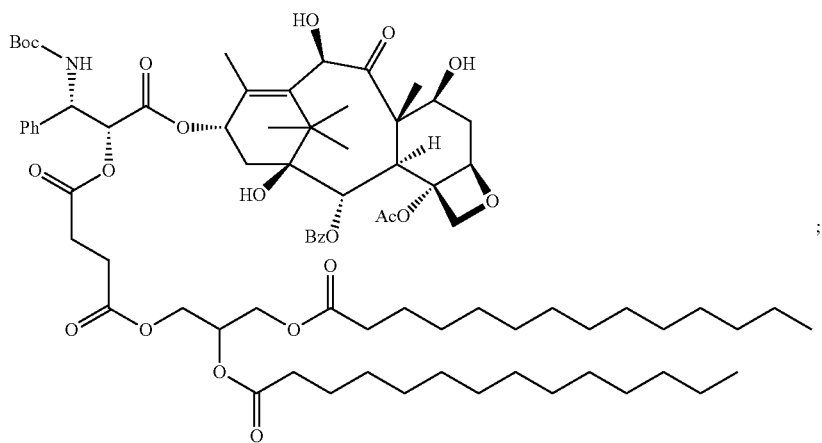

-continued
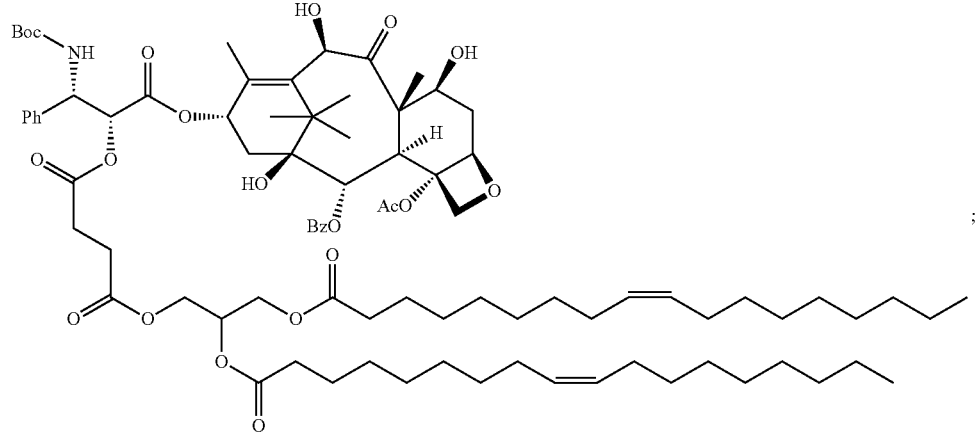
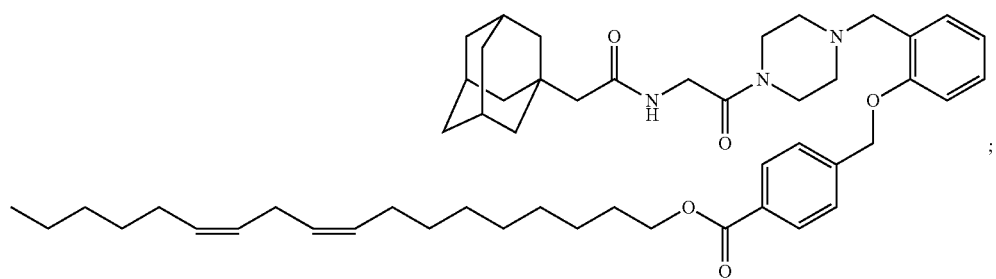
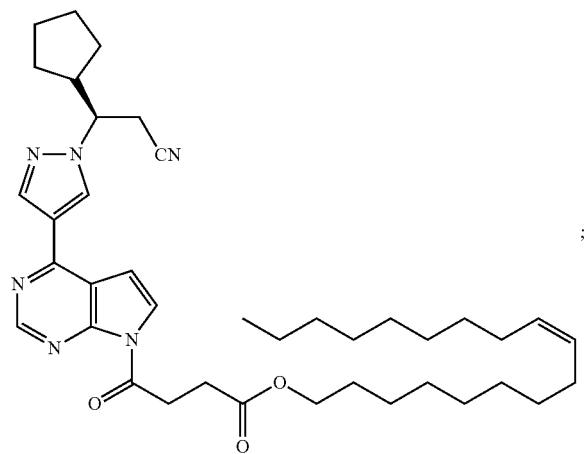
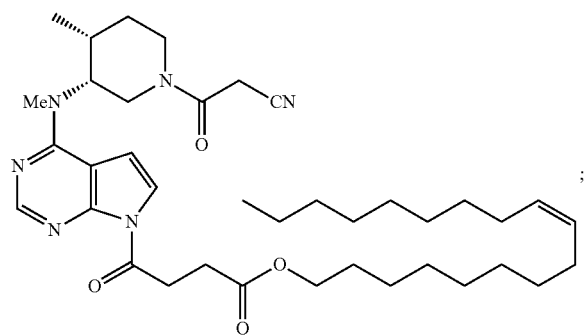

-continued

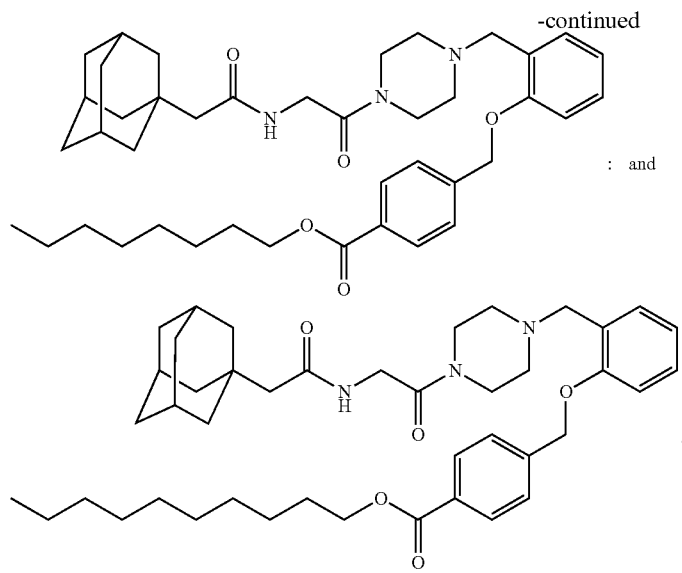

: and

Alternatively, the compound may be

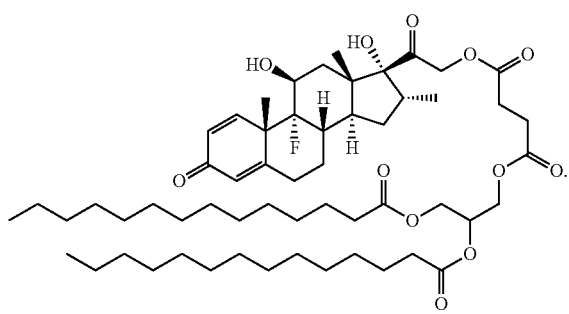

In accordance with another embodiment, there is provided a pharmaceutical composition, the pharmaceutical composition comprising a compound described herein and a pharmaceutically acceptable carrier.

In accordance with another embodiment, there is provided a compound described herein for treating cancer, autoimmune disease or infection.

In accordance with another embodiment, there is provided a pharmaceutical composition for treating cancer, autoimmune disease or infection, comprising compound described herein and a pharmaceutically acceptable carrier.

In accordance with another embodiment, there is provided a use of a compound described herein for treating cancer, autoimmune disease or infection.

In accordance with another embodiment, there is provided a use of a pharmaceutical composition described herein for treating cancer, autoimmune disease or infection.

In accordance with another embodiment, there is provided a use a compound described herein in the manufacture of a medicament.

In accordance with another embodiment, there is provided a use a compound described herein in the manufacture of a medicament for treating cancer, autoimmune disease or infection.

In accordance with another embodiment, there is provided a commercial package comprising (a) a compound described herein; and (b) instructions for the use.

In accordance with another embodiment, there is provided a commercial package comprising (a) a pharmaceutical composition described herein; and (b) instructions for the use.

Alternatively, the compound or composition may be use to treat any indication for which the drug of the A-Z drug moiety may be used to treat.

DETAILED DESCRIPTION

Figure 1:
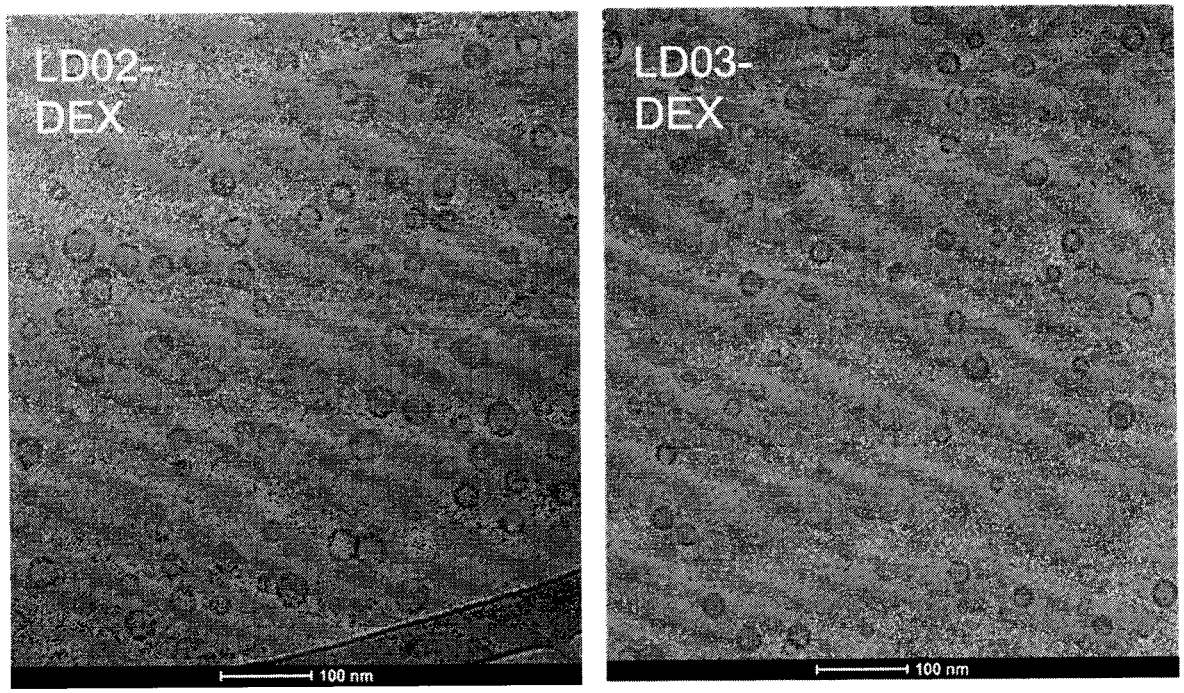
FIG. 1 shows ultrastructure of lipid-linked prodrugs formulations, wherein cryoTEM images showed bilayer vesicular structures for LNP containing LD02-DEX and LD03-DEX.

Those skilled in the art will appreciate that the point of covalent attachment of the moiety to the compounds as described herein may be, for example, and without limitation, cleaved under specified conditions. Specified conditions may include, for example, and without limitation, in vivo enzymatic or non-enzymatic means. Cleavage of the moiety may occur, for example, and without limitation, spontaneously, or it may be catalyzed, induced by another agent, or a change in a physical parameter or environmental parameter, for example, an enzyme, light, acid, temperature or pH. The moiety may be, for example, and without limitation, a protecting group that acts to mask a functional group, a group that acts as a substrate for one or more active or passive transport mechanisms, or a group that acts to impart or enhance a property of the compound, for example, solubility, bioavailability or localization.

In some embodiments, compounds of TABLE 1 (except LD07-DEX) and compounds described in the claims may be used for systemic treatment or localized treatment of at least one indication for which the prodrug is deemed suitable. In some embodiments, compounds of TABLE 1 (except LD07-DEX) and compounds described in the claims may be used in the preparation of a medicament or a composition for systemic treatment or localized treatment of an indication described herein. In some embodiments, methods of systemically treating or locally treating any of the indications described herein are also provided.

TABLE 1

Exemplary Compounds

| Compound Identifier (pro-drug) | Structure |
| --- | --- |
| $LD_{01}$-DEX (Dexamethasone) | 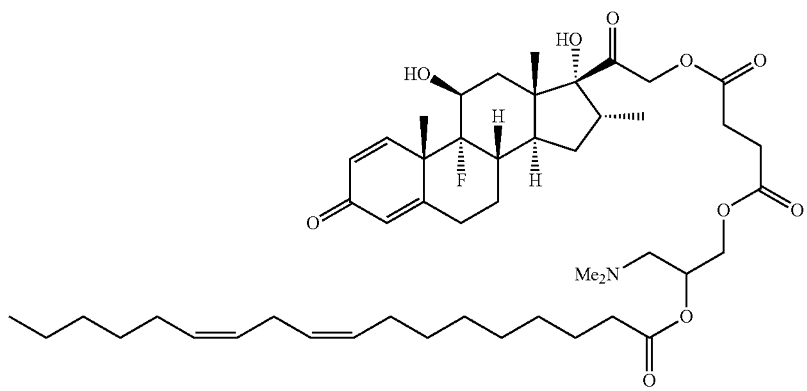 |
| $LD_{02}$-DEX (Dexamethasone) | 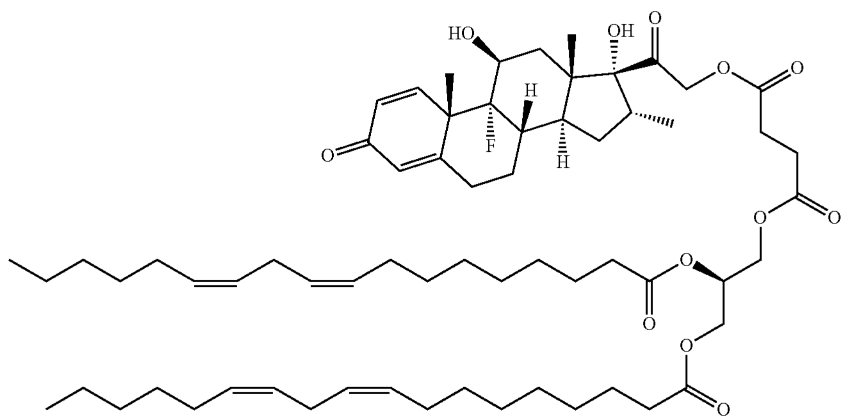 |
| $LD_{03}$-DEX (Dexamethasone) | 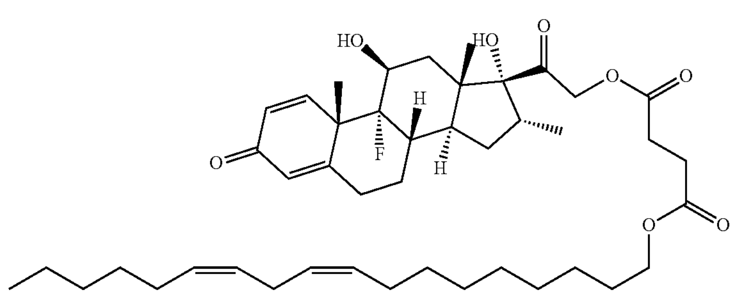 |

TABLE 1-continued
Exemplary Compounds
| Compound Identifier (pro-drug) | Structure |
|---|---|
| LD06-DEX (Dexamethasone) | 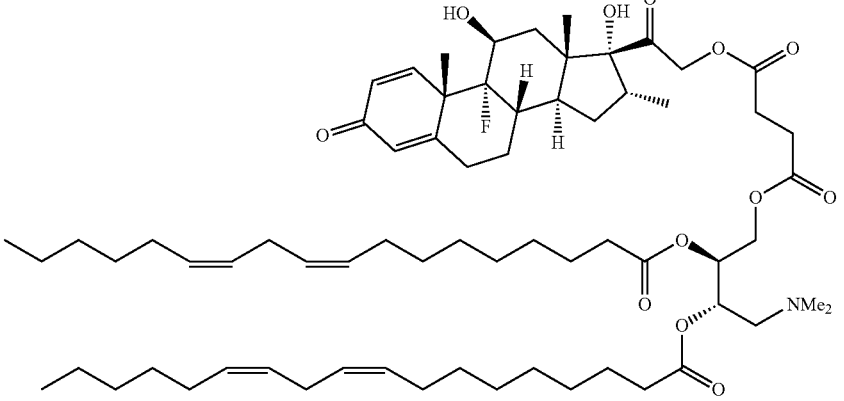 |
| LD07-DEX (Dexamethasone) | 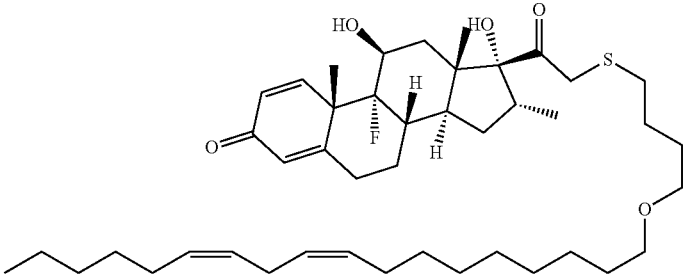 |
| LD12-ABN (Abiraterone) | 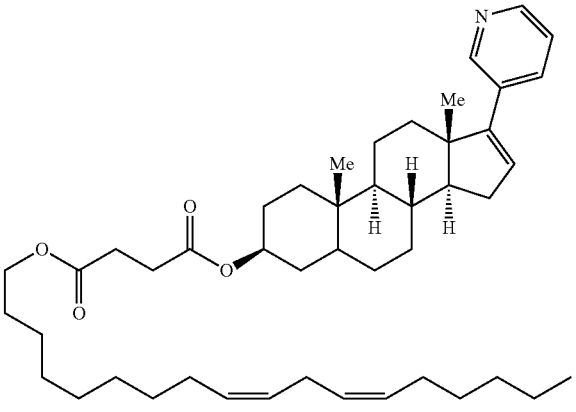 |
| LD01-METH (Methotrexate) Formula VII | 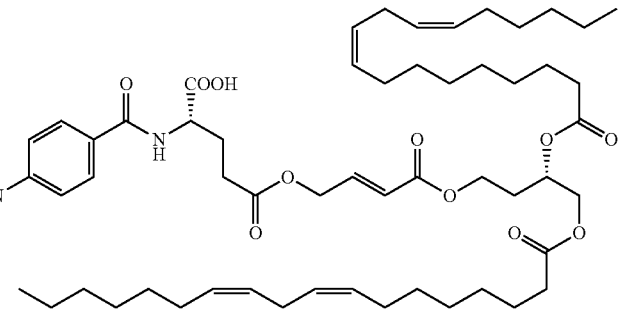 |

TABLE 1-continued

Exemplary Compounds

| Compound Identifier (pro-drug) | Structure |
| --- | --- |
| LD$_{10}$-DEX Formula X (Dexamethasone) | 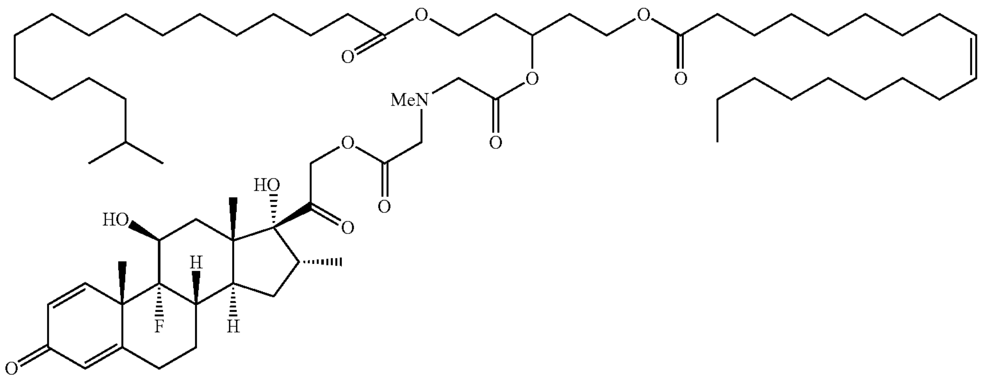 |
| LD$_{11}$-DEX Formula XI (Dexamethasone) | 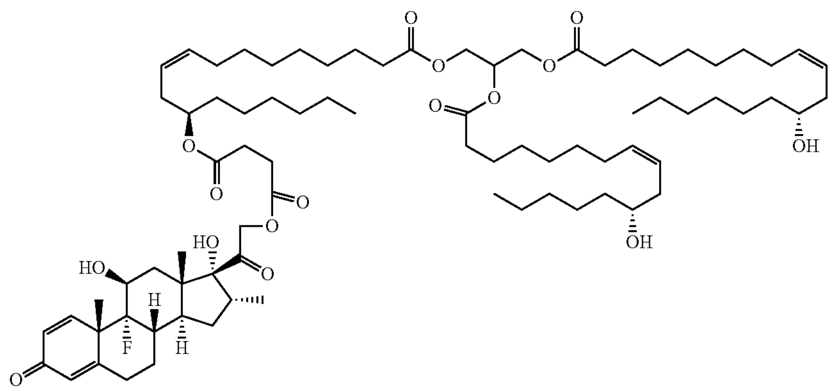 |
| LD$_{12}$-DEX Formula XII (Dexamethasone 3x) | 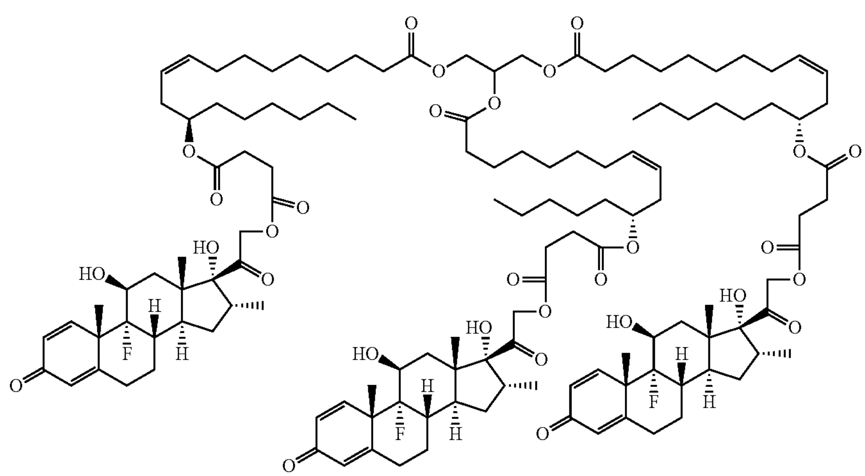 |

TABLE 1-continued

Exemplary Compounds

| Compound Identifier (pro-drug) | Structure |
|---|---|
| LD$_{13}$-DEX Formula XIII (Dexamethasone) | 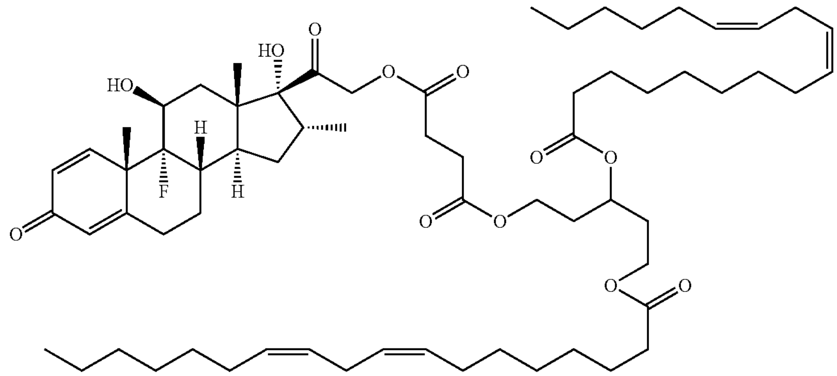 |
| LD$_{14}$-DEX Formula XIV (Dexamethasone) | 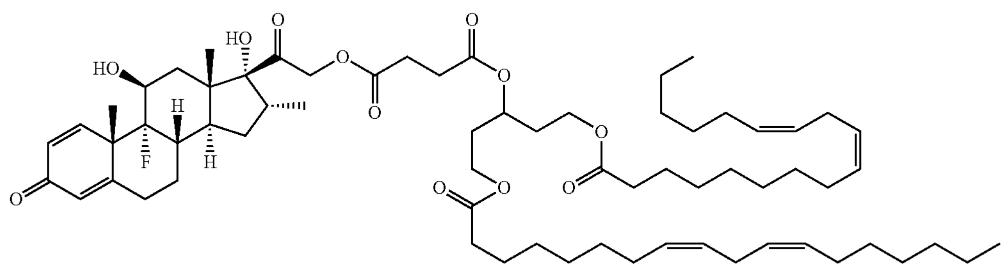 |
| LD$_{10}$-DTX (Docetaxel) | 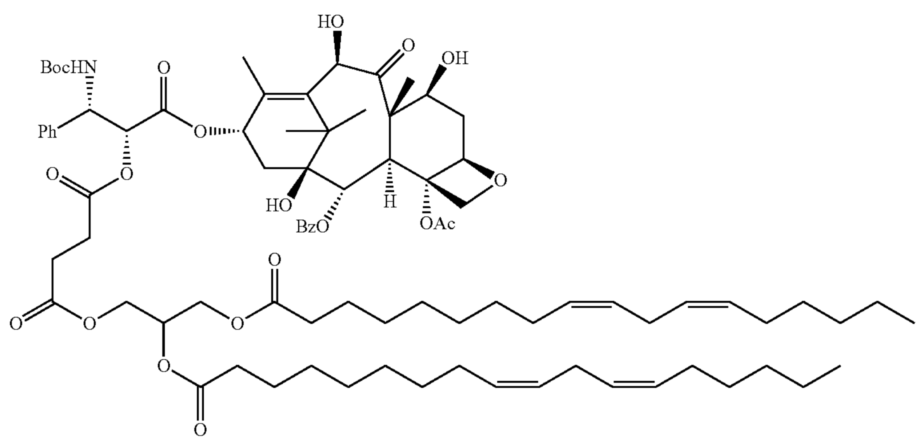 |
| LD$_{17}$-DEX (Dexamethasone) | 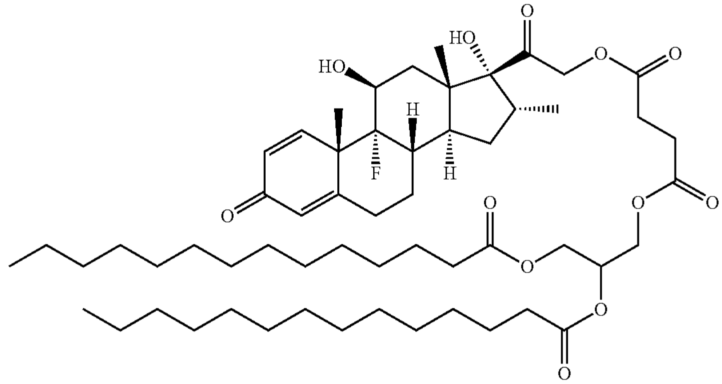 |

TABLE 1-continued

Exemplary Compounds

| Compound Identifier (pro-drug) | Structure |
| --- | --- |
| LD$_{19}$-PDN (Prednisone) | 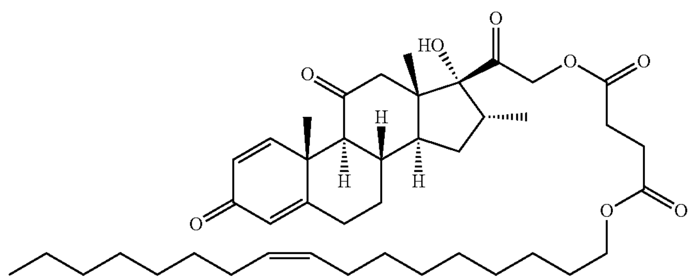 |
| LD$_{20}$-PDL (Prednisolone) | 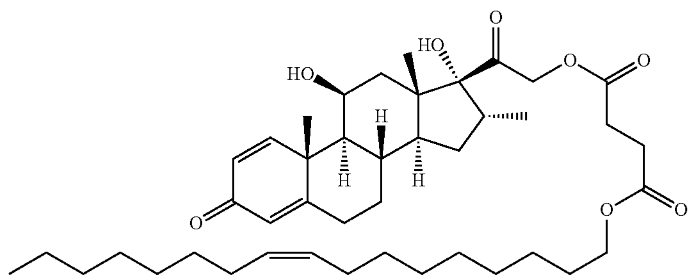 |
| LD$_{18}$-DTX (Docetaxel) | 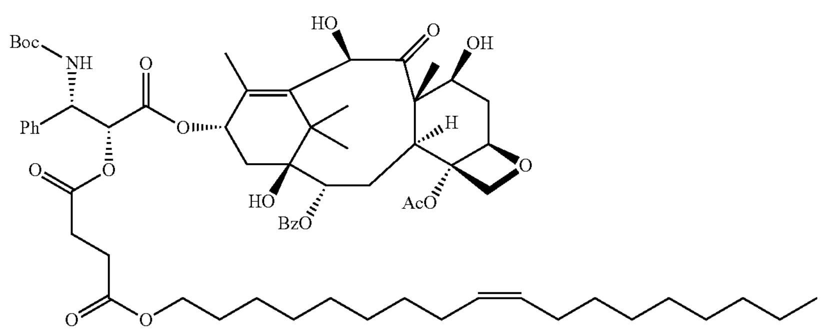 |
| LD$_{22}$-DTX (Docetaxel) | 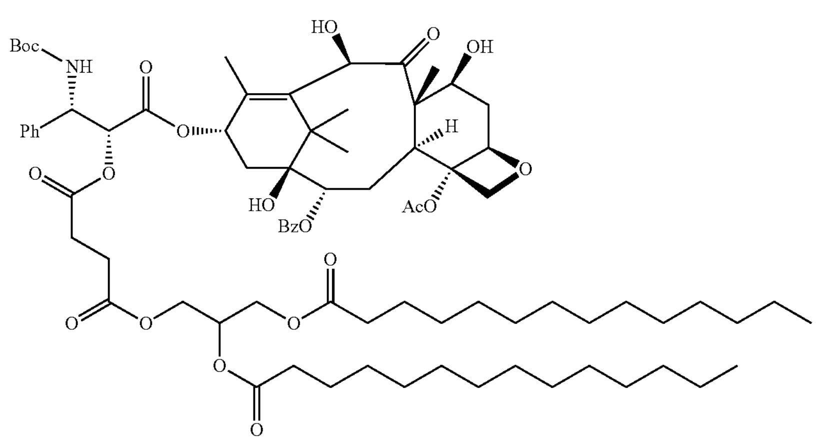 |

TABLE 1-continued

Exemplary Compounds

| Compound Identifier (pro-drug) | Structure |
| --- | --- |
| LD$_{23}$-DTX (Docetaxel) | 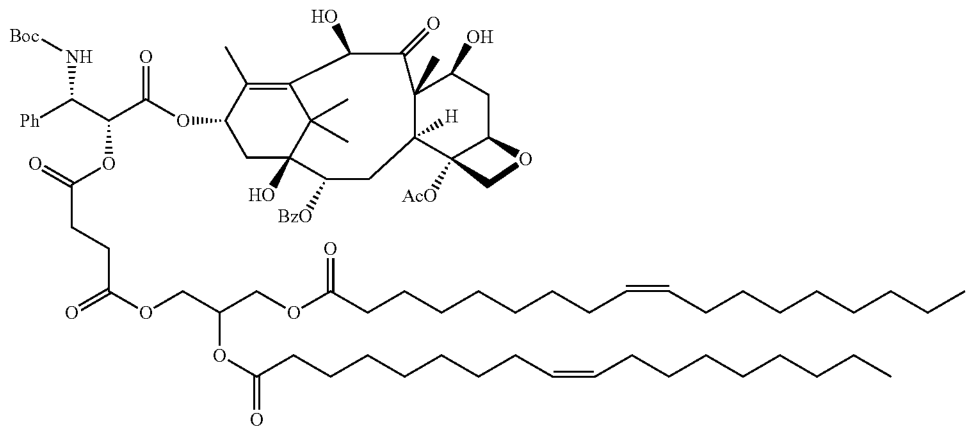 |
| LD$_{11}$-NPC$_1$ (NPC$_1$I) | 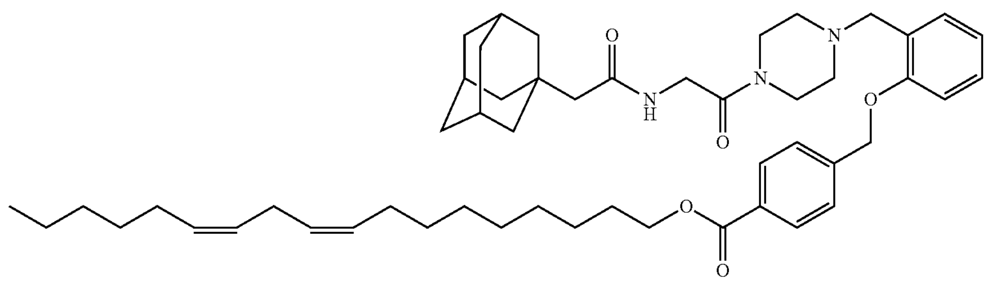 [SMILES: CCCCC/C=C\C/C=C\CCCCCCCCOC(=O)c1ccc(COc2ccccc2CN2CCN(C(=O)CNC(=O)CC34CC5CC(CC(C5)C3)C4)CC2)cc1] |
| LD$_{25}$-NPC$_1$ (NPC$_1$I) | 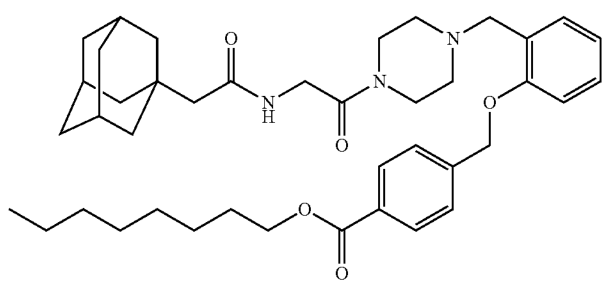 [SMILES: CCCCCCCCOC(=O)c1ccc(COc2ccccc2CN2CCN(C(=O)CNC(=O)CC34CC5CC(CC(C5)C3)C4)CC2)cc1] |
| LD$_{26}$-NPC$_1$ (NPC$_1$I) | 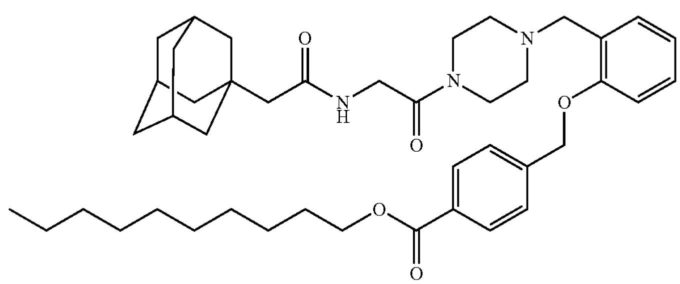 [SMILES: CCCCCCCCCCOC(=O)c1ccc(COc2ccccc2CN2CCN(C(=O)CNC(=O)CC34CC5CC(CC(C5)C3)C4)CC2)cc1] |

TABLE 1-continued

Exemplary Compounds

| Compound Identifier (pro-drug) | Structure |
|---|---|
| LD$_{01}$-RXN (Ruxolitinib) | 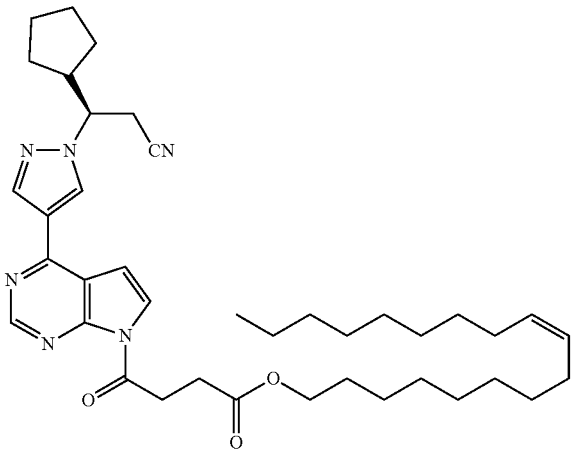 [SMILES: CCCCCCCC/C=C\CCCCCCCCOC(=O)CCC(=O)n1ccc2c(-c3cnn([C@H](CC#N)C4CCCC4)c3)ncnc21] |
| LD$_{01}$-TFN (Tofacitinib) | 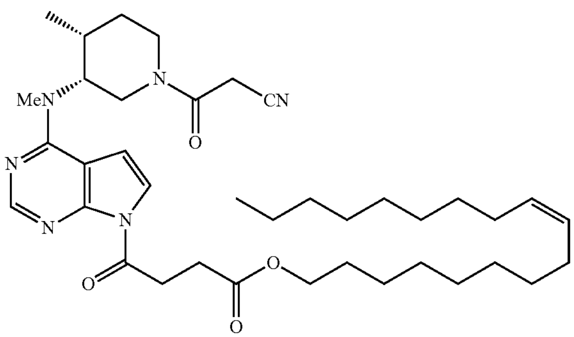 [SMILES: CCCCCCCC/C=C\CCCCCCCCOC(=O)CCC(=O)n1ccc2c(N(C)[C@H]3CN(C(=O)CC#N)CC[C@H]3C)ncnc21] |

The pharmaceutical drugs contemplated in the present application may be described with the general structure A-Z shown below, wherein Z may represent an OH, or an NH, or an NH$_2$, or a COOH group attached to the drug's main molecular framework represented by A. The drug may also incorporate multiple Z groups, which may be, independently, an OH, or an NH, or an NH$_2$, or a COOH, as indicated above. The lipid-linked pro-drugs prepared as described herein may be administered to human patients for the purpose of treating a disease, illness, or other undesirable physiological condition, which is treatable or curable with the drug.

Some examples of drugs are include but not limited to, Docetaxel, Methotrexate, SN-38, NPC$_1$I, Amprenavir, Amphotericin B, Bexarotene, Calcitrol, Cyclosporin A, Digoxin, Doxercalciferol, Dronabinol, Etoposide, Fulvestrant, Paricalcitol, Teniposide, Isotretinoin, Tretinoin, Valproic acid, Paclitaxel, Valrubicin, Propofol, Mycophenolic acid, Lovastatin, Lamivudine, Zidovudine, Abacavir, Emitricitabine, Atazanavir, Cobicistat, Elvitegravir, Isonazid, Albendazole, Lisinapril, Amlodipine, Isotretinoin, Baclofen, Benznidazole, Nifurtimox, Mefloquine, Sulfadoxine, Pyrimethamine, Chlorproguanil, 6-Mercaptopurine, 1-Thyroxine, Glyburide, MCC950, Parthenolide, Tauroursodeoxycholic acid, Ruxolitinib, Tofacitinib, Cyclosporine, Tacrolimus, Everolimus, Sirolimus, Azathioprine, Leflunomide, Mycophenolate, Dexamethasone, Budesonide, Prednisone, Prednisolone, Methylprednisolone, Hydrocortisone, Cortisone, Fludrocortisone, Betamethasone, Triamcinolone, Triamcinolone acetonide, Flunisolide, Beclamethasone, Fluticasone, Mometasone, Flumethasone, Isoflupredone, Corticosterone, Desoxycortone acetate, Desoxycortone enanthate, 11-Deoxycorticosterone, 11-Deoxycortisol, and Aldosterone.

Alternatively, examples of drugs are include but not limited to, Tacrolimus, SN-38, Methotrexate, Docetaxel, NPC$_1$I, Amprenavir, Amphotericin B, Bexarotene, Calcitrol, Cyclosporin A, Digoxin, Doxercalciferol, Dronabinol, Etoposide, Fulvestrant, Paricalcitol, Teniposide, Isotretinoin, Sirolimus, Tretinoin, Valproic acid, Paclitaxel, Valrubicin, Propofol, Mycophenolic acid, Lovastatin, Lamivudine, Zidovudine, Abacavir, Emitricitabine, Atazanavir, Cobicistat, Elvitegravir, Isonazid, Albendazole, Lisinapril, Amlodipine, Isotretinoin, Baclofen, Benznidazole, Nifurtimox, Mefloquine, Sulfadoxine, Pyrimethamine, Chlorproguanil, 6-Mercaptopurine, 1-Thyroxine, Glyburide, MCC950, Parthenolide, Tauroursodeoxycholic acid, Ruxolitinib and Tofacitinib.

The lipid-linked prodrug formulations described herein are based upon substances that are obtained by exploiting group(s) Z to covalently attach the drug to an appropriate lipid. Generally, an appropriate lipid-drug conjugate as described herein has a log P equal to or greater than 5 (Viswanadhan, V. N.; Ghose, A. K.; Revankar, G. R.; Robins, R. K., J. Chem. Inf. Comput. Sci., 1989, 29, 163-172, or using program such as Marvin (ChemAxon)); and is therefore poorly soluble or insoluble in water, but soluble in common organic solvents such as ethanol, chloroform, ethyl acetate, dichloromethane, isopropanol, etc.

The molecular structure of said lipid may incorporate functional groups that enable the covalent attachment of the drug to the lipid. Examples of such functional groups may be OH, SH, NH, $NH_2$, COOH.

In some embodiments the pro-drug would be at least weakly hydrophobic. Furthermore, in some embodiments the drug would be linked to the lipid moiety through a biodegradable linker, such as an ester linkage. However, other biodegradable linkers are contemplated (for example, phosphate).

A 'drug moiety' as used herein, is any pharmaceutical agent capable of being covalently bound to the lipid as described herein. In some embodiments a drug moiety may exclude steroids, quinoline containing compounds or Na+/K+ ATPase binding moieties. In some embodiments a drug moiety may exclude steroids. In some embodiments a drug moiety may exclude quinoline containing compounds. In some embodiments a drug moiety may exclude Na+/K+ ATPase binding moieties. In some embodiments the Na+/K+ ATPase binding moieties may be cardiac glycosides. In some embodiments a drug moiety may exclude cardiac glycosides. In some embodiments a drug moiety may exclude cardiac glycosides and quinolone-containing compounds. The quinolone-containing compound may be 4-aminoquinoline, 8-aminoquinoline or 4-methanolquinoline. The cardiac glycosides may be selected from one or more of the following: acetyldigitoxins; acetyldigoxins; cymarine; digitoxin; digitoxigenin; digoxigenin; digoxin; medigoxin; neoconvalloside; ouabain; dihydroouabain; strophanthins; strophanthidin; bufenolides; bufanolide; daigremontianin; cardenolide; helveticoside; k-stophantidin; latanoside C; procillardin A; arenobufagin; bufotalin; cinobufagin; marinobufagin; scilliroside; acetyldigitoxin; acetyldigoxin; deslanoside; medigoxin; gitoformate; digremontianin; peruvoside. In some embodiments, if the drug moiety is a steroid, the steroid drug moiety (A-Z) may attach —Y-M-C(═O)— or —Y-M- via the 5 membered ring of the steroid.

As used herein a fatty acyl group [R'C(═O)], may be an R' having a $C_9$-$C_{29}$ linear or branched carbon chain, facultatively incorporating C═C double bonds of E or Z geometry and/or substituents such as OH groups. Examples of such fatty acyl groups (parent acid) are but are not limited to: Capryl (capric acid), Lauroyl (lauric acid), Myristyl (myristic acid), Myristoleyl (myristoleic acid), Palmitoyl (palmitic acid), Isopalmitoyl (isopalmitic acid), Palmitoleyl (palmitoleic acid), Sapienoyl (sapienic acid), Stearoyl (stearic acid), Isostearoyl (isostearic acid), Oleyl (oleic acid), Elaidoyl (elaidic acid), Vaccenoyl (vaccenic acid), Linoleyl (linoleic acid), Linoelaidoyl (linoelaidic acid), Linolenyl (linolenic acid), Ricinoleyl (ricinoleic acid), Pristanoyl (pristanic acid), Arachidoyl (arachidic acid), Arachidonoyl (arachidonic acid), Eicosapentaenoyl (eicosapentaenoic acid), Phytanoyl (phytanic acid), Behenoyl (behenic acid), Erucoyl (erucic acid), Docosahexaenoyl (docosahexaenoic acid), Lignoceryl (lignoceric acid), Cerotoyl (cerotic acid), Montanoyl (montanic acid), Melissoyl (melissic acid). Alternatively, a fatty acyl group, as described herein, may originally have an OH group (for example: ricinoleyl), wherein the OH group has been covalently modified through the attachment to a linker or a prodrug and linker as described herein.

The relative hydrophobicity of the drug and lipid moieties, the presence of charged/ionizable groups, the type of biodegradable linker, etc. may be tailored to the particular pro-drug and/or the particular target for the lipid-linked prodrugs (or lipid nanoparticles (LNP)) described herein. The hydrophobic properties of the prodrug (comprised of the drug and lipid moieties) should allow these prodrugs to be easily incorporated by simply adding the drug to the lipid formulation mixture without further modification of the formulation process. In addition, the hydrophobicity may also allow stable retention in lipid-linked prodrugs formulations, endowing the prodrug with an improved toxicity profile compared. Some LNP formulations occasionally exhibit drug release after systemic administration, resulting in undesirable pharmacokinetic properties [Charrois and Allen (2004); Cui et al. (2007); and Johnston et al. (2006)]. In contrast, most embodiments of lipid-linked prodrugs described herein should exhibit minimal leakage after systemic administration until taken up into target cells. Finally, while the hydrophobicity of the prodrug must be sufficient to achieve efficient encapsulation/retention, preferably does not result in the prodrug being shielded in the lipid moiety and thus not released when in the appropriate environment. In cases where the lipid-linked prodrug has hydrophobic characteristics, the prodrug distribution in the lipid allows access to the biodegradable linker. Release of the active drug may then occur following uptake through the activity of appropriate intracellular enzymes in cleaving the biodegradable linker.

These lipid-linked prodrugs do not require active (i.e. pH gradient) loading [Nichols and Deamer (1976); and Mayer et al. (1986)] to achieve efficient incorporation into the lipid. Since the prodrugs do not need to be weak bases, this approach allows incorporation of drugs into lipid nanoparticles (LNPs), where the drug would not be encapsulated using conventional approaches. The benefits of LNP-mediated drug delivery have been well described, including enhanced delivery to sites of disease and facilitated uptake into target cells, resulting in increased potency and reduced toxicity (vs free drug) due to lower drug levels in non-target tissues [Allen and Cullis (2013)].

As used herein, an ionizable moiety may be any atom or any molecule that acquires a negative or positive charge by losing or gaining protons to form ions. Examples of ionizable moieties are —NH, —NHMe, $—NMe_2$, —COOH, —OH, $—NH^+$, $—NH_3^+$, $—NH_2^+$, —SH, etc. Having an ionizable moiety on lipid-linked prodrug can influence the hydrophobicity index of the prodrug (for example, see TABLE 2).

Compounds as described herein may be in the free form or in the form of a salt thereof. In some embodiment, compounds as described herein may be in the form of a pharmaceutically acceptable salt, which are known in the art (Berge S. M. et al., *J. Pharm. Sci.* (1977) 66(1):1-19). Pharmaceutically acceptable salt as used herein includes, for example, salts that have the desired pharmacological activity of the parent compound (salts which retain the biological effectiveness and/or properties of the parent compound and which are not biologically and/or otherwise undesirable). Compounds as described herein having one or more functional groups capable of forming a salt may be, for example, formed as a pharmaceutically acceptable salt. Compounds containing one or more basic functional groups may be capable of forming a pharmaceutically acceptable salt with, for example, a pharmaceutically acceptable organic or inorganic acid. Pharmaceutically acceptable salts may be derived from, for example, and without limitation, acetic acid, adipic acid, alginic acid, aspartic acid, ascorbic acid, benzoic acid, benzenesulfonic acid, butyric acid, cinnamic acid, citric acid, camphoric acid, camphorsulfonic acid, cyclopentanepropionic acid, diethylacetic acid, digluconic acid, dodecylsulfonic acid, ethanesulfonic acid, formic acid, fumaric acid, glucoheptanoic acid, gluconic acid, glycerophosphoric acid, glycolic acid, hemisulfonic acid, heptanoic acid, hexanoic acid, hydrochloric acid, hydrobromic acid, hydriodic acid, 2-hydroxyethanesulfonic acid, isonicotinic acid, lactic acid, malic acid, maleic acid, malonic acid, mandelic acid, methanesulfonic acid, 2-napthalenesulfonic acid, naphthalenedisulphonic acid, p-toluenesulfonic acid, nicotinic acid, nitric acid, oxalic acid, pamoic acid, pectinic acid, 3-phenylpropionic acid, phosphoric acid, picric acid, pimelic acid, pivalic acid, propionic acid, pyruvic acid, salicylic acid, succinic acid, sulfuric acid, sulfamic acid, tartaric acid, thiocyanic acid or undecanoic acid. Compounds containing one or more acidic functional groups may be capable of forming pharmaceutically acceptable salts with a pharmaceutically acceptable base, for example, and without limitation, inorganic bases based on alkaline metals or alkaline earth metals or organic bases such as primary amine compounds, secondary amine compounds, tertiary amine compounds, quaternary amine compounds, substituted amines, naturally occurring substituted amines, cyclic amines or basic ion-exchange resins. Pharmaceutically acceptable salts may be derived from, for example, and without limitation, a hydroxide, carbonate, or bicarbonate of a pharmaceutically acceptable metal cation such as ammonium, sodium, potassium, lithium, calcium, magnesium, iron, zinc, copper, manganese or aluminum, ammonia, benzathine, meglumine, methylamine, dimethylamine, trimethylamine, ethylamine, diethylamine, triethylamine, isopropylamine, tripropylamine, tributylamine, ethanolamine, diethanolamine, 2-dimethylaminoethanol, 2-diethylaminoethanol, dicyclohexylamine, lysine, arginine, histidine, caffeine, hydrabamine, choline, betaine, ethylenediamine, glucosamine, glucamine, methylglucamine, theobromine, purines, piperazine, piperidine, procaine, N-ethylpiperidine, theobromine, tetramethylammonium compounds, tetraethylammonium compounds, pyridine, N,N-dimethylaniline, N-methylpiperidine, morpholine, N-methylmorpholine, N-ethylmorpholine, dicyclohexylamine, dibenzylamine, N,N-dibenzylphenethylamine, 1-ephenamine, N,N'-dibenzylethylenediamine or polyamine resins. In some embodiments, compounds as described herein may contain both acidic and basic groups and may be in the form of inner salts or zwitterions, for example, and without limitation, betaines. Salts as described herein may be prepared by conventional processes known to a person skilled in the art, for example, and without limitation, by reacting the free form with an organic acid or inorganic acid or base, or by anion exchange or cation exchange from other salts. Those skilled in the art will appreciate that preparation of salts may occur in situ during isolation and purification of the compounds or preparation of salts may occur by separately reacting an isolated and purified compound.

In some embodiments, compounds and all different forms thereof (e.g. free forms, salts, polymorphs, isomeric forms) as described herein may be in the solvent addition form, for example, solvates. Solvates contain either stoichiometric or non-stoichiometric amounts of a solvent in physical association the compound or salt thereof. The solvent may be, for example, and without limitation, a pharmaceutically acceptable solvent. For example, hydrates are formed when the solvent is water or alcoholates are formed when the solvent is an alcohol.

In some embodiments, compounds and all different forms thereof (e.g. free forms, salts, solvates, isomeric forms) as described herein may include crystalline and amorphous forms, for example, polymorphs, pseudopolymorphs, conformational polymorphs, amorphous forms, or a combination thereof. Polymorphs include different crystal packing arrangements of the same elemental composition of a compound. Polymorphs usually have different X-ray diffraction patterns, infrared spectra, melting points, density, hardness, crystal shape, optical and electrical properties, stability and/or solubility. Those skilled in the art will appreciate that various factors including recrystallization solvent, rate of crystallization and storage temperature may cause a single crystal form to dominate.

In some embodiments, compounds and all different forms thereof (e.g. free forms, salts, solvates, polymorphs) as described herein include isomers such as geometrical isomers, optical isomers based on asymmetric carbon, stereoisomers, tautomers, individual enantiomers, individual diastereomers, racemates, diastereomeric mixtures and combinations thereof, and are not limited by the description of the formula illustrated for the sake of convenience.

In some embodiments, compounds may include analogs, isomers, stereoisomers, or related derivatives. Compounds of the present invention may include compounds related to the compounds of TABLE 1 by substitution or replacement of certain substituents with closely related substituents, for instance replacement of a halogen substituent with a related halogen (i.e. bromine instead of chlorine, etc.) or replacement of an alkyl chain with a related alkyl chain of a different length, and the like. In other embodiments, compounds may include compounds within a generic or Markush structure, as determined from structure-activity relationships identified from the data presented in TABLE 2 and in the below examples.

In some embodiments, pharmaceutical compositions as described herein may comprise a salt of such a compound, preferably a pharmaceutically or physiologically acceptable salt. Pharmaceutical preparations will typically comprise one or more carriers, excipients or diluents acceptable for the mode of administration of the preparation, be it by injection, inhalation, topical administration, lavage, or other modes suitable for the selected treatment. Suitable carriers, excipients or diluents (used interchangeably herein) are those known in the art for use in such modes of administration.

Suitable pharmaceutical compositions may be formulated by means known in the art and their mode of administration and dose determined by the skilled practitioner. For parenteral administration, a compound may be dissolved in sterile water or saline or a pharmaceutically acceptable vehicle used for administration of non-water soluble compounds such as those used for vitamin K. For enteral administration, the compound may be administered in a tablet, capsule or dissolved in liquid form. The tablet or capsule may be enteric coated, or in a formulation for sustained release. Many suitable formulations are known, including, polymeric or protein microparticles encapsulating a compound to be released, ointments, pastes, gels, hydrogels, or solutions which can be used topically or locally to administer a compound. A sustained release patch or implant may be employed to provide release over a prolonged period of time. Many techniques known to one of skill in the art are described in *Remington: the Science & Practice of Phar-* macy by Alfonso Gennaro, 20th ed., Lippencott Williams & Wilkins, (2000). Formulations for parenteral administration may, for example, contain excipients, polyalkylene glycols such as polyethylene glycol, oils of vegetable origin, or hydrogenated naphthalenes. Biocompatible, biodegradable lactide polymer, lactide/glycolide copolymer, or polyoxyethylene-polyoxypropylene copolymers may be used to control the release of the compounds. Other potentially useful parenteral delivery systems for modulatory compounds include ethylene-vinyl acetate copolymer particles, osmotic pumps, implantable infusion systems, and liposomes. Formulations for inhalation may contain excipients, for example, lactose, or may be aqueous solutions containing, for example, polyoxyethylene-9-lauryl ether, glycocholate and deoxycholate, or may be oily solutions for administration in the form of nasal drops, or as a gel.

Compounds or pharmaceutical compositions as described herein or for use as described herein may be administered by means of a medical device or appliance such as an implant, graft, prosthesis, stent, etc. Also, implants may be devised which are intended to contain and release such compounds or compositions. An example would be an implant made of a polymeric material adapted to release the compound over a period of time.

An "effective amount" of a pharmaceutical composition as described herein includes a therapeutically effective amount or a prophylactically effective amount. A "therapeutically effective amount" refers to an amount effective, at dosages and for periods of time necessary, to achieve the desired therapeutic result, for example, reduced tumor size, increased life span or increased life expectancy. A therapeutically effective amount of a compound may vary according to factors such as the disease state, age, sex, and weight of the subject, and the ability of the compound to elicit a desired response in the subject. Dosage regimens may be adjusted to provide the optimum therapeutic response. A therapeutically effective amount is also one in which any toxic or detrimental effects of the compound are outweighed by the therapeutically beneficial effects. A "prophylactically effective amount" refers to an amount effective, at dosages and for periods of time necessary, to achieve the desired prophylactic result, for example, smaller tumors, increased life span, increased life expectancy. Typically, a prophylactic dose is used in subjects prior to or at an earlier stage of disease, so that a prophylactically effective amount may be less than a therapeutically effective amount.

It is to be noted that dosage values may vary with the severity of the condition to be alleviated. For any particular subject, specific dosage regimens may be adjusted over time according to the individual need and the professional judgment of the person administering or supervising the administration of the compositions. Dosage ranges set forth herein are exemplary only and do not limit the dosage ranges that may be selected by medical practitioners. The amount of active compound(s) in the composition may vary according to factors such as the disease state, age, sex, and weight of the subject. Dosage regimens may be adjusted to provide the optimum therapeutic response. For example, a single bolus may be administered, several divided doses may be administered over time or the dose may be proportionally reduced or increased as indicated by the exigencies of the therapeutic situation. It may be advantageous to formulate parenteral compositions in dosage unit form for ease of administration and uniformity of dosage.

In general, compounds as described herein should be used without causing substantial toxicity. Toxicity of the compounds as described herein can be determined using standard techniques, for example, by testing in cell cultures or experimental animals and determining the therapeutic index, i.e., the ratio between the LD50 (the dose lethal to 50% of the population) and the LD100 (the dose lethal to 100% of the population). In some circumstances however, such as in severe disease conditions, it may be appropriate to administer substantial excesses of the compositions. Some compounds as described herein may be toxic at some concentrations. Titration studies may be used to determine toxic and non-toxic concentrations.

Compounds as described herein may be administered to a subject. As used herein, a "subject" may be a human, non-human primate, rat, mouse, cow, horse, pig, sheep, goat, dog, cat, etc. The subject may be suspected of having or at risk for having an indication for which a therapeutic moiety may provide a benefit.

Various alternative embodiments and examples of the invention are described herein. These embodiments and examples are illustrative and should not be construed as limiting the scope of the invention.

Materials and Methods

Chemistry

All reagents and solvents were purchased from commercial suppliers and used without further purification unless otherwise stated, except THF, (freshly distilled from Na/benzophenone under Ar), and Et$_3$N and CH$_2$Cl$_2$ (freshly distilled from CaH$_2$ under Ar). NMR Chemical shifts are reported in parts per million (ppm) on the δ scale and coupling constants, J, are in hertz (Hz). Multiplicities are reported as "s" (singlet), "d" (doublet), "dd" (doublet of doublets), "dt" (doublet of triplets), "ddd" (doublet of doublets of doublets), "t" (triplet), "td" (triplet of doublets), "q" (quartet), "quin" (quintuplet), "sex" (sextet), "m" (multiplet), and further qualified as "app" (apparent) and "br" (broad).

Procedures for Synthesis of Lipids

SCHEME 1: Scheme for synthesis of Lipid 3, 2-linoleoyl-3-dimethylamino-1,2-propanediol.

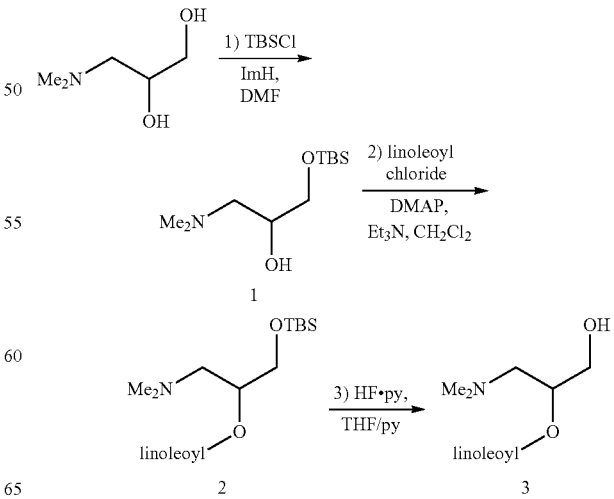

Compound 1: 1-((tert-butyldimethylsilyboxy)-3-dimethylaminopropan-2-ol

Solid TBSCl (1.36 g, 9.00 mmol, 1.00 equiv.) was added to a stirring, ice-cold $CH_2Cl_2$ (11 mL) solution of 3-dimethylaminopropane-1,2-diol (1.07 g, 9.00 mmol) and imidazole (613 mg, 9.00 mmol, 1.00 equiv.) in a round bottom flask under argon. After 2.5 h, the reaction mixture was diluted with $CH_2Cl_2$ and washed with distilled water (1×25 mL). The aqueous layer was extracted with $CH_2Cl_2$ (1×15 mL) and the combined organic layers washed with brine (1×15 mL), dried over $Na_2SO_4$ and concentrated to afford a clear, colourless oil as silyl ether 1 (1.83 g, 87% yield), which was used without further purification.

$R_f$=0.09 ($SiO_2$, 50:50 EtOAc/hexanes);
$^1H$ NMR (300 MHz, $CDCl_3$): δ 3.80-3.68 (m, 1H), 3.60 (m, 1H), 2.39 (dd, J=12.3, 9.0 Hz, 1H), 2.34-2.24 (m, 1H), 2.29 (s, 6H), 0.90 (s, 9H), 0.07 (s, 6H).

Compound 2: 1-(tert-butyldimethylsilyl)-2-linoleoyl-3-dimethylaminopropane-1,2-diol Linoleoyl chloride was prepared by adding oxalyl chloride (0.30 mL, 3.60 mmol, 1.80 equiv.) to a stirring, room temperature benzene (5 mL) solution of linoleic acid (673 mg, 2.40 mmol, 1.20 equiv. relative to alcohol) and DMF (18 µL, 0.24 mmol, 0.12 equiv.) in a round bottom flask under argon. After 3 h, the volatiles were removed on a rotary evaporator and the residue azeotroped with benzene (2×5 mL), then dried under high vacuum for 3 h and used immediately without further purification.

A $CH_2Cl_2$ (4 mL) solution of alcohol 1 (467 mg, 2.00 mmol, 1.00 equiv.) and $Et_3N$ (0.69 mL, 5.00 mmol, 2.50 equiv.) was added to a stirring, ice-cold $CH_2Cl_2$ (4 mL) solution of the linoleoyl chloride prepared above in a round bottom flask under argon, followed by solid DMAP (293 mg, 2.40 mmol, 1.20 equiv.). The reaction mixture was allowed to warm up over 14 h, then diluted with $CH_2Cl_2$, washed with aq. 5% $NaHCO_3$ (2×10 mL), dried over $Na_2SO_4$ and concentrated on a rotary evaporator to afford the crude as a brown semi-solid. The crude was purified by flash column chromatography (130 mL $SiO_2$, 79:20:1→69:30:1 hexanes/EtOAc/$Et_3N$) to afford a clear, yellow oil as desired ester 2 (828 mg, 84% yield).

$R_f$=0.39 ($SiO_2$, 50:50 EtOAc/hexanes);
$^1H$ NMR (300 MHz, $CDCl_3$): δ 5.37-5.25 (m, 4H), 5.09-4.95 (m, 1H), 3.76-3.63 (m, 2H), 2.77 (t, J=5.8 Hz, 2H), 2.56-2.44 (m, 2H), 2.40-20 (m, 2H), 2.27 (s, 6H), 2.04 (q, J=6.4 Hz, 4H), 1.62 (t, J=7.0 Hz, 2H), 1.45-1.20 (m, 16H), 0.88 (app s, 12H), 0.04 (s, 6H).

Compound 3: 2-linoleoyl-3-dimethylaminopropane-1,2-diol

Neat HF.pyridine solution (68 µL of 70% HF in pyridine, 0.54 mmol, 3.00 equiv.) was added to a stirring, ice-cold THF (1.2 mL) solution of pyridine (44 µL, 0.54 mmol, 3.00 equiv.) and silyl ether 2 (90 mg, 0.18 mmol) in a round bottom flask under argon. After 2 h, the reaction mixture was quenched with aq. 5% $NaHCO_3$. The mixture was extracted with EtOAc (3×5 mL), then the combined organic extracts were washed with brine, dried over $Na_2SO_4$ and concentrated on a rotary evaporator to afford primary alcohol 3 (68 mg, theoretical yield of 69 mg) as a clear, colourless oil that was used immediately and without further purification. It should be noted that complete transesterification to the primary alcohol was observed (TLC, $^1H$ NMR) in <24 h when stored neat at −20° C.

SCHEME 2: Scheme for synthesis of Lipid 4, 2,3-dilinoleoyl glycerol hemisuccinate.

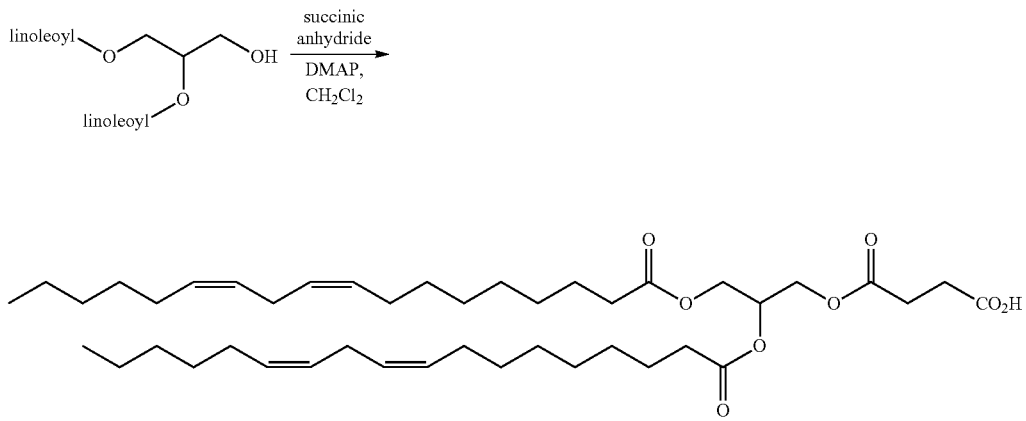

Compound 4: 2,3-dilinoleoyl glycerol hemisuccinate

Solid succinic anhydride (67 mg, 0.66 mmol, 2.0 equiv.) and DMAP (102 mg, 0.83 mmol, 2.5 equiv.) were added to a stirring room temperature $CH_2Cl_2$ (3.5 mL) solution of 1,2-dilinoleoyl glycerol [Abe et al. (2011)] (205 mg, 0.33 mmol, 1.0 equiv.) in a round bottom flask under argon. After 12 hours, the reaction was quenched with aq. 1 M HCl, extracted with $CH_2Cl_2$ (2×15 mL), the combined organic extracts were then washed with aq. 1 M HCl (1×15 mL), dried over $Na_2SO_4$ and concentrated on a rotary evaporator to afford hemisuccinate 4 (quantitative yield) as a pale yellow oil that was used without further purification.

SCHEME 3: Scheme for synthesis of Lipid 5, linoleyl alcohol hemisuccinate.

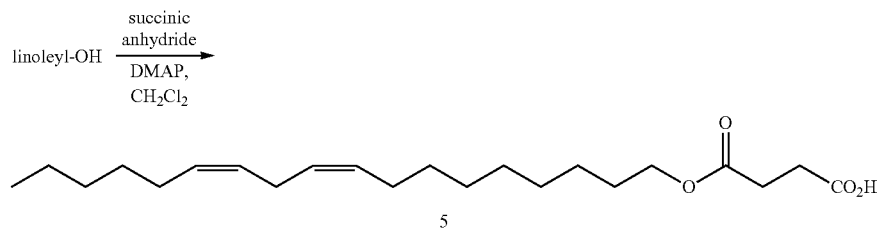

Compound 5: Linoleyl Hemisuccinate

Solid succinic anhydride (500 mg, 5.00 mmol, 2.00 equiv.) and DMAP (764 mg, 6.25 mmol, 2.50 equiv.) were added to a stirring, room temperature $CH_2Cl_2$ (10 mL) solution of linoleyl alcohol (666 mg, 2.50 mmol) in a round bottom flask under argon. After 14 h, the reaction mixture was diluted with $CH_2Cl_2$, washed with aq. 1 M HCl (2×10 mL), dried over $Na_2SO_4$ and concentrated on a rotary evaporator to afford hemisuccinate 5 (915 mg, quantitative yield) as a white semisolid that was used without further purification.

SCHEME 4: Scheme for synthesis of Lipid 10, 2,3-dilinoleoyl-4-dimethylamino-1,2,3-propanetriol.

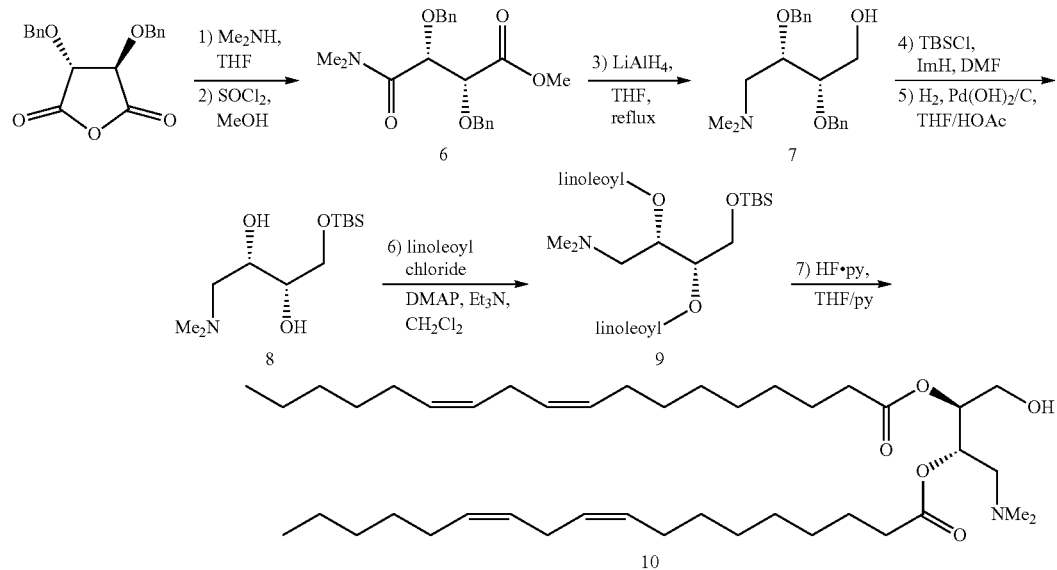

Compound 6: methyl (2R,3R)-2,3-bis(benzyloxy)-4-(dimethylamino)—4-oxobutanoate A $Me_2NH$/THF solution (22.5 mL of 2.0 M in THF, 45.0 mmol, 3.00 equiv.) was added over 5 min to a stirring, ice-cold THF (30 mL) solution of (3R,4R)-bis(benzyloxy)succinanhydride [Ohwada et al. (1990)] (4.68 g, 15.0 mmol) in a round bottom flask under argon. After 16 h, the reaction mixture was diluted with $Et_2O$ and quenched with saturated aq. $NH_4Cl$. The aqueous layer was extracted with $Et_2O$ (1×25 mL), the combined organic extracts were washed with brine, dried over $Na_2SO_4$ and concentrated on a rotary evaporator to afford the intermediate amidoacid as a viscous, yellow oil (5.36 g theoretical yield).

Thionyl chloride (1.14 mL, 15.7 mmol, 1.05 equiv.) was added to a stirring, ice-cold MeOH (25 mL) solution of the amidoacid in a round bottom flask under argon and the mixture was allowed to warm up. After 14 h, the volatiles were removed on a rotary evaporator and saturated aq. $NaHCO_3$ was added. The mixture was extracted with $Et_2O$ (2×75 mL), the combined organic extracts were washed with saturated aq. $NaHCO_3$ (1×100 mL), dried over $Na_2SO_4$ and concentrated on a rotary evaporator to afford the crude as a yellow oil. The crude was purified by flash column chromatography (220 mL $SiO_2$, 60:40 EtOAc/hexanes) to afford a pale, yellow oil as amidoester 6 (4.44 g, 80% yield).

$^1$H NMR (300 MHz, $CDCl_3$): δ 7.43-7.19 (m, 10H), 4.84 (d, J=11.6, 1H), 3.68 (s, 3H), 3.02 (s, 3H, rotamers), 2.91 (s, 3H, rotamers);

$^1$NMR (300 MHz, $CDCl_3$): δ 170.1, 168.5, 137.1, 136.7, 128.3, 128.2, 128.1, 127.9, 80.1, 78.9, 73.5, 72.4, 52.1, 36.9, 36.4.

Compound 7: (2S,3S)-2,3-bis(benzyloxy)-4-(dimethylamino)butan-1-ol

A THF (15 mL) solution of amidoester 6 (2.26 g, 6.08 mmol) was added over 1 h from an addition funnel to a refluxing THF (20 mL) suspension of $LiAlH_4$ (1.15 g, 30.4 mmol, 5.00 equiv.) in a two-necked round bottom flask fitted with a condenser and under argon. After an additional 5 min, the reaction mixture was cooled in an ice bath, diluted with Et$_2$O, quenched by the Fieser method [Fieser and Fieser (1967)] (1.2 mL water, 1.2 mL aq. 1 M NaOH, 3.6 ml water), then removed from the ice bath and stirred at room temperature until the precipitates turned white (~1 h). The mixture was filtered through Celite and the filtrate concentrated on a rotary evaporator to afford a clear, colourless oil as desired aminoalcohol 7 (1.99 g, 99% yield), which was used without further purification.

$^1$H NMR (300 MHz, CDCl$_3$): δ 7.41-7.24 (m, 10H), 6.04 (br s, 1H), 4.73 (d, J=11.7, 1H), 4.64 (d, J=11.7, 1H), 4.64 (s, 2H), 3.74 (hr d, J=3.6, 2H), 3.70 (dt, J=6.9, 3.3, 1H), 3.62-3.55 (m, 1H), 2.61 (dd, J=13.2, 6.9, 1H), 2.51 (dd, J=13.3, 3.3, 1H), 2.30 (s, 6H);

$^{13}$C NMR (300 MHz, CDCl$_3$): δ 138.5, 138.2, 128.33, 128.29, 127.81, 127.76, 127.6, 127.5, 81.7, 79.2, 72.6, 72.2, 60.1, 59.0, 46.0.

Compound 8: (2S,3S)-1-(tert-butyl)dimethylsilyl-4-dimethylaminobutane-1,2,3-triol Solid TBSCl (497 mg, 3.30 mmol, 1.10 equiv.) was added to a stirring, room temperature DMF (6 mL) solution of primary alcohol 7 (1.00 g, 3.00 mmol) and imidazole (449 mg, 6.60 mmol, 2.20 equiv.) in a round bottom flask under argon. After 14 h, the reaction mixture was quenched with aq. 5% NaHCO$_3$ (25 mL) and extracted with Et$_2$O (3×20 mL). The combined organic extracts were washed with water (3×20 mL), brine, dried over Na$_2$SO$_4$ and concentrated on a rotary evaporator to afford the crude as a clear, colourless oil. The crude was purified by flash column chromatography (100 mL SiO$_2$, 70:30:0→55:40:5 hexanes/EtOAc/MeOH) to afford a clear, colourless oil as the intermediate silyl ether (1.17 g, 87% yield).

Solid Pd(OH)$_2$/C (177 mg of 10 wt % stock, 0.12 mmol, 0.10 equiv.) was added to a stirring, room temperature 7:3 THF/HOAc (8.5 mL) solution of the above O-TBS bisbenzylated triol (558 mg, 1.26 mmol) in a round bottom flask under argon. The argon balloon was replaced with a hydrogen balloon and hydrogen gas was bubbled through the mixture for 5 min, before allowing it to stir under balloon pressure hydrogen for 18 h. The mixture was diluted with EtOAc and filtered through Celite. The pH of the filtrate was raised to pH 8-10 by the addition of saturated aq. Na$_2$CO$_3$, extracted with EtOAc (2×10 mL), then the combined organic extracts were washed with brine, dried over Na$_2$SO$_4$ and concentrated to obtain a clear, colourless oil as desired diol 8 (230 mg, 331 mg theoretical yield), which was used without further purification.

$^1$H NMR (300 MHz, CDCl$_3$): δ 3.85-3.76 (m, 1H), 3.72 (dd, J=5.9, 2.7, 2H), 3.55 (dt, J=5.7, 2.5, 1H), 3.31 (br s, 2H), 2.60 (dd, J=12.4, 8.8, 1H), 2.37-2.28 (m, 1H), 2.29 (s, 6H), 0.89 (s, 9H), 0.08 (s, 6H);

$^{13}$C NMR (300 MHz, CDCl$_3$): δ 72.3, 67.4, 64.9, 62.0, 45.8, 25.8, 18.2, −5.46.

Compound 9: (2S,3S)-1-(tert-butybdimethylsilyl-2,3-dilinoleoyl-4-dimethylaminobutane-1,2,3-triol A portion of diol 8 was used in the subsequent acylation. Linoleyl chloride was prepared by adding oxalyl chloride (0.19 mL, 2.25 mmol) to a stirring, room temperature benzene (5 mL) solution of linoleic acid (422 mg, 1.50 mmol, 2.20 equiv. relative to diol) and DMF (12 μL, 0.15 mmol) in a round bottom flask under argon. After 4 h, the volatiles were removed on a rotary evaporator and the residue azeotroped with benzene (2×5 mL), then dried under high vacuum for 3 h and used immediately without further purification. A CH$_2$Cl$_2$ (1.5 mL) solution of the above diol (180 mg, 0.68 mmol, 1.00 equiv.) and Et$_3$N (0.47 mL, 3.42 mmol, 5.00 equiv.) was added to a stirring, ice-cold CH$_2$Cl$_2$ (2 mL) solution of the linoleyl chloride in a round bottom flask under argon, followed by solid DMAP (184 mg, 1.50 mmol, 2.20 equiv.). The reaction mixture was allowed to warm up over 14 h, was then diluted with CH$_2$Cl$_2$, washed with aq. 5% NaHCO$_3$ (2×10 mL), dried over Na$_2$SO$_4$ and concentrated on a rotary evaporator to afford the crude as a yellow semi-solid. The crude was purified by flash column chromatography (50 mL SiO$_2$, 90:10 hexanes/EtOAc) to afford a clear, colourless oil as desired diester 9 (319 mg, 59% yield).

$^1$H NMR (300 MHz, CDCl$_3$): δ 5.46-5.22 (m, 9H), 5.18-5.09 (m, 1H), 3.66 (dd, J=5.6, 1.3, 2H), 2.77 (t, J=5.8, 4H), 2.49-2.26 (m, 6H), 2.22 (s, 6H), 2.05 (app q, J=13.0, 6.6, 8H), 1.70-1.47 (m, 6H), 1.44-1.19 (m, 27H), 0.94-0.84 (m, 6H), 0.87 (s, 9H), 0.03 (s, 6H);

$^{13}$C NMR (300 MHz, CDCl$_3$): δ 173.0, 172.9, 130.2, 130.0, 128.0, 127.8, 72.9, 69.0, 61.3, 59.3, 45.9, 34.33, 34.28, 31.5, 29.6, 29.3, 29.21, 29.19, 29.12, 29.07, 27.2, 25.7, 25.6, 25.0, 22.5, 18.1, 14.0, −5.6.

Compound 10: (2S,3S)-2,3-dilinoleoyl-4-dimethyl-aminobutane-1,2,3-triol

Neat HF.pyridine solution (87 μL of 70% HF in pyridine, 0.70 mmol, 3.00 equiv.) was added to a stirring, 10° C. THF (1.2 mL) solution containing pyridine (57 μL, 0.70 mmol, 3.00 equiv.) and silyl ether 9 (185 mg, 0.23 mmol) in a round bottom flask under argon. After 20 min, the reaction mixture was transferred to an ice bath, stirred for a further 2 h, then quenched with aq. 5% NaHCO$_3$. The mixture was extracted with EtOAc (3×5 mL), then the combined organic extracts were washed with brine, dried over Na$_2$SO$_4$ and concentrated on a rotary evaporator to afford a pale yellow oil as desired primary alcohol 10 (quantitative yield) that was used immediately without further purification. It should be noted that complete transesterification to the primary alcohol was observed (1H NMR, TLC) in <24 h when stored neat at 20° C.

SCHEME 5: Scheme for synthesis of Lipid 13, 4-linoleoyloxybutane-1-thiol.

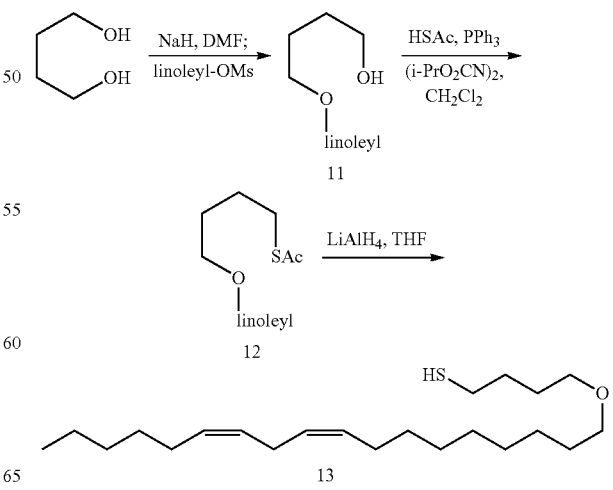

Compound 11: 4-(linoleyloxy)butan-1-ol

A DMF (1 mL) solution of 1,4-butanediol (135 mg, 1.50 mmol, 1.20 equiv.) was added to a stirring, ice-cold DMF (3 mL) suspension of NaH (80 mg, 2.50 mmol, 1.50 equiv.; previously washed with hexanes, 2×3 mL) in a round bottom flask under argon. The cold bath was then removed and the mixture stirred for 30 min. It was then cooled again in an ice bath and a DMF (1 mL) solution of linoleyl methanesulfonate (345 mg, 1.00 mmol) was added, allowing the mixture to warm up over 15 h. The reaction mixture was quenched by addition of water (10 mL), extracted with $Et_2O$ (3×5 mL), then the combined extracts were washed with water (3×5 mL), dried over $Na_2SO_4$ and concentrated on a rotary evaporator to afford the crude as a pale yellow oil. It was evident by $^1H$ NMR that some (~25%) olefin isomerization had occurred during the reaction and attempts to mitigate or eliminate this were unsuccessful. The crude was purified by flash column chromatography (50 mL $SiO_2$, 80:20 hexanes/EtOAc) to afford a clear, colourless oil as desired ether 11 (276 mg, 82% yield, 3:1 mixture of desired/isomerized).

$^1H$ NMR (300 MHz, $CDCl_3$): δ 5.49-5.22 (m, 4H), 3.65 (t, J=5.7, 2H), 3.5-3.38 (m, 4H), 2.79 (t, J=5.9, 2H), 2.06 (q, J=6.4, 4H), 1.76-1.62 (m, 4H), 1.65-1.51 (m, 2H), 1.46-1.18 (m, 17H), 0.90 (t, J=6.5, 3H);

$^{13}C$ NMR (300 MHz, $CDCl_3$): δ 130.15, 130.10, 127.93, 127.90, 71.2, 70.8, 62.7, 31.5, 30.4, 29.62, 29.59, 29.43, 29.41, 29.3, 29.23, 29.18, 27.19, 27.16, 27.0, 26.1, 25.6, 22.5, 14.0.

Compound 12: S-(4-linoleyloxybutyl) thioacetate

Neat diisopropyl azodicarboxylate (0.59 mL, 3.00 mmol, 2.00 equiv.) was added to a stirring, ice-cold THF (6 mL) solution of $Ph_3P$ (787 mg, 3.00 mmol, 2.00 equiv.) in a round bottom flask under argon, which resulted in the formation of an off-white precipitate, and the resultant was stirred for 1 h. A THF (2 mL) solution of thioacetic acid (0.21 mL, 3.00 mmol, 2.00 equiv.) and alcohol S10 (508 mg, 1.50 mmol) was then added to the above ice-cold mixture, which was allowed to warm to room temperature. After 16 h, the volatiles were removed on a rotary evaporator. The residue was resuspended in 80:20 hexanes/EtOAc, stirred for 15 min, at which point the white solids were removed by filtration through Celite and the filtrate concentrated on a rotary evaporator to afford the crude as a yellow oil. The crude was purified by flash column chromatography (80 mL $SiO_2$, 99:1→95:5 hexanes/EtOAc) to afford a clear, colourless oil as desired thioacetate 12 (549 mg, 92% yield).

$^1H$ NMR (300 MHz, $CDCl_3$): δ 5.47-5.24 (m, 4H), 3.49-3.12 (m, 4H), 2.98-2.86 (m, 2H), 2.78 (t, J=6.1, 2H), 2.33 (s, 3H), 2.06 (q, J=6.3, 4H), 1.75-1.61 (m, 4H), 1.63-1.48 (m, 2H), 1.46-1.18 (m, 17H), 0.90 (t, J=6.5, 3H).

Compound 13: 4-(linoleyloxy)butane-1-thiol

A THF (1 mL) solution of thioacetate 12 (119 mg, 0.30 mmol) was added dropwise to a stirring, ice-cold THF (2 mL) suspension of $LiAlH_4$ (46 mg, 1.20 mmol, 4.00 equiv.) in a round bottom flask under argon, which was allowed to warm up over time. After 4.5 h, the reaction was cooled in an ice bath, diluted with $Et_2O$ and quenched with aq. 1 M HCl (3 mL). The aqueous layer was extracted with $Et_2O$ (2×5 mL), then the combined extracts were washed with brine (1×5 mL), dried over $Na_2SO_4$ and concentrated on a rotary evaporator to afford a clear, colourless oil as desired thiol 13 (101 mg, 95% yield) that was used immediately and without further purification.

SCHEME 6: Scheme for synthesis of Lipid 16, oleyl hemisuccinate.

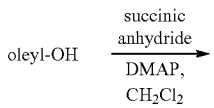

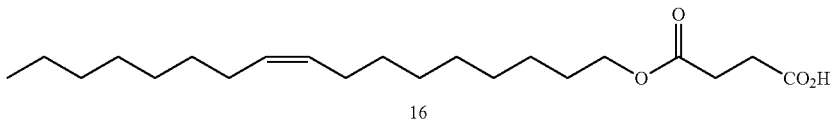

16

Compound 16: Oleyl Hemisuccinate

Solid succinic anhydride (200 mg, 2.00 mmol, 2.00 equiv.) and DMAP (305 mg, 2.50 mmol, 2.50 equiv.) were added to a stirring, room temperature $CH_2Cl_2$ (5 mL) solution of palmityl alcohol (268 mg, 1.00 mmol) in a round bottom flask under argon. After 14 h, the reaction mixture was diluted with $CH_2Cl_2$, washed with aq. 1 M HCl (2×10 mL), dried over $Na_2SO_4$ and concentrated on a rotary evaporator to afford hemisuccinate 16 (385 mg, quantitative yield) as a white semisolid that was used without further purification.

$R_f$ 0.22 ($SiO_2$, 70:30 hexanes/EtOAc).

SCHEME 7: Scheme for synthesis of Lipid 17, palmityl hemisuccinate.

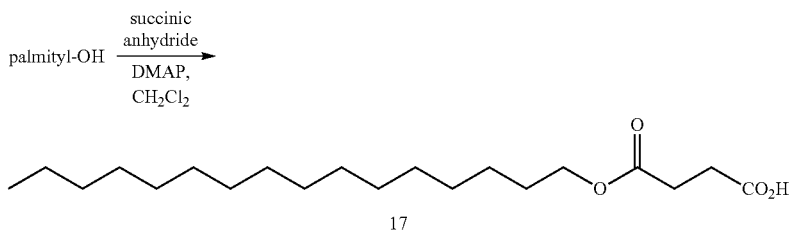

Compound 17: Palmityl Hemisuccinate

Solid succinic anhydride (200 mg, 2.00 mmol, 2.00 equiv.) and DMAP (305 mg, 2.50 mmol, 2.50 equiv.) were added to a stirring, room temperature $CH_2Cl_2$ (5 mL) solution of palmityl alcohol (242 mg, 1.00 mmol) in a round bottom flask under argon. After 14 h, the reaction mixture was diluted with $CH_2Cl_2$, washed with aq. 1 M HCl (2×10 mL), dried over $Na_2SO_4$ and concentrated on a rotary evaporator to afford hemisuccinate 17 (355 mg, quantitative yield) as a white semisolid that was used without further purification.

$R_f$ 0.15 ($SiO_2$, 70:30 hexanes/EtOAc).

SCHEME 8: Scheme for synthesis of Lipid 19, 2,3-dimyristoyl glycerol hemisuccinate.

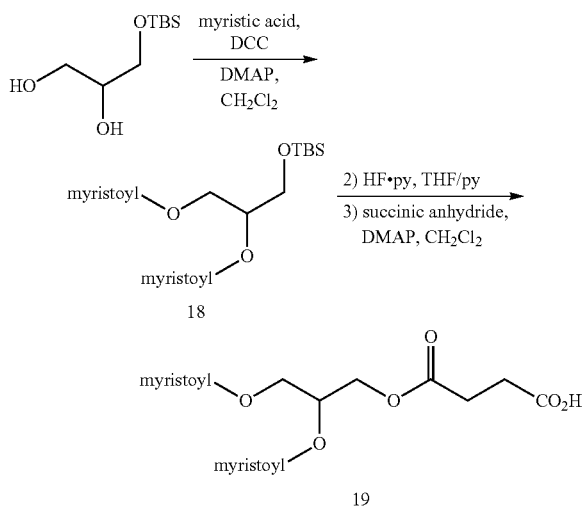

Compound 18: 1-(tert-butyl)dimethylsilyl-2,3-dimyristoyl glycerol

DCC (1.36 g, 6.60 mmol, 2.20 equiv.) was added to an ice-cold $CH_2Cl_2$ (15 mL) suspension of 1-(tert-butyl)dimethylsilyl glycerol (619 mg, 3.00 mmol) and myristic acid (1.51 g, 6.60 mmol, 2.20 equiv.) in a round bottom flask under argon, followed by DMAP (806 mg, 6.60 mmol, 2.20 equiv.) and the reaction mixture was allowed to warm to room temperature over 14 h. The reaction mixture was diluted with EtOAc, filtered through Celite and concentrated on a rotary evaporator. The crude was suspended in 80:20 hexanes/EtOAc and filtered through $SiO_2$ (40 mL) to afford a clear, colourless oil as diester 18 (1.91 g, quantitative yield).

$R_f$ 0.79 ($SiO_2$, 80:20 hexanes/EtOAc); $^1H$ NMR (300 MHz, $CDCl_3$): δ5.13-5.04 (m, 1H), 4.36 (dd, J=11.8, 3.8 Hz, 1H), 4.17 (dd, J=11.9, 6.2 Hz, 1H), 3.73 (d, J=5.5 Hz, 2H), 2.32 (t, J=7.3 Hz, 4H), 1.69-1,56 (m, 4H), 1.27 (br s, 40H), 0.90 (br s, 15H), 0.07 (s, 6H).

Compound 19: 2,3-dimyristoyl glycerol hemisuccinate

Neat HF.pyridine solution (1.13 mL of 70% HF in pyridine, 9.14 mmol, 3.00 equiv.) was added to a stirring, ice-cold THF (12 mL) solution containing pyridine (0.74 mL, 9.14 mmol, 3.00 equiv.) and silyl ether 18 (1.91 g, 3.04 mmol) in a round bottom flask under argon, then allowed to warm to room temperature. After 5 h, the reaction mixture was neutralized with saturated aq. $NaHCO_3$ and extracted with $Et_2O$ (3×25 mL). The combined organic extracts were washed with $H_2O$ (1×25 mL), brine (1×25 mL), dried over $Na_2SO_4$ and concentrated on a rotary evaporator. The crude was purified by flash column chromatography (100 mL $SiO_2$, 80:20 hexanes/EtOAc) to afford a white solid as the intermediate alcohol (1.31 g, 84% yield).

$R_f$=0.26 ($SiO_2$, 80:20 hexanes/EtOAc);

$^1H$ NMR (300 MHz, $CDCl_3$): δ 5.10 (quin, J=5.0 Hz, 1H), 4.34 (dd, J=11.9, 4.6 Hz, 1H), 4.25 (dd, J=11.9, 5.6 Hz, 1H), 3.74 (t, J=5.4 Hz, 2H), 2.35 (q, J=7.3 Hz, 4H), 2.10 (br s, 1H), 1.63 (br s, 4H), 1.27 (br s, 40H), 0.90 (br t, J=6.3 Hz, 6H).

A portion of the above alcohol (513 mg, 1.00 mmol) was dissolved in $CH_2Cl_2$ (3 mL) in a round bottom flask under argon and cooled in an ice bath. Succinic anhydride (200 mg, 2.00 mmol, 2.00 equiv.) and DMAP (305 mg, 2.50 mmol, 2.50 equiv.) were sequentially added and the mixture was allowed to warm to room temperature over 14 h. The reaction mixture was diluted with $CH_2Cl_2$, washed with aq. 1 M HCl (3×10 mL), dried over $Na_2SO_4$ and concentrated on a rotary evaporator to afford a white solid as hemisuccinate 19 (608 mg, quantitative yield) that was used without further purification.

$R_f$=0.18 ($SiO_2$, 50:50 hexanes/EtOAc).

SCHEME 9: Scheme for synthesis of Lipid 21, 2,3-dioleoyl glycerol hemisuccinate.

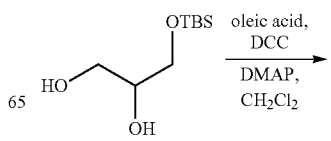

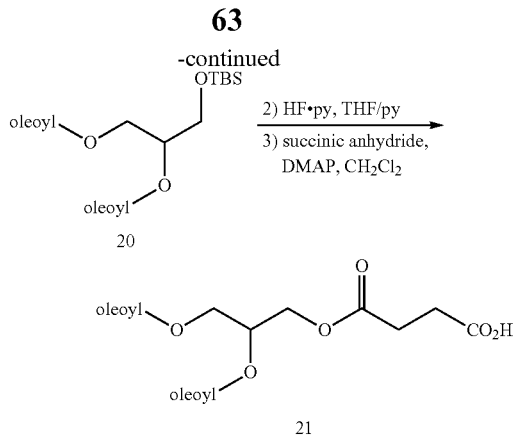

Compound 20: 1-(tert-butyl)dimethylsilyl-2,3-dioleoyl glycerol

DCC (1.36 g, 6.60 mmol, 2.20 equiv.) was added to an ice-cold $CH_2Cl_2$ (10 mL) solution of 1-(tert-butyl)dimethylsilyl glycerol (619 mg, 3.00 mmol) and oleic acid (1.86 g, 6.60 mmol, 2.20 equiv.) in a round bottom flask under argon, followed by DMAP (806 mg, 6.60 mmol, 2.20 equiv.) and the reaction mixture was allowed to warm to room temperature over 14 h. The reaction mixture was diluted with $Et_2O$, filtered through Celite and concentrated on a rotary evaporator. The crude was suspended in 95:5 hexanes/EtOAc and filtered through $SiO_2$ (40 mL) to afford a clear, colourless oil as diester 20 (2.04 g, 93% yield).

$R_f$ 0.84 ($SiO_2$, 80:20 hexanes/EtOAc); $^1$H NMR (300 MHz, $CDCl_3$): δ 5.44-5.28 (m, 4H), 5.14-5.03 (m, 1H), 4.36 (dd, J=11.9, 3.8 Hz, 1H), 4.17 (dd, J=11.9, 6.3 Hz, 1H), 3.73 (d, J=5.4 Hz, 2H), 2.32 (t, J=7.7 Hz, 4H), 2.11-1.93 (m, 8H), 1.71-1.56 (m, 4H), 1.42-1.22 (m, 40H), 0.90 (br s, 15H), 0.07 (s, 6H).

Compound 21: 2,3-dioleoyl glycerol hemisuccinate

Neat HF.pyridine solution (0.72 mL of 70% HF in pyridine, 5.05 mmol, 3.00 equiv.) was added to a stirring, ice-cold THF (8 mL) solution containing pyridine (0.41 mL, 5.05 mmol, 3.00 equiv.) and silyl ether 20 (1.24 g, 1.68 mmol) in a round bottom flask under argon, then allowed to warm to room temperature. After 4 h, the reaction mixture was neutralized with saturated aq. $NaHCO_3$ and extracted with $Et_2O$ (3×10 mL). The combined organic extracts were washed with $H_2O$ (1×25 mL), brine (1×25 mL), dried over $Na_2SO_4$ and concentrated on a rotary evaporator to afford a clear, colourless oil as the intermediate alcohol (1.08 g, quantitative yield).

$R_f$=0.39 ($SiO_2$, 80:20 hexanes/EtOAc);

$^1$H NMR (300 MHz, $CDCl_3$): δ 5.47-5.27 (m, 4H), 5.10 (quin, J=5.0 Hz, 1H), 4.34 (dd, J=12.0, 4.7 Hz, 1H), 4.25 (dd, J=11.9, 5.6 Hz, 1H), 3.75 (t, J=5.0 Hz, 2H), 2.35 (q, J=7.4 Hz, 4H), 2.12-1.93 (m, 8H), 1.73-1.52 (m, 4H), 1.43-1.19 (m, 40H), 0.90 (br t, J=7.1 Hz, 6H).

A portion of the above alcohol (714 mg, 1.15 mmol) was dissolved in $CH_2Cl_2$ (6 mL) in a round bottom flask under argon and cooled in an ice bath. Succinic anhydride (230 mg, 2.30 mmol, 2.00 equiv.) and DMAP (351 mg, 2.87 mmol, 2.50 equiv.) were sequentially added and the mixture was allowed to warm to room temperature over 14 h. The reaction mixture was diluted with $CH_2Cl_2$, washed with aq. 1 M HCl (3×10 mL), dried over $Na_2SO_4$ and concentrated on a rotary evaporator to afford a clear, colourless oil as hemisuccinate 21 (696 mg, 84% yield) that was used without further purification.

$R_f$=0.22 ($SiO_2$, 50:50 hexanes/EtOAc).

Procedures for Synthesis of Drug Conjugates

SCHEME 10: Scheme for synthesis of $LD_{01}$-DEX, dexamethasone-21-[4-(3-(dimethylamino)-2-((linoleoyloxy)propoxy)-4-oxobutanoate.

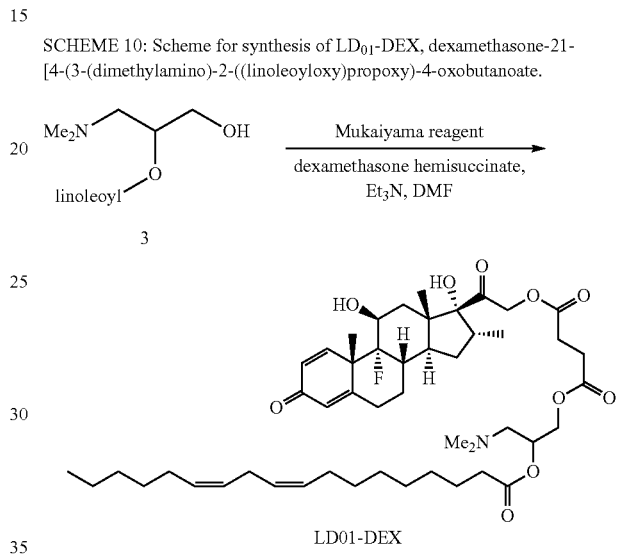

LD01-DEX: Dexamethasone 21-[4-(3-(dimethylamino)-2-((linoleoyloxy)propoxy)-4-oxobutanoate]

Solid dexamethasone 21-hemisuccinate[i] (45 mg, 0.18 mmol, 0.50 equiv.) was added to a room temperature DMF (1 mL) solution of primary alcohol 3 (68 mg, 0.18 mmol, 2.00 equiv.) and $Et_3N$ (38 μL, 0.27 mmol, 1.50 equiv.) in a round bottom flask under argon, followed by 2-chloro-1-methylpyridinium iodide (28 mg, 0.11 mmol, 0.60 equiv.). After 14 h, the mixture was quenched with aq. 5% $NaHCO_3$. The mixture was extracted with EtOAc (2×3 mL), then the combined organic extracts were washed with aq. 5% $NaHCO_3$ (1×3 mL), brine, dried over $Na_2SO_4$ and concentrated on a rotary evaporator to afford the crude as a yellow oil. The crude was purified by flash column chromatography (20 mL $SiO_2$, 97:3 $CHCl_3$/MeOH) to afford a clear, colourless oil as desired conjugate LD01-DEX (72 mg, 94% yield).

$R_f$=0.48 ($SiO_2$, 90:10 $CHCl_3$/MeOH);

$^1$H NMR (300 MHz, $CDCl_3$): δ 7.20 (d, J=10.2 Hz, 1H), 6.31 (d, J=10.2 Hz, 1H), 6.09 (s, 1H), 5.48-5.25 (m, 4H), 5.24-5.12 (m, 1H), 4.96 (dd, J=12.0, 6.6 Hz, 1H), 4.83 (dd, J=12.0, 6.6 Hz, 1H), 4.48-4.24 (m, 2H), 4.22-3.97 (m, 1H), 3.08 (m, 2H), 2.85-2.70 (m, 4H), 2.75-2.40 (m, 6H), 2.44-2.18 (m, 12H), 2.20-1.93 (m, 6H), 1.90-1.45 (m, 7H), 1.53 (s, 3H), 1.43-1.24 (m, 18H), 1.02 (s, 3H), 0.93-0.80 (m, 6H).

SCHEME 11: Scheme for synthesis of LD$_{02}$-DEX, 2,3-dilinoleoyloxypropyl (2-((8S,9R,10S,11S,13S,14S,16R,17R)-9-fluoro-11,17-dihydroxy-10,13,16-trimethyl-3-oxo-6,7,8,9,10,11,12,13,14,15,16,17-dodecahydro-3H-cyclopenta[a]phenanthren-17-yl)-2-oxoethyl) succinate.

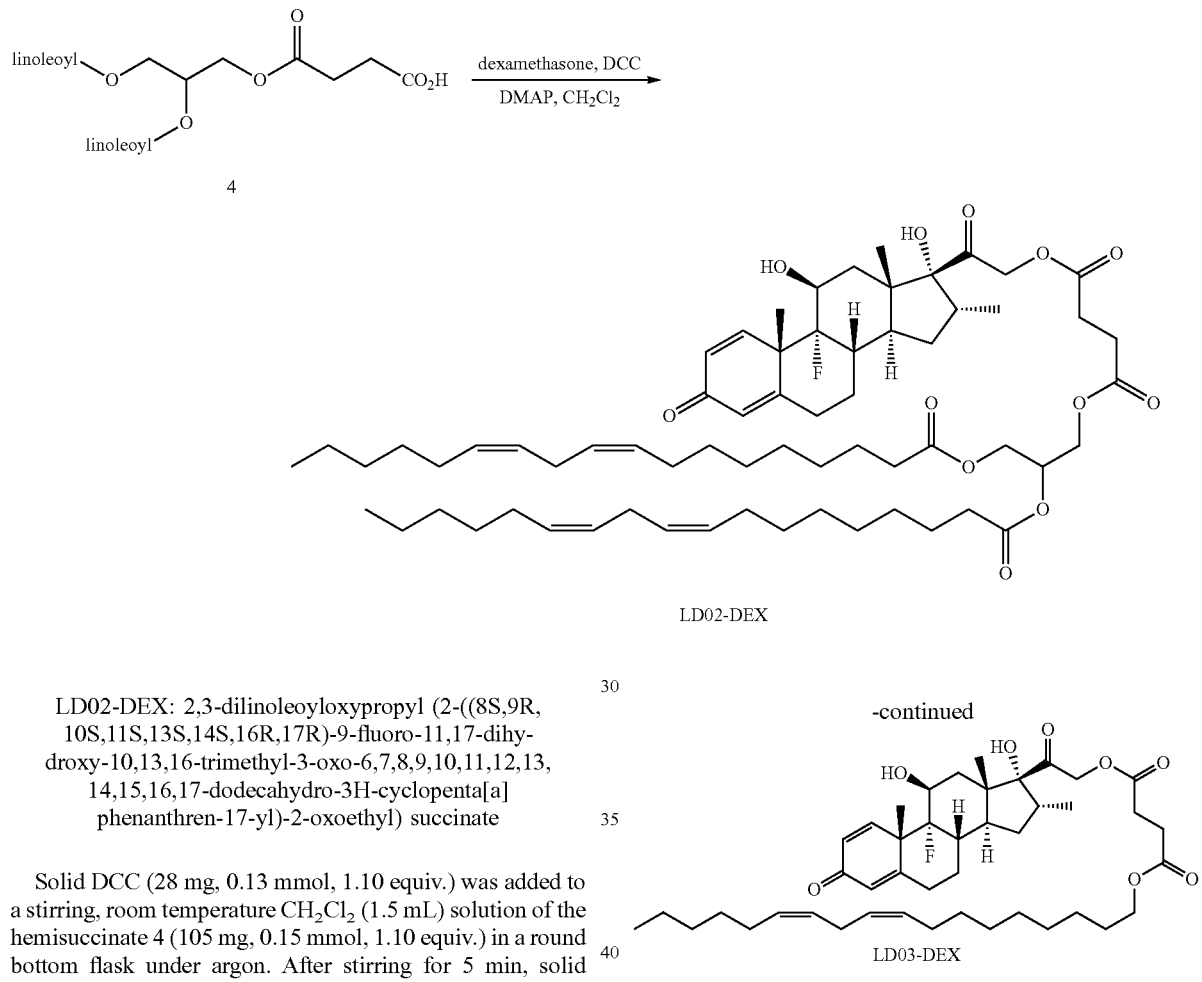

LD02-DEX: 2,3-dilinoleoyloxypropyl (2-((8S,9R, 10S,11S,13S,14S,16R,17R)-9-fluoro-11,17-dihydroxy-10,13,16-trimethyl-3-oxo-6,7,8,9,10,11,12,13,14,15,16,17-dodecahydro-3H-cyclopenta[a]phenanthren-17-yl)-2-oxoethyl) succinate Solid DCC (28 mg, 0.13 mmol, 1.10 equiv.) was added to a stirring, room temperature $CH_2Cl_2$ (1.5 mL) solution of the hemisuccinate 4 (105 mg, 0.15 mmol, 1.10 equiv.) in a round bottom flask under argon. After stirring for 5 min, solid dexamethasone (52 mg, 0.13 mmol) and DMAP (24 mg, 0.20 mmol, 1.50 equiv.) were added. The reaction mixture was allowed to stir for 14 h, diluted with $CH_2Cl_2$, filtered through Celite and the filtrate was concentrated to afford the crude as a pale yellow oil. The crude was purified by flash column chromatography (25 mL $SiO_2$, 80:20→70:30→50:50 hexanes/EtOAc) to afford a clear, colourless oil as desired conjugate LD02-DEX (67 mg, 46% yield).

$^1$H NMR (300 MHz, CDCl$_3$): δ 7.22 (dd, J=10.2, 3.9, 1H), 6.32 (dd, J=10.2, 1.7, 1H), 6.1 (s, 1H), 5.44-5.17 (m, 9H), 5.00-4.81 (m, 2H), 4.43-4.22 (m, 4H), 4.21-4.06 (m, 2H), 3.16-3.01 (m, 1H), 2.84-2.51 (m, 11H), 2.50-2.23 (m, 9H), 2.21-1.48 (m, 25H), 1.45-1.15 (m, 34H), 1.14-1.00 (m, 1H), 1.03 (s, 3H), 0.95-0.81 (m, 10H).

SCHEME 12: Scheme for synthesis of LD03-DEX, linoleyl 2-((8S,9R,10S,11S,13S,14S,16R,17R)-9-fluoro-11,17-dihydroxy-10,13,16-trimethyl-3-oxo-6,7,8,9,10,11,12,13,14,15,16,17-dodecahydro-3H-cyclopenta[a]phenanthren-17-yl)-2-oxoethyl succinate.

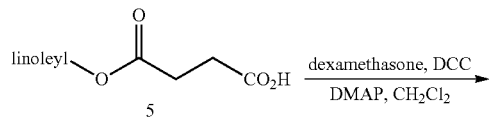

LD03-DEX: linoleyl 2-((8S,9R,10S,11S,13S,14S, 16R,17R)-9-fluoro-11,17-dihydroxy-10,13,16-trimethyl-3-oxo-6,7,8,9,10,11,12,13,14,15,16,17-dodecahydro-3H-cyclopenta[a]phenanthren-47-yl)-2-oxoethyl succinate Solid DCC (37 mg, 0.18 mmol, 1.10 equiv.) was added to a stirring, room temperature $CH_2Cl_2$ (1.6 mL) solution of hemisuccinate 5 (65 mg, 0.18 mmol, 1.10 equiv.) in a round bottom flask under argon. After stirring for 5 min, solid dexamethasone (63 mg, 0.16 mmol) and DMAP (30 mg, 0.24 mmol, 1.50 equiv.) were added. The reaction mixture was allowed to stir for 14 h, diluted with $CH_2Cl_2$, filtered through Celite and the filtrate was concentrated to afford the crude as a clear, colourless oil. The crude was purified by flash column chromatography (25 mL $SiO_2$, 70:30→60:40 hexanes/EtOAc) to afford a clear, colourless oil as desired conjugate LD03-DEX (76 mg, 64% yield).

$^1$H NMR (300 MHz, CDCl$_3$): δ 7.25 (d, J=10.2, 1H), 6.33 (d, J=10.1, 1H), 6.1 (s, 1H), 5.45-5.25 (m, 4H), 4.93 (s, 2H), 4.45-4.27 (m, 1H), 4.08 (t, J=6.7, 2H), 3.17-3.01 (m, 1H), 2.92 (s, 1H), 2.77 (t, J=6.5, 4H), 2.72-2.52 (m, 4H), 2.50-2.24 (m, 4H), 2.23-2.07 (m, 1H), 2.05 (q, J=6.6, 4H), 1.97-1.45 (m, 10H), 1.44-1.01 (m, 20H), 1.02 (s, 3H), 0.97-0.80 (m, 6H).

SCHEME 13: Scheme for synthesis of $LD_{06}$-DEX, (2S,3S)-4-(dimethylamino)-2,3-bis(linoleoyloxy)butyl (2-((8S,9R,10S,11S,13S,14S,16R,17R)-9-fluoro-11,17-dihydroxy-10,13,16-trimethyl-3-oxo-6,7,8,9,10,11,12,13,14,15,16,17-dodecahydro-3H-cyclopenta[a]phenanthren-17-yl)-2-oxoethyl) succinate.

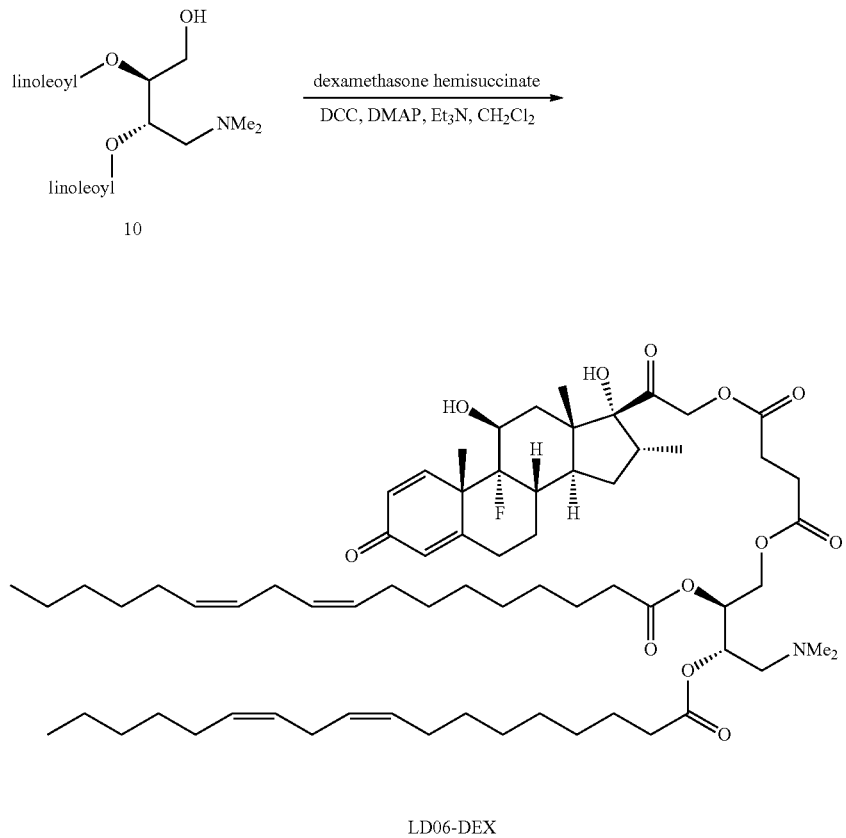

LD06-DEX $LD_{06}$-DEX: (2S,3S)-4-(dimethylamino)-2,3-bis(linoleoyloxy)butyl (2-((8S,9R,10S,11S,13S,14S,16R,17R)-9-fluoro-11,17-dihydroxy-10,13,16-trimethyl-3-oxo-6,7,8,9,10,11,12,13,14,15,16,17-dodecahydro-3H-cyclopenta[a]phenanthren-17-yl)-2-oxoethyl) succinate Solid dexamethasone-21-hemisuccinate [Mao et al. (2012)] (88 mg, 0.18 mmol, 1.10 equiv.) was added to a room temperature THF (0.8 mL) solution of DCC (37 mg, 0.18 mmol, 1.10 equiv.) in a round bottom flask under argon. After 10 min, the mixture was cooled in an ice bath, a THF (0.8 mL) solution of alcohol 10 (109 mg, 0.16 mmol), DMAP (22 mg, 0.18 mmol, 1.10 equiv.) and $Et_3N$ (25 uL, 0.18 mmol, 1.10 equiv.) was added and the mixture was allowed to warm up overnight. After 20 h, the reaction mixture was diluted with THF, filtered through Celite and concentrated on a rotary evaporator to afford the crude as a pale yellow semisolid. The crude was purified by flash column chromatography (50 mL $SiO_2$, 36:60:4 $Et_2O$/hexanes/MeOH) to afford a clear, colourless oil as desired conjugate LD06-DEX (103 mg, 55% yield).

$^1$H NMR (300 MHz, $CDCl_3$): δ 7.24 (d, J=10.1, 1H), 6.34 (d, J=10.1, 1H), 6.12 (s, 1H), 5.47-5.26 (m, 10H), 5.26-5.15 (m, 1H), 5.01 (d, J=17.5, 1H), 4.86 (d, J=17.5, 1H), 4.43-4.27 (m, 2H), 4.20-4.08 (m, 1H), 3.20-3.02 (m, 2.78 (app t, J=5.6, 7H), 2.70-2.60 (m, 2H), 2.60-2.5 (m, 18H), 2.24 (s, 6H), 2.18-2.03 (m, 3H), 2.06 (app q, J=13.1, 6.7, 8H), 1.90-1.49 (m, 13H), 1.47-1.16 (m, 39H), 1.05 (s, 3H), 0.90 (app t, J=6.7, 11H).

SCHEME 14: Scheme for synthesis of $LD_{07}$-DEX, (8S,9R,10S,11S,13S,14S,16R,17R)-9-fluoro-11,17-dihydroxy-10,13,16-trimethyl-17-(2-((4-(linoleyloxy)butyl)thio)acetyl)-6,7,8,9,10,11,12,13,14,15,16,17-dodecahydro-3H-cyclopenta[a]phenanthren-3-one.

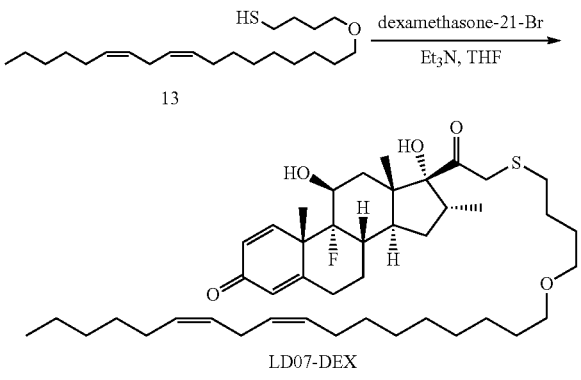

LD07-DEX

LD07-DEX: (8S,9R,10S,11S,13S,14S,16R,17R)-9-fluoro-11,17-dihydroxy-10,13,16-trimethyl-17-(2-((4-(linoleyloxy)butyl)thio)acetyl)-6,7,8,9,10,11,12,13,14,15,16,17-dodecahydro-3H-cyclopenta[a]phenanthren-3-one A THF (0.6 mL) solution of thiol 13 (66 mg, 0.19 mmol, 1.90 equiv.) was added to a stirring, ice-cold THF (0.4 mL) solution of dexamethasone-21-bromide [Lopez and Simons (1991)] (48 mg, 0.10 mmol) in a round bottom flask under argon. After 8 h, the reaction mixture was diluted with THF, filtered through Celite and concentrated on a rotary evaporator to afford the crude as a yellow oil. The crude was purified by flash column chromatography (25 mL SiO$_2$, 80:20→65:35 hexanes/EtOAc) to afford a clear, colourless oil as desired sulfide LD07-DEX (48 mg, 62% yield).

$^1$H NMR (300 MHz, CDCl$_3$): δ 7.18 (d, J=10.2, 1H), 6.32 (dd, J=10.1, 1.7, 1H), 6.11 (s, 1H), 5.47-5.23 (m, 4H), 4.34 (br d, J=10.0, 1H), 3.52 (d, J=13.4, 1H), 3.48-3.29 (m, 5H), 3.18 (d, J=13.2, 1H), 3.14-2.99 (m, 1H), 2.77 (t, J=6.0, 2H), 2.65 (s, 1H), 2.69-2.19 (m, 8H), 2.04 (q, J=6.5, 4H), 1.90-1.46 (m, 17H), 1.46-1.15 (m, 23H), 1.05 (s, 3H), 0.95-0.82 (m, 7H).

SCHEME 15: Scheme for synthesis of LD$_{13}$-DEX, oleyl 2-((8S,9R,10S,11S,13S,14S,16R,17R)-9-fluoro-11,17-dihydroxy-10,13,16-trimethyl-3-oxo-6,7,8,9,10,11,12,13,14,15,16,17-dodecahydro-3H-cyclopenta[a]phenanthren-17-yl)-2-oxoethyl succinate.

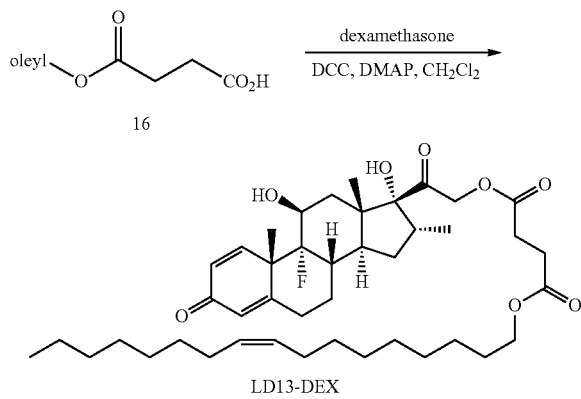

LD13-DEX: oleyl 2-((8S,9R,10S,11S,13S,14S,16R,17R)-9-fluoro-11,17-dihydroxy-10,13,16-trimethyl-3-oxo-6,7,8,9,10,11,12,13,14,15,16,17-dodecahydro-3H-cyclopenta[a]phenanthren-17-yl)-2-oxoethyl succinate Solid DCC (25 mg, 0.12 mmol, 1.20 equiv.) was added to a stirring, room temperature CH$_2$Cl$_2$ (1 mL) solution of hemisuccinate 16 (44 mg, 0.12 mmol, 1.20 equiv.) in a round bottom flask under argon. After stirring for 5 min, solid dexamethasone (39 mg, 0.10 mmol) and DMAP (18 mg, 0.15 mmol, 1.50 equiv.) were added. The reaction mixture was allowed to stir for 14 h, diluted with CH$_2$Cl$_2$, filtered through Celite and the filtrate was concentrated to afford the crude as a clear, colourless oil. The crude was purified by flash column chromatography (20 mL SiO$_2$, 60:40→50:50 hexanes/EtOAc) to afford a clear, colourless oil as desired conjugate LD13-DEX (50 mg, 67% yield).

$^1$H NMR (300 MHz, CDCl$_3$): δ 7.22 (d, J=9.7 Hz, 1H), 6.31 (dd, J=10.2, 1.8 Hz, 1H), 6.08 (s, 1H), 5.40-5.25 (m, 2H), 4.99-4.83 (m, 2H), 4.41-4.27 (m, 1H), 4.06 (t, J=6.8 Hz, 2H), 3.16-2.99 (m, 1H), 2.82 (br s, 1H), 2.79-2.69 (m, 2H), 2.68-2.58 (m, 3H), 2.49-2.24 (m, 4H), 2.22-2.06 (m, 1H), 2.06-1.92 (m, 4H), 1.94-1.46 (m, 10H), 1.40-1.08 (m, 22H), 1.01 (s, 3H), 0.95-0.78 (m, 6H).

SCHEME 16: Scheme for synthesis of LD14-DEX, palmityl 2-((8S,9R,10S,11S,13S,14S,16R,17R)-9-fluoro-11,17-dihydroxy-10,13,16-trimethyl-3-oxo-6,7,8,9,10,11,12,13,14,15,16,17-dodecahydro-3H-cyclopenta[a]phenanthren-17-yl)-2-oxoethyl succinate.

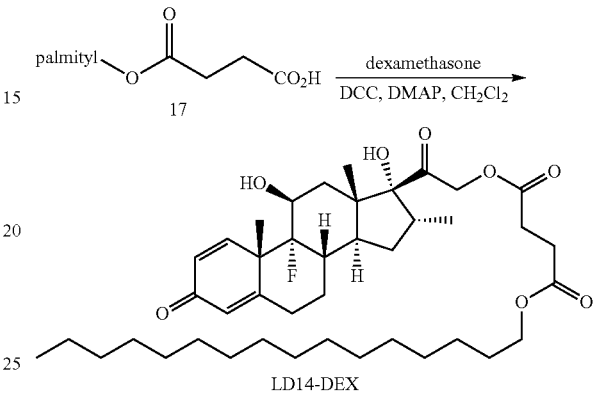

LD14-DEX: palmityl 2-((8S,9R,10S,11S,13S,14S,16R,17R)-9-fluoro-11,17-dihydroxy-10,13,16-trimethyl-3-oxo-6,7,8,9,10,11,12,13,14,15,16,17-dodecahydro-3H-cyclopenta[a]phenanthren-17-yl)-2-oxoethyl succinate Solid DCC (25 mg, 0.12 mmol, 1.20 equiv.) was added to a stirring, room temperature CH$_2$Cl$_2$ (1 mL) solution of hemisuccinate 16 (41 mg, 0.12 mmol, 1.20 equiv.) in a round bottom flask under argon. After stirring for 5 min, solid dexamethasone (39 mg, 0.10 mmol) and DMAP (18 mg, 0.15 mmol, 1.50 equiv.) were added. The reaction mixture was allowed to stir for 14 h, diluted with CH$_2$Cl$_2$, filtered through Celite and the filtrate was concentrated to afford the crude as a clear, colourless oil. The crude was purified by flash column chromatography (20 mL SiO$_2$, 60:40→50:50 hexanes/EtOAc) to afford a clear, colourless oil as desired conjugate LD14-DEX (43 mg, 60% yield).

$^1$H NMR (300 MHz, CDCl$_3$): δ 7.22 (d, J=10.0 Hz, 1H), 6.31 (dd, J=10.2, 1.8 Hz, 1H), 6.08 (s, 1H), 5.00-4.83 (m, 2H), 4.38-4.26 (m, 1H), 4.06 (t, J=6.8 Hz, 2H), 3.16-3.00 (m, 1H), 2.84 (br s, 1H), 2.80-2.70 (m, 2H), 2.69-2.53 (m, 3H), 2.48 (br s, 1H), 2.42-2.24 (m, 3H), 2.22-2.06 (m, 1H), 1.95-1.42 (m, 10H), 1.39-1.17 (m, 26H), 1.16-1.02 (m, 2H), 1.01 (s, 3H), 0.95-0.80 (m, 6H).

SCHEME 17: Scheme for synthesis of LD$_{17}$-DEX, 2,3-dimyristoylpropyl (2-((8S,9R,10S,11S,13S,14S,16R,17R)-9-fluoro-11,17-dihydroxy-10,13,16-trimethyl-3-oxo-6,7,8,9,10,11,12,13,14,15,16,17-dodecahydro-3H-cyclopenta[a]phenanthren-17-yl)-2-oxoethyl) succinate.

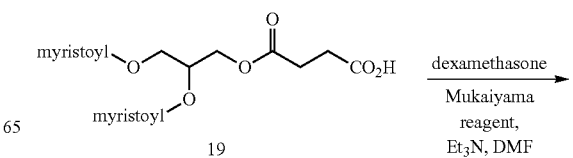

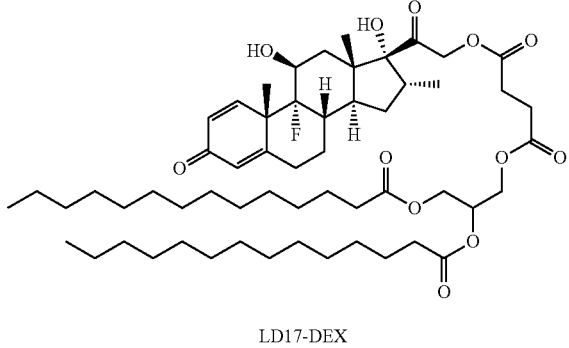

LD17-DEX

LD17-DEX: 2,3-dimyristroylpropyl (2-((8S,9R,10S,11S,13S,14S,16R,17R)-9-fluoro-11,17-dihydroxy-10,13,16-trimethyl-3-oxo-6,7,8,9,10,11,12,13,14,15,16,17-dodecahydro-3H-cyclopenta[a]phenanthren-17-yl)-2-oxoethyl) succinate Et$_3$N (53 µL, 0.20 mmol, 2.50 equiv.), followed by the Mukaiyama reagent (51 mg, 0.20 mmol, 1.30 equiv.), was added to an ice-cold CH$_2$Cl$_2$ (0.7 mL) solution of dexamethasone (76 mg, 0.15 mmol) and hemisuccinate 19 (92 mg, 0.18 mmol, 1.20 equiv.) in a dry round bottom flask under argon. The reaction mixture was allowed to warm up over 14 h, then diluted with EtOAc, washed with aq. 5% NaHCO$_3$ (1×5 mL), H$_2$O (2×5 mL), brine (1×5 mL), dried over Na$_2$SO$_4$ and concentrated on a rotary evaporator. The crude was purified by flash column chromatography (20 mL SiO$_2$, 80:20→50:50 hexanes/EtOAc) to afford a clear, colourless oil as desired conjugate LD17-DEX (72 mg, 47% yield).

R$_f$ 0.45 (SiO$_2$, 50:50 hexanes/EtOAc);

$^1$H NMR (300 MHz, CDCl$_3$): δ 7.23 (d, J=10.0 Hz, 1H), 6.33 (dd, J=10.2, 1.8 Hz, 1H), 6.11 (s, 1H), 5.30-5.17 (m, 1H), 5.07-4.83 (m, 2H), 4.45-4.08 (m, 5H), 3.19-3.03 (m, 1H), 2.85-2.49 (m, 7H), 2.47-2.25 (m, 7H), 2.23-2.07 (m, 1H), 1.96-1.54 (m, 8H), 1.38-1.15 (m, 43H), 1.04 (s, 3H), 0.98-0.79 (m, 9H).

SCHEME 18: Scheme for synthesis of LD$_{19}$-PDN, oleyl (2-((8S,9S,10R,13S,14S,17R)-17-hydroxy-10,13-dimethyl-3,11-dioxo-6,7,8,9,10,11,12,13,14,15,16,17-dodecahydro-3H-cyclopenta[a]phenanthren-17-yl)-2-oxoethyl) succinate.

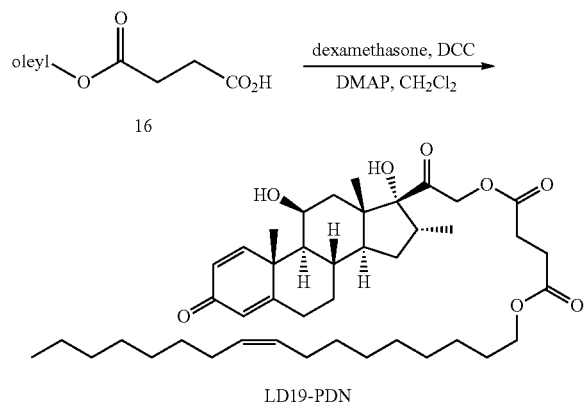

LD19-PDN

LD19-PDN: oleyl (2-((8S,9S,10R,13S,14S,17R)-17-hydroxy-10,13-dimethyl-3,11-dioxo-6,7,8,9,10,11,12,13,14,15,16,17-dodecahydro-3H-cyclopenta[a]phenanthren-17-yl)-2-oxoethyl)succinate Solid DCC (52 mg, 0.25 mmol, 1.20 equiv.) was added to a stirring, room temperature CH$_2$Cl$_2$ (1 mL) solution of hemisuccinate 16 (92 mg, 0.25 mmol, 1.20 equiv.) in a round bottom flask under argon. After stirring for 5 min, solid prednisone (75 mg, 0.21 mmol) and DMAP (38 mg, 0.31 mmol, 1.50 equiv.) were added. The reaction mixture was allowed to stir for 14 h, diluted with CH$_2$Cl$_2$, filtered through Celite and the filtrate was concentrated to afford the crude as a pale yellow oil. The crude was purified by flash column chromatography (25 mL SiO$_2$, 70:30→50:50 hexanes/EtOAc) to afford a clear, colourless oil as desired conjugate LD19-PDN (103 mg, 71% yield).

R$_f$ 0.52 (SiO$_2$, 75:25 EtOAc/hexanes);

$^1$H NMR (300 MHz, CDCl$_3$): δ 7.69 (d, J=10.1 Hz, 1H), 6.19 (dd, J=10.3, 1.8 Hz, 1H), 6.07 (s, 1H), 5.42-5.25 (m, 2H), 5.07 (d, J=17.1 Hz, 1H), 4.73 (d, J=17.5 Hz, 1H), 4.07 (t, J=6.7 Hz, 2H), 2.88 (d, J=12.2 Hz, 1H), 2.83-2.69 (m, 3H), 2.69-2.59 (m, 2H), 2.51 (dt, J=13.1, 4.3 Hz, 1H), 2.44-2.26 (m, 3H), 2.14-1.83 (m, 7H), 1.76-1.55 (m, 4H), 1.43 (s, 3H), 1.38-1.16 (m, 25H), 1.16-0.98 (m, 1H), 0.87 (br t, J=6.6 Hz, 3H), 0.67 (s, 3H).

SCHEME 19: Scheme for synthesis of LD$_{20}$-PDL, oleyl 2-((8S,9S,10R,11S,13S,14S,17R)-11,17-dihydroxy-10,13-dimethyl-3-oxo-6,7,8,9,10,11,12,13,14,15,16,17-dodecahydro-3H-cyclopenta[a]phenanthren-17-yl)-2-oxoethyl succinate.

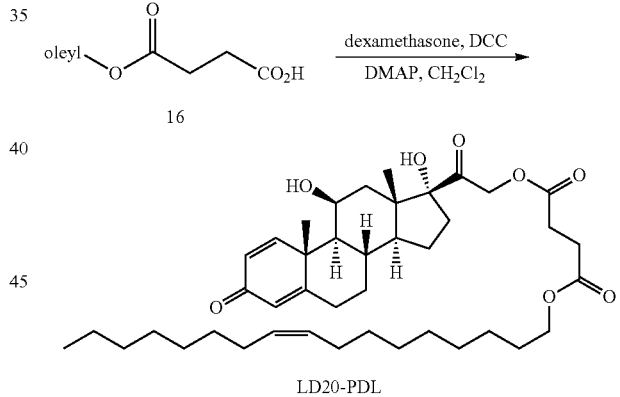

LD20-PDL

LD20-PDL: oleyl 2-((8S,9S,10R,11S,13S,14S,17R)-11,17-dihydroxy-10,13-dimethyl-3-oxo-6,7,8,9,10,11,12,13,14,15,16,17-dodecahydro-3H-cyclopenta[a]phenanthren-17-yl)-2-oxoethyl succinate Solid DCC (74 mg, 0.36 mmol, 1.20 equiv.) was added to a stirring, room temperature CH$_2$Cl$_2$ (2 mL) solution of hemisuccinate 16 (133 mg, 0.36 mmol, 1.20 equiv.) in a round bottom flask under argon. After stirring for 5 min, solid prednisolone (75 mg, 0.30 mmol) and DMAP (55 mg, 0.45 mmol, 1.50 equiv.) were added. The reaction mixture was allowed to stir for 14 h, diluted with CH$_2$Cl$_2$, filtered through Celite and the filtrate was concentrated to afford the crude as a pale yellow oil. The crude was purified by flash column chromatography (30 mL SiO$_2$, 70:30→50:50 hexanes/EtOAc) to afford a clear, colourless oil as desired conjugate LD20-PDL (142 mg, 68% yield).

R$_f$ 0.45 (SiO$_2$, 75:25 EtOAc/hexanes);
$^1$H NMR (CDCl$_3$, 300 MHz): δ 7.26 (d, J=10.5 Hz, 1H), 6.27 (dd, J=10.1, 1.8 Hz, 1H), 6.01 (s, 1H), 5.42-5.28 (m, 2H), 5.02 (d, J=17.4 Hz, 1H), 4.89 (d, J=17.3 Hz, 1H), 4.54-4.45 (m, 1H), 4.08 (t, J=6.9 Hz, 2H), 2.76 (d, J=6.3 Hz, 2H), 2.73-2.60 (m, 3H), 2.61-2.49 (m, 1H), 2.36-2.27 (m, 1H), 2.20-1.91 (m, 7H), 1.71-1.45 (m, 4H), 1.45 (s, 3H), 1.40-1.19 (m, 25H), 1.19-1.04 (m, 1H), 0.97 (s, 3H), 0.88 (br t, J=6.6 Hz, 3H).

0.5 M HCl (2×5 mL), H$_2$O (1×5 mL), brine (1×5 mL), dried over Na$_2$SO$_4$ and concentrated on a rotary evaporator. The crude was purified by flash column chromatography (25 mL SiO$_2$, 80:20)→50:50 hexanes/EtOAc) to afford a clear, colourless oil as desired conjugate LD10-DTX (89 mg, 81% yield).

R$_f$ 0.34 (SiO$_2$, 50:50 hexanes/EtOAc);
$^1$H NMR (300 MHz, CDCl$_3$): δ 8.13 (d, J=7.5 Hz, 2H), 7.67-7.58 (m, 1H), 7.57-7.47 (m, 2H), 7.46-7.36 (m, 2H), 7.36-7.26 (m, 3H), 6.30-6.14 (m, 1H), 5.69 (d, J=7.2 Hz, 1H), 5.50-5.16 (m, 12H), 4.97 (d, J=8.4 Hz, 1H), 4.38-4.0

SCHEME 20: Scheme for synthesis of LD$_{10}$-DTX, (2R,3S)-1-(((2aR,4S,4aS,6R,9S,11S,12S,12aR,12bS)-12b-acetoxy-12-(benzoyloxy)-4,6,11-trihydroxy-4a,8,13,13-tetramethyl-5-oxo-2a,3,4,4a,5,6,9,10,11,12,12a,12b-dodecahydro-1H-7,11-methanocyclodeca[3,4]benzo[1,2-b]oxet-9-yl)oxy)-3-((tert-butoxycarbonyl)amino)-1-oxo-3-phenylpropan-2-yl (2,3-bis((9Z,12Z)-octadeca-9,12-dienoyloxy)propyl) succinate.

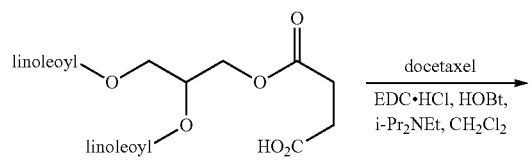

4

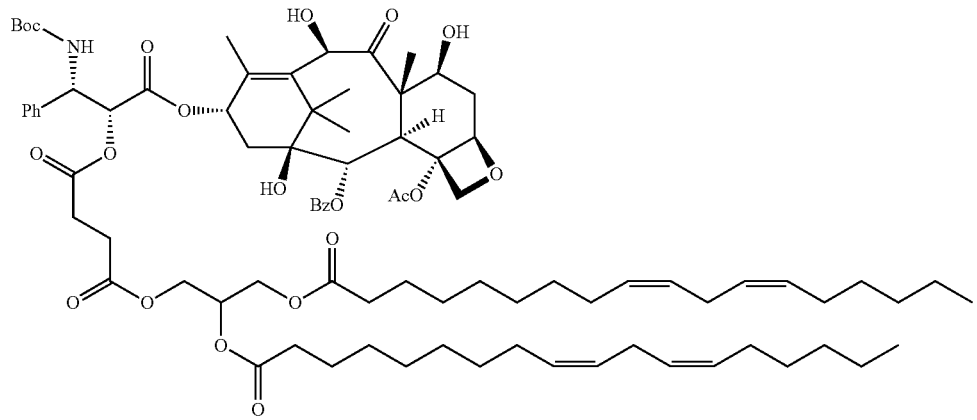

LD10-DTX

LD10-DTX: (2R,3S)-1-(((2aR,4S,4aS,6R,9S,11S,12S,12aR,12bS)-12b-acetoxy-12-(benzoyloxy)-4,6,11-trihydroxy-4a,8,13,13-tetramethyl-5-oxo-2a,3,4,4a,5,6,9,10,11,12,12a,12b-dodecahydro-1H-7,11-methanocyclodeca[3,4]benzo[1,2-b]oxet-9-yl)oxy)-3-((tert-butoxycarbonyl)amino)-1-oxo-3-phenylpropan-2-yl (2,3-bis((9Z,12Z)-octadeca-9,12-dienoyloxy)propyl) succinate EDC.HCl (15 mg, 8.10×10$^{-2}$ mmol, 1.10 equiv.) was added to a room temperature CH$_2$Cl$_2$ (1 mL) solution of hemisuccinate 4 (58 mg, 8.10×10$^{-2}$ mmol, 1.10 equiv.) and i-Pr$_2$NEt (19 μL, 0.11 mmol, 1.50 equiv.) in a round bottom flask under argon. The mixture was stirred for 5 min, cooled to 10° C., at which point docetaxel (59 mg, 7.36×10$^{-2}$ mmol) and HOBt (11 mg, 8.10×10$^{-2}$ mmol, 1.10 equiv.) were added and the mixture was allowed to warm up over 14 h. The reaction mixture was diluted with EtOAc, washed with aq.

(m, 8H), 3.94 (d, J=6.7 Hz, 1H), 2.83-2.52 (m, 9H), 2.43 (s, 3H), 2.32 (t, J=7.4 Hz, 6H), 2.15-1.98 (m, 6H), 1.94 (s, 3H), 1.47-1.18 (m, 50H), 1.14 (s, 3H), 0.89 (br t, J=6.6 Hz, 6H).

SCHEME 21: Scheme for synthesis of LD18-DTX, (2R,2S)-1-(((2aR,4S,4aS,6R,9S,11S,12S,12aR,12bs)-12b-acetoxy-12-(benzyloxy)-4,6,11-trihydroxy-4a,8,13,13-tetramethyl-5-oxo-2a,3,4,4a,5,6,9,10,11,12,12a,12b-dodecahydro-1H-7,11-methanocyclodeca[3,4]benzo[1,2-b]oxet-9-yl)oxy)-3-((tert-butoxycarbonyl)amino)-1-oxo-3-phenylpropan-2-yl (Z)-octadec-9-en-1-yl succinate.

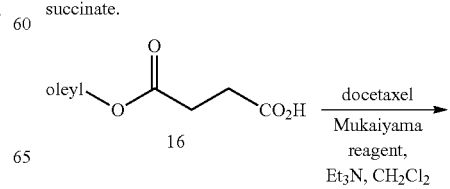

16

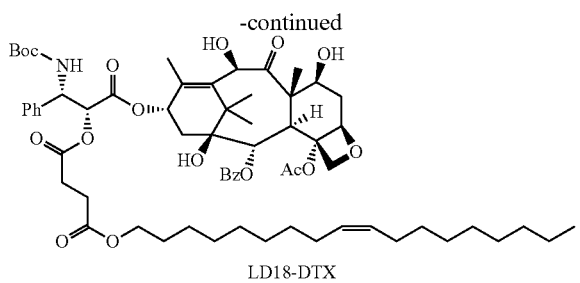

LD18-DTX

LD18-DTX: (2R,3S)-1-(((2aR,4S,4aS,6R,9S,11S, 12S,12aR,12bS)-12b-acetoxy-12-(benzoyloxy)-4,6, 11-trihydroxy-4a,8,13,13-tetramethyl-5-oxo-2a,3,4, 4a,5,6,9,10,11,12,12a,12b-dodecahydro-1H-7,11-methanocyclodeca[3,4]benzo[1,2-b]oxet-9-yl)oxy)-3-((tert-butoxycarbonyl)amino)-1-oxo-3-phenylpropan-2-yl(Z)-octadec-9-en-1-ylsuccinate Et$_3$N (35 µL, 0.25 mmol, 2.50 equiv.), followed by the Mukaiyama reagent (33 mg, 0.13 mmol, 1.30 equiv.), was added to an ice-cold CH$_2$Cl$_2$ (1 mL) solution of docetaxel (81 mg, 0.10 mmol) and hemisuccinate 16 (44 mg, 0.12 mmol, 1.20 equiv.) in a dry round bottom flask under argon. The reaction mixture was allowed to warm up over 14 h, then concentrated on a rotary evaporator. The crude was purified by flash column chromatography (25 mL SiO$_2$, 80:20→50:50 hexanes/EtOAc) to afford a clear, colourless oil as desired conjugate LD18-DTX (95 mg, 82% yield).

$^1$H NMR (300 MHz, CDCl$_3$): δ 8.13 (d, J=7.5 Hz, 2H), 7.67-7.58 (m, 1H), 7.57-7.47 (m, 2H), 7.46-7.36 (m, 2H), 7.36-7.26 (m, 3H), 6.34-6.17 (m, 1H), 5.70 (d, J=7.1 Hz, 1H), 5.49 (br s, 2H), 5.43-5.29 (m, 4H), 5.23 (s, 1H), 4.97 (d, J=8.2 Hz, 1H), 4.38-4.07 (m, 6H), 4.05 (t, J=6.8 Hz, 2H), 3.94 (d, J=6.8 Hz, 1H), 2.77-2.52 (m, 6H), 2.44 (s, 3H), 2.06 (s, 3H), 2.08-1.98 (m, 4H), 1.68-1.52 (m, 3H), 1.43-1.19 (m, 43H), 1.13 (s, 3H), 0.89 (br t, J=6.5 Hz, 3H).

SCHEME 22: Scheme for synthesis of LD22-DTX, (2R,2S)-1-(((2aR,4S,4aS,6R,9S,11S,12S,12aR,12bs)-12b-acetoxy-12-(benzyloxy)-4,6,11-trihydroxy-4a,8,13,13-tetramethyl-5-oxo-2a,3,4,4a,5,6,9,10,11,12,12a,12b-dodecahydro-1H-7,11-methanocyclodeca[3,4]benzo[1,2-b]oxet-9-yl)oxy)-3-((tert-butoxycarbonyl)amino)-1-oxo-3-phenylpropan-2-yl (2,3-bis(tetradecanoyloxy)propyl) succinate.

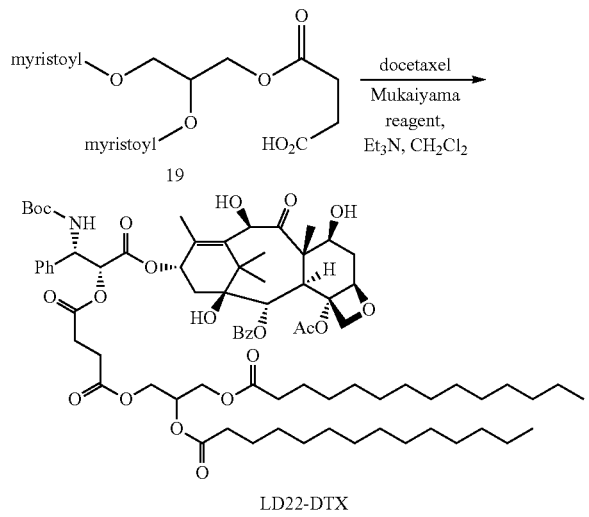

LD22-DTX

LD22-DTX: (2R,3S)-1-(((2aR,4S,4aS,6R,9S,11S, 12S,12aR,12bS)-12b-acetoxy-12-(benzoyloxy)-4,6, 11-trihydroxy-4a,8,13,13-tetramethyl-5-oxo-2a,3,4, 4a,5,6,9,10,11,12,12a,12b-dodecahydro-1H-7,11-methanocyclodeca[3,4]benzo[1,2-b]oxet-9-yl)oxy)-3-((tert-butoxycarbonyl)amino)-1-oxo-3-phenylpropan-2-yl (2,3-bis(tetradecanoyloxy) propyl) succinate Et$_3$N (35 µL, 0.25 mmol, 2.50 equiv.), followed by the Mukaiyama reagent (33 mg, 0.13 mmol, 1.30 equiv.), was added to an ice-cold CH$_2$Cl$_2$ (1 mL) solution of docetaxel (81 mg, 0.10 mmol) and hemisuccinate 19 (74 mg, 0.12 mmol, 1.20 equiv.) in a dry round bottom flask under argon. The reaction mixture was allowed to warm up over 14 h, then concentrated on a rotary evaporator. The crude was purified by flash column chromatography (25 mL SiO$_2$, 80:20→50:50 hexanes/EtOAc) to afford a clear, colourless oil as desired conjugate LD22-DTX (63 mg, 45% yield).

$^1$H NMR (300 MHz, CDCl$_3$): δ 8.13 (d, J=7.2 Hz, 2H), 7.67-7.58 (m, 1H), 7.57-7.47 (m, 2H), 7.46-7.36 (m, 2H), 7.36-7.26 (m, 3H), 6.30-6.14 (m, 1H), 5.70 (d, J=7.2 Hz, 1H), 5.60-5.41 (m, 2H), 5.36 (br s, 1H), 4.97 (d, J=8.4 Hz, 1H), 4.40-4.07 (m, 9H), 3.94 (d, J=6.7 Hz, 1H), 2.80-2.51 (m, 6H), 2.43 (s, 3H), 2.32 (t, J=7.4 Hz, 6H), 1.95-1.81 (m, 3H), 1.94 (s, 3H), 1.69-1.53 (m, 5H), 1.14 (s, 3H), 1.41-1.18 (m, 54H), 1.14 (s, 3H), 0.89 (br t, J=6.6 Hz, 6H).

SCHEME 23: Scheme for synthesis of LD23-DTX, (2R,3S)-1-(((2aR,4S,4aS,6R,9S,11S,12S,12aR,12bs)-12b-acetoxy-12-(benzyloxy)-4,6,11-trihydroxy-4a,8,13,13-tetramethyl-5-oxo-2a,3,4,4a,5,6,9,10,11,12, 12a,12b-dodecahydro-1H-7,11-methanocyclodeca[3,4]benzo[1,2-b]oxet-9-yl)oxy)-3-((tert-butoxycarbonyl)amino)-1-oxo-3-phenylpropan-2-yl (2,3-bis(oleoyloxy)propyl) succinate.

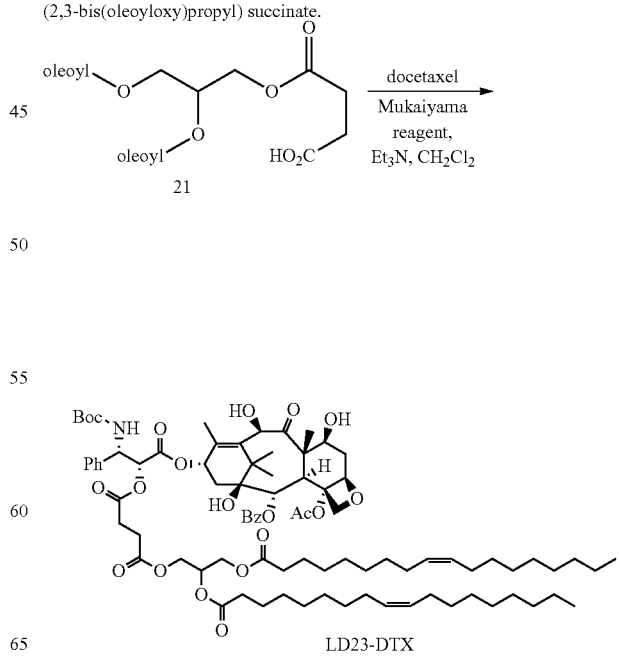

LD23-DTX

LD23-DTX: (2R,3S)-1-(((2aR,4S,4aS,6R,9S,11S, 12S,12aR,12bS)-12b-acetoxy-12-(benzoyloxy)-4,6, 11-trihydroxy-4a,8,13,13-tetramethyl-5-oxo-2a,3,4, 4a,5,6,9,10,11,12,12a,12b-dodecahydro-1H-7,11-methanocyclodeca[3,4]benzo[1,2-b]oxet-9-yl)oxy)-3-((tert-butoxycarbonyl)amino)-1-oxo-3-phenylpropan-2-yl (2,3-bis(oleoyloxy)propyl) succinate Et$_3$N (26 µL, 0.18 mmol, 3.00 equiv.), followed by the Mukaiyama reagent (25 mg, $9.90 \times 10^{-2}$ mmol, 1.60 equiv.), was added to an ice-cold CH$_2$Cl$_2$ (0.6 mL) solution of docetaxel (50 mg, $6.19 \times 10^{-2}$ mmol) and hemisuccinate 21 (67 mg, $9.28 \times 10^{-2}$ mmol, 1.50 equiv.) in a dry round bottom flask under argon. The reaction mixture was allowed to warm up over 14 h, then concentrated on a rotary evaporator. The crude was purified by flash column chromatography (25 mL SiO$_2$, 60:40 hexanes/EtOAc) to afford a clear, colourless oil as desired conjugate LD23-DTX (59 mg, 63% yield).

$^1$H NMR (300 MHz, CDCl$_3$): δ 8.13 (d, J=7.5 Hz, 2H), 7.67-7.58 (m, 1H), 7.57-7.47 (m, 2H), 7.46-7.36 (m, 2H), 7.36-7.26 (m, 3H), 6.30-6.14 (m, 1H), 5.69 (d, J=7.2 Hz, 1H), 5.57-5.42 (m, 2H), 5.42-5.19 (m, 8H), 4.97 (d, J=8.4 Hz, 1H), 4.38-4.07 (m, 8H), 3.94 (d, J=6.7 Hz, 1H), 2.83-2.50 (m, 6H), 2.43 (s, 3H), 2.32 (t, J=7.4 Hz, 6H), 2.11-1.81 (m, 8H), 1.94 (s, 3H), 1.69-1.53 (m, 5H), 1.45-1.17 (m, 56H), 1.13 (s, 3H), 0.89 (br t, J=6.6 Hz, 6H).

SCHEME 24: Scheme for synthesis of LD12-ABN, (3S,8R,9S,10R,13S,14S)-10,13-dimethyl-17-(pyridin-3-yl)-2,3,4,7,8,9,10,11,12,13,14,15-dodecahydro-1H-cyclopenta[a]phenanthren-3-yl linoleyl succinate.

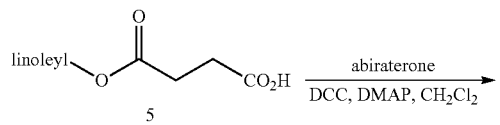

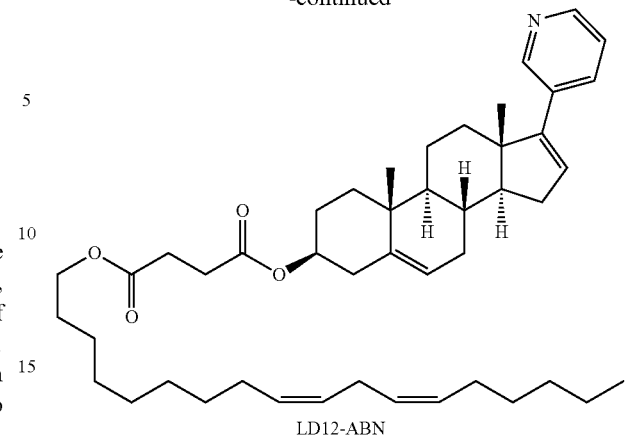

LD12-ABN: (3S,8R,9S,10R,13S,14S)-10,13-dimethyl-17-(pyridin-3-yl)-2,3,4,7,8,9,10,11,12,13,14,15-dodecahydro-1H-cyclopenta[a]phenanthren-3-yl linoleyl succinate DCC (17 mg, $8.25 \times 10^{-2}$ mmol, 1.10 equiv.) was added to an ice-cold CH$_2$Cl$_2$ (0.7 mL) solution of hemisuccinate 5 (30 mg, $8.25 \times 10^{-2}$ mmol, 1.10 equiv.) in a round bottom flask under argon, followed by abiraterone (26 mg, $7.5 \times 10^{-2}$ mmol) and DMAP (10 mg, $8.25 \times 10^{-2}$ mmol, 1.10 equiv.). The reaction mixture was allowed to warm up over 14 h, filtered through Celite and concentrated on a rotary evaporator. The crude was purified by flash column chromatography (20 mL SiO$_2$, 70:30 hexanes/EtOAc) to afford a clear, colourless oil as desired conjugate LD12-ABN (31 mg, 60% yield).

$^1$H NMR (300 MHz, CDCl$_3$): δ 8.61 (s, 1H), 8.45 (d, J=3.9 Hz, 1H), 7.63 (dt, J=8.0, 1.9 Hz, 1H), 7.21 (dd, J=7.9, 4.8 Hz, 1H), 6.01-5.94 (m, 1H), 5.45-5.25 (m, 5H), 4.71-4.55 (m, 1H), 4.07 (t, J=6.7 Hz, 2H), 2.76 (t, J=6.0 Hz, 2H), 2.60 (s, 4H), 2.39-2.31 (m, 2H), 2.32-2.19 (m, 1H), 2.12-1.97 (m, 7H), 1.92-1.42 (m, 12H), 1.41-1.23 (m, 17H), 1.21-1.07 (m, 2H), 1.07 (s, 3H), 1.03 (s, 3H), 0.87 (br t, J=6.7 Hz, 3H).

SCHEME 25: Scheme for synthesis of LD$_{11}$-NPC$_1$, linoleyl 4-((2-((4-(2-(2-((3r,5r,7r)-adamantan-1-yl)acetamido)acetyl)piperazin-1-yl)methyl)phenoxy)methyl)benzoate.

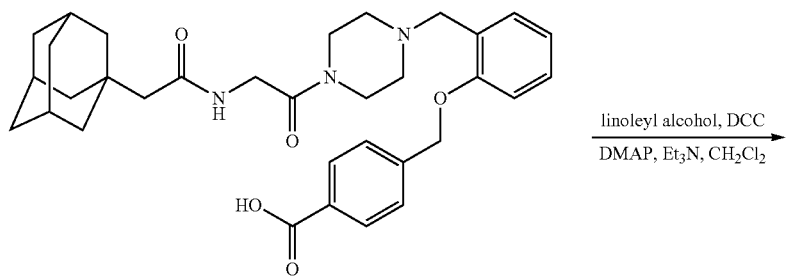

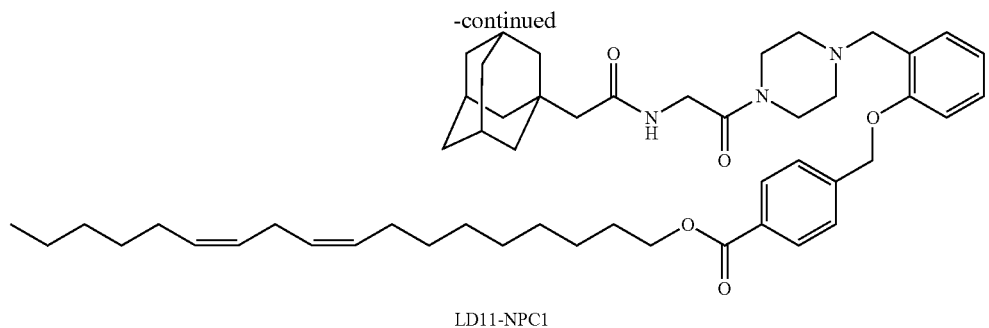

LD11-NPC1

LD11-NPC1: linoleyl 4-((2-((4-(2-(2-(((3r,5r,7r)-adamantan-1-yl)acetamido)acetyl)piperazin-1-yl)methyl)phenoxy)methyl)benzoate DCC (18 mg, 8.65×10⁻² mmol, 1.10 equiv.) was added to an ice-cold CH$_2$Cl$_2$ (0.8 mL) solution of NPC$_1$I [Lee et al. (2013)] (44 mg, 7.86×10⁻² mmol) and Et$_3$N (22 µL, 0.16 mmol, 2.00 equiv.) in a round bottom flask under argon, then removed from the cold bath and stirred for 15 min. The reaction mixture was placed back in the ice bath, then linoleyl alcohol (23 mg, 8.65×10⁻² mmol, 1.10 equiv.) and DMAP (11 mg, 8.65×10⁻² mmol, 1.10 equiv.) were added and the mixture was allowed to warm up over 14 h. The reaction mixture was diluted with Et$_2$O, washed with aq. 5% NaHCO$_3$ (1×5 mL), brine (1×5 mL), dried over Na$_2$SO$_4$ and concentrated on a rotary evaporator. The crude was purified by flash column chromatography (20 mL SiO$_2$, 75:25:0→100:0:0→98:0:2 EtOAc/hexanes/MeOH) to afford a clear, colourless oil as desired conjugate LD11-NPC1 (26 mg, 41% yield).

$R_f$ 0.40 (SiO$_2$, 65:30:5 EtOAc/hexanes/MeOH); 1H NMR (300 MHz, CDCl$_3$): δ 8.06 (d, J=8.1 Hz, 2H), 7.49 (d, J=8.1 Hz, 2H), 7.34 (d, J=7.4 Hz, 1H), 7.22 (d, J=7.4 Hz, 1H), 6.97 (t, J=7.4 Hz, 1H), 6.90 (d, J=8.1 Hz, 1H), 6.52 (br s, 1H), 5.45-5.26 (m, 4H), 5.14 (s, 2H), 4.31 (t, J=6.7 Hz, 2H), 4.04 (d, J=3.4 Hz, 2H), 3.67 (hr s, 4H), 3.41 (br t, J=4.4 Hz, 2H), 2.77 (t, J=5.9 Hz, 2H), 2.52 (br t, J=4.7 Hz, 4H), 2.11-1.90 (m, 9H), 1.85-1.53 (m, 6H), 1.50-1.18 (m, 18H), 0.88 (br t, J=6.8 Hz, 3H).

SCHEME 26: Scheme for synthesis of LD$_{25}$-NPC$_1$, octyl 4-((2-((4-(2-(2-((3r,5r,7r)-adamantan-1-yl)acetamido)acetyl)piperazin-1-yl)methyl)phenoxy)methyl)benzoate.

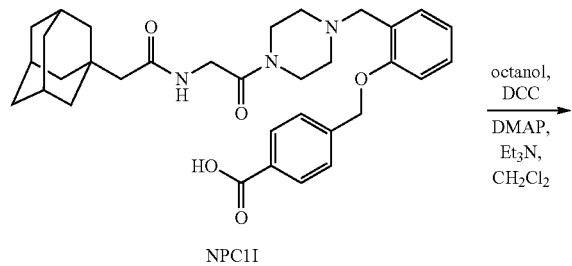

NPC1I octanol, DCC
—————→
DMAP, Et$_3$N, CH$_2$Cl$_2$

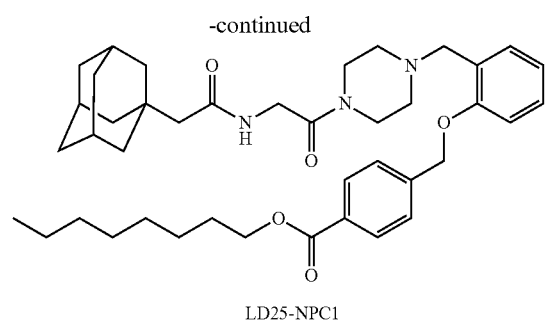

LD25-NPC1

LD25-NPC1: octyl 4-((2-((4-(2-(2-((3r,5r,7r)-adamantan-1-yl)acetamido)acetyl)piperazin-1-yl)methyl)phenoxy)methyl)benzoate DCC (50 mg, 0.24 mmol, 1.20 equiv.) was added to an ice-cold CH$_2$Cl$_2$ (1 mL) solution of NPC$_1$I (112 mg, 0.20 mmol) and Et$_3$N (69 µL, 0.50 mmol, 2.50 equiv.) in a round bottom flask under argon, then removed from the cold bath and stirred for 15 min. The reaction mixture was placed back in the ice bath, then octanol (41 µL, 0.26 mmol, 1.30 equiv.) and DMAP (29 mg, 0.24 mmol, 1.20 equiv.) were added and the mixture was allowed to warm up over 14 h. The reaction mixture was diluted with Et$_2$O, washed with aq. 5% NaHCO$_3$ (1×5 mL), brine (1×5 mL), dried over Na$_2$SO$_4$ and concentrated on a rotary evaporator. The crude was purified by flash column chromatography (20 mL SiO$_2$, 50:45:5 EtOAc/hexanes/MeOH) to afford a clear, colourless oil as desired conjugate LD11-NPC1 (73 mg, 54% yield).

$R_f$ 0.47 (SiO$_2$, 50:40:10 EtOAc/hexanes/MeOH);

¹H NMR (300 MHz, CDCl$_3$): δ 8.06 (d, J=8.1 Hz, 2H), 7.49 (d, J=8.1 Hz, 2H), 7.34 (d, J=7.4 Hz, 1H), 7.22 (d, J=7.4 Hz, 1H), 6.97 (t, J=7.4 Hz, tH), 6.90 (d, J=8.1 Hz, 1H), 6.52 (br s, 1H), 5.15 (s, 2H), 4.33 (t, J=6.6 Hz, 2H), 4.05 (d, J=3.5 Hz, 2H), 3.66 (br s, 4H), 3.40 (br t, J=4.2 Hz, 2H), 2.51 (br t, J=4.3 Hz, 4H), 2.08-1.87 (m, 6H), 1.85-1.53 (m, 15H), 1.52-1.20 (m, 11H), 0.88 (br t, J=6.8 Hz, 3H).

SCHEME 27: Scheme for synthesis of LD$_{26}$-NPC$_1$, decyl 4-((2-((4-(2-(2-((3r,5r,7r)-adamantan-1-yl)acetamido)acetyl)piperazin-1-yl)methyl)phenoxy)methyl)benzoate.

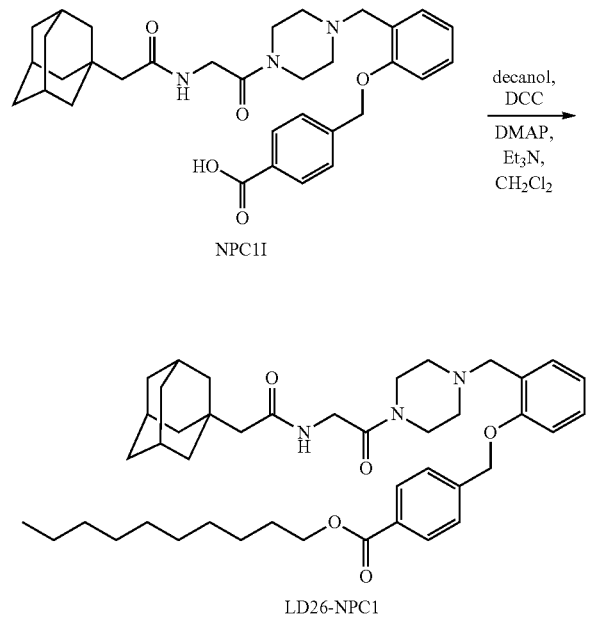

LD26-NPC1

LD25-NPC1: decyl 4-((2-((4-(2-(2-((3r,5r,7r)-adamantan-1-yl)acetamido)acetyl)piperazin-1-yl)methyl)phenoxy)methyl)benzoate DCC (50 mg, 0.24 mmol, 1.20 equiv.) was added to an ice-cold CH$_2$Cl$_2$ (1 mL) solution of NPC$_1$I (112 mg, 0.20 mmol) and Et$_3$N (69 µL, 0.50 mmol, 2.50 equiv.) in a round bottom flask under argon, then removed from the cold bath and stirred for 15 min. The reaction mixture was placed back in the ice bath, then decanol (50 µL, 0.26 mmol, 1.30 equiv.) and DMAP (29 mg, 0.24 mmol, 1.20 equiv.) were added and the mixture was allowed to warm up over 14 h. The reaction mixture was diluted with Et$_2$O, washed with aq. 5% NaHCO$_3$ (1×5 mL), brine (1×5 mL), dried over Na$_2$SO$_4$ and concentrated on a rotary evaporator. The crude was purified by flash column chromatography (20 mL SiO$_2$, 50:45:5 EtOAc/hexanes/MeOH) to afford a clear, colourless oil as desired conjugate LD11-NPC1 (68 mg, 49% yield).

R$_f$ 0.47 (SiO$_2$, 50:40:10 EtOAc/hexanes/MeOH);

$^1$H NMR (300 MHz, CDCl$_3$): δ 8.06 (d, J=8.1 Hz, 2H), 7.49 (d, J=8.1 Hz, 2H), 7.34 (d, J=7.4 Hz, 1H), 7.22 (d, J=7.4 Hz, 1H), 6.97 (t, J=7.4 Hz, 1H), 6.90 (d, J=8.1 Hz, 1H), 6.52 (br s, 1H), 5.15 (s, 2H), 4.33 (t, J=6.6 Hz, 2H), 4.05 (d, J=3.5 Hz, 2H), 3.66 (br s, 4H), 3.40 (br t, J=4.2 Hz, 2H), 2.51 (br t, J=4.3 Hz, 4H), 2.08-1.87 (m, 6H), 1.85-1.53 (m, 15H), 1.52-1.20 (m, 15H), 0.88 (br t, J=6.8 Hz, 3H).

SCHEME 28: Scheme for synthesis of NPC$_1$I, 4-((2-((4-(2-(2-((3r,5r,7r)-adamantan-1-yl)acetamido)acetyl)piperazin-1-yl)methyl)phenoxy)methyl)benzoic acid.

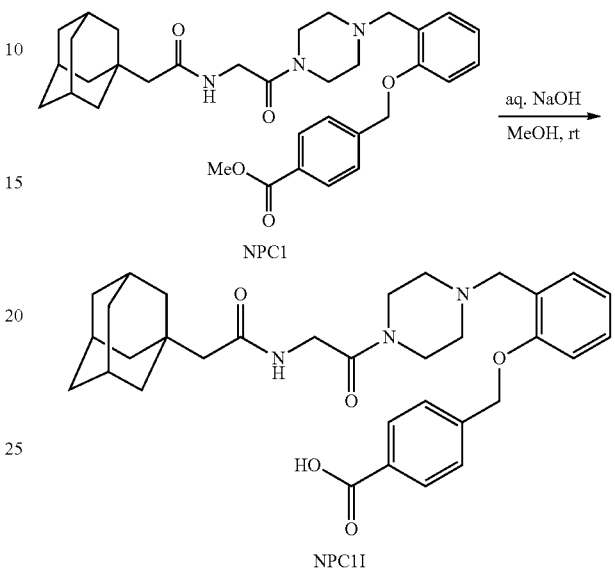

NPC$_1$I: 4-((2-((4-(2-(2-((3r,5r,7r)-adamantan-1-yl)acetamido)acetyl)piperazin-1-yl)methyl)phenoxy)methyl)benzoic acid Aqueous 1 M NaOH (6.1 mL, 6.13 mmol, 2.00 equiv.) was added to a room temperature MeOH (9 mL) solution of NPC1. ((Lee et al. 2013) 1.76 g, 3.06 mmol) in a round bottom flask under argon and stirred. After 14 h, the pH of the mixture was adjusted to ≤2 by addition of aqueous 1 M HCl, then extracted with CHCl$_3$ (3×15 mL). The combined organic extracts were dried over Na$_2$SO$_4$ and concentrated on a rotary evaporator to afford a white foam (1.60 g, 93% yield), which was used without further purification.

R$_f$ 0.28 (SiO$_2$, 70:20:10 EtOAc/hexanes/MeOH); $^1$H NMR (300 MHz, CD$_3$OD): δ 8.07 (d, J=8.4 Hz, 2H), 7.61 (d, J=8.4 Hz, 2H), 7.53-7.44 (m, 2H), 7.21 (d, J=8.4 Hz, 1H), 7.10 (t, J=7.5 Hz, 1H), 5.32 (s, 2H), 4.40 (s, 2H), 4.07-4.01 (m, 2H), 3.78 (br s, 4H), 2.02 (s, 2H), 2.00-1.90 (m, 5H), 1.79-1.61 (M, 16H).

SCHEME 29. Scheme for synthesis of LD$_{01}$-RXN and LD$_{01}$-TFN

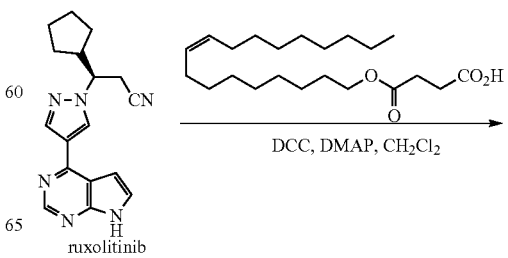

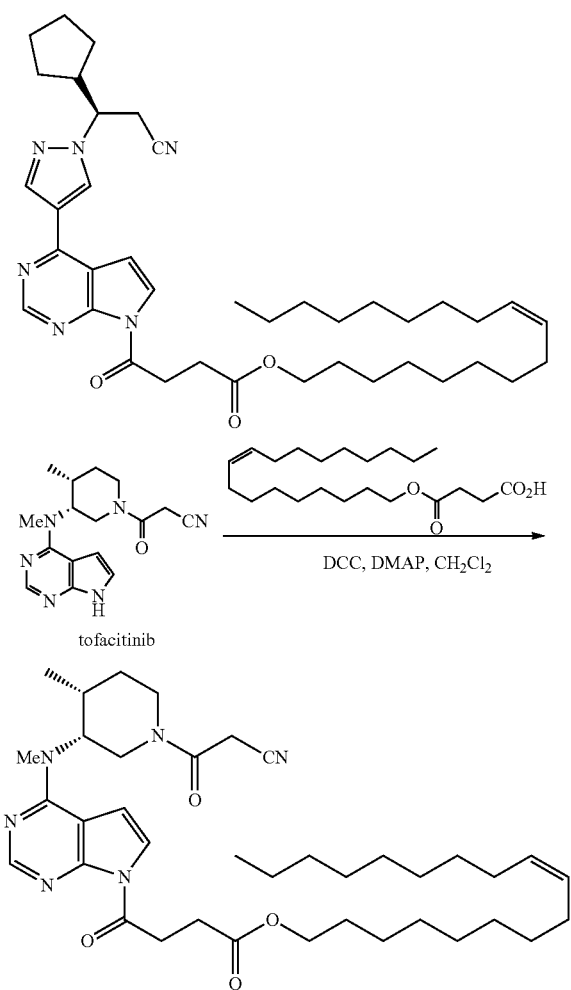

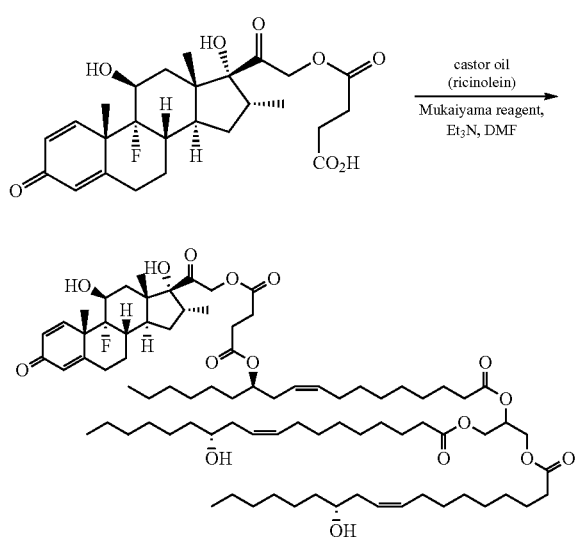

Example Schemes

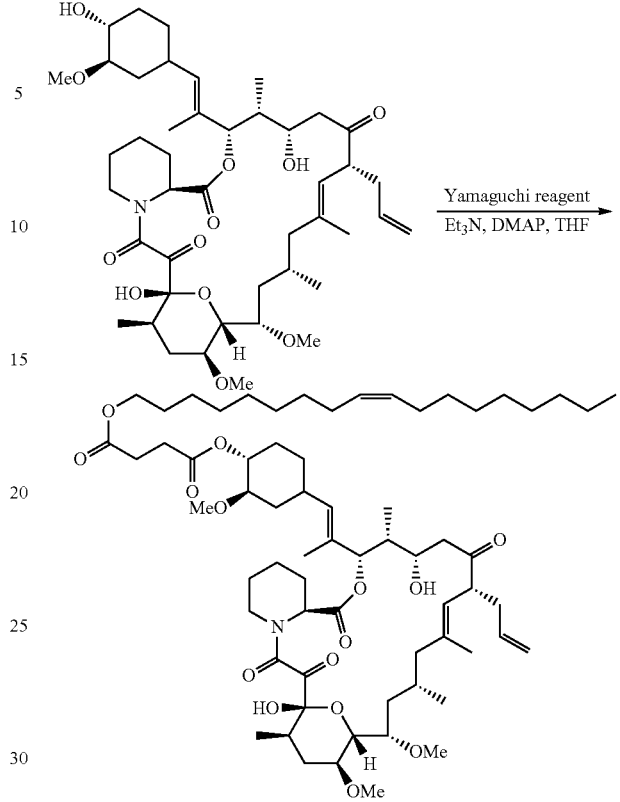

Formulation of DEX or DTX into Lipid Nanoparticles

The hydrophobic properties of the lipid-linked prodrugs (comprised of the drug and lipid moieties) allow drugs to be easily incorporated in lipid nanoparticles by simply adding it to the lipid formulation mixture without further modification of the formulation process. As a result, lipid nanoparticles incorporating these drugs can be made using a wide variety of well described formulation methodologies including but not limited to extrusion, ethanol injection and in-line mixing [Maclachlan and Cullis (2005); and Jeffs et al. (2005)].

Materials: 1-palmitoyl-2-oleoyl-sn-glycero-3-phosphocholine (POPC) and 1,2-Distearoyl-sn-glycero-3-phosphocholine (DSPC), 1,2-dimyristoyl-sn-glycero-3-phosphoethanolamine-N-[methoxy(polyethylene glycol)-2000] (PEG-DMPE), and 1,2-distearoyl-sn-glycero-3-phosphoethanolamine-N-[amino(polyethylene glycol)-2000] (PEG-DSPE) were purchased from Avanti Polar Lipids™ (Alabaster, Ala.). Cholesterol was obtained from Sigma™ (St Louis, Mo.). Ionizable lipids are commercially available. LD-DEX or LD-DTX prodrugs were synthesized as described above.

Preparation of LNP Systems: PC-Chol LNP systems were prepared by rapidly mixing POPC, cholesterol, lipid-linked prodrug and PEG-DMPE (in molar ratio of 49/39/10/2) dissolved in ethanol with phosphate-buffered saline using a T-junction mixer. Formulations were dialyzed against phosphate-buffered saline to remove residual ethanol and to raise the pH to 7.4. PC-TO and ionizable LNP systems were prepared in the same way except that the lipid compositions for these systems are: POPC, triolein, lipid-linked prodrug and PEG-DSPE (in molar ration of 19/70/10/1), and ionizable lipid, DSPC, cholesterol, lipid-linked prodrug and PEG-DMPE (in molar ration of 40/10/38.5/10/1.5), respectively.

Characterization of LNP: Particle size was determined by dynamic light scattering using a Malvern Zetasizer Nano ZS™ (Malvern, UK) following buffer exchange into phosphate-buffered saline. Number-weighted size and distribution data was used. Lipid concentrations were determined by measuring total cholesterol using the Cholesterol E enzymatic assay kit from Wako Chemicals USA™ (Richmond, Va.). The morphology of LNP formulations containing LD-DEX was analyzed by cryogenic-transmission electron microscopy (cryoTEM) as described previously [Leung et al. (2012)].

Quantitation of prodrugs by HPLC: LD-DEX/DTX were quantified by ultra high-pressure liquid chromatography (UHPLC) using a Waters Acquity™ UPLC system equipped with a photodiode array detector (PDA) and evaporative light scattering (ELS) detector; Empower™ data acquisition software version 3.0 was used (Waters™, USA). Separations were performed using a Waters Acquity™ BEH C18 column (1.7 µm, 2.1×100 mm) at a flow rate of 0.5 ml/min, with mobile phases A and B consisting of methanol/10 mM ammonium bicarbonate (80/20% v/v) and methanol/acetonitrile (80/20% v/v), respectively. The mobile phases were delivered at a programmed linear gradient (45%-80% B in 1 min then to 99% B at 2 min) at a column temperature of 55° C. The analyte was measured by PDA (at a wavelength of 239 nm) and ELS detector against calibration standard curves. For the analysis of LD-DEX/DTX breakdown to active compound, linear gradients of 20/80% to 100/0% (acetonitrile/water, v/v) over 7 min were used.

Cryo-TEM of LNP: A small amount of formulations at ~20 mg/mL (total lipid concentration) was applied to an electron microscopy grid with a perforated carbon film. The sample was rapidly frozen in liquid ethane using a Vitrobot™ system (FEI™, Hillsboro, Oreg.). Images were taken using an FEI G20 Lab6 200 kV TEM (FEI™, Hillsboro, Oreg.) under cryogenic conditions (88 K) at a magnification of 50,000× with an AMT HR CCD camera. Representative images of LD02 and LD03 in PC-Chol LNP made with 5 mol % PEG-DSPE are shown.

In Vitro Degradation of Lipid Linked Prodrugs

To determine the biodegradability of the dexamethasone or docetaxel prodrugs (LD-DEX/DTX), 1 mg/mL LNP was incubated in mouse plasma (Cedarlane™, Burlington, Ontario) or PBS supplemented with 10 U of purified esterase (Sigma-Aldrich™, St. Louis, Mo.) for up to 4 hours at 37° C. Post incubation, four volumes of chloroform/methanol (2:1) was added and the mixture was vortex mixed. Samples were centrifuged at 13,000 g for 5 minutes and the upper phase was discarded. The remaining organic phase was dried down under vacuum and the resulting lipid extract was dissolved in methanol/acetonitrile (1:1). Quantity of parent LD-DEX/DTX compound was determined by ultra high pressure liquid chromatography on a Waters Acquity™ H-Class UPLC System™ equipped with a BEH C18 column and a photodiode array detector.

In Vitro Dissociation of Lipid-linked Prodrugs

LNP were incubated for 0, 3, 5 and 24 h at 37° C. in 400 µL of sterile human plasma (Cedarlane™, Burlington, Ontario) at a final lipid concentration of 1.2 mM. At the various time-points, samples were loaded onto a 1.5×27 cm Sepharose CL-4B column (Sigma-Aldrich™, St. Louis, Mo.). 30×2 mL fractions were collected. Three volumes of methanol/acetonitrile (1:1) were added to each fraction and analyzed by UHPLC to determine the residual LD-DEX/DTX as described above.

In Vivo Immune Suppression by Lipid-linked (LD-DEX) Prodrugs 6-8 Weeks old female C57Bl/6 mice (Charles River Laboratories™, Wilmington, Mass.) were injected intravenously with lipid nanoparticles containing CpG DNA oligonucleotides (10 mg/kg), mRNA (3 mg/kg) or plasmid DNA (pDNA) (1 mg/kg). Animals were euthanized 2 hours post-injection and blood was collected via intracardiac or saphenous sampling. Plasma was separated from whole blood by centrifugation and analyzed for proinflammatory cytokines using the Mesoscale Proinflammatory Multiplex™ kit (Rockville, Md.) according to manufacturer's instruction. All procedures were approved by the Animal Care Committee at the University of British Columbia and were performed in accordance with guidelines established by the Canadian Council on Animal Care.

In Vitro Immune Suppression by Lipid-linked (LD-DEX) Prodrugs

RAW 264.7 mouse macrophage cells were seeded at 250,000 cells per mL on 12-well plates and incubated at 37° C. overnight. Lipopolysaccharide (LPS) was dissolved in phosphate buffered saline at a concentration of 2 µg/ml. Cells were treated with lipid nanoparticles containing LD-DEX prodrugs and 2 ng/ml of LPS for 4 hours. This LPS concentration was chosen due to its ability to increase IL1β expression approximately 1000 times as compared to untreated cells. At the end of the incubation period, culture medium was aspirated and cellular RNA was extracted using the Purelink RNA™ extraction kit according to manufacturer's protocol (Life Technologies™, Burlington, ON). The concentration of extracted RNA was determined using a Nanodrop Lite™ (Thermo Fisher™). 1 µg of RNA was converted to cDNA using the High Capacity cDNA Reverse Transcription kit (Life Technologies™, Burlington, ON). In order to validate the sample preparation, a no template control and a negative reverse transcriptase control were included. The cDNA was then quantified using comparative real-time qPCR where the Ct (threshold cycle) values are converted to relative quantity using the 2-ΔΔCT method. The primer-probe sets were designed to bind to cDNA of Interleukin-1β(IL1β). Hypoxanthine-guanine phosphoribosyltransferase (HPRT) was chosen as the endogenous normalizer gene, which is known to maintain consistent levels with varying treatments.

In Vitro Growth Inhibition by Lipid-linked (LD-DTX) Prodrugs

OVCAR3 cells were obtained from ATCC (Manassas, Va.). Cells were seeded at 12,000 cells per well on 96-well plates and treated with free docetaxel, prodrugs, lipid nanoparticle formulations with or without prodrugs at 0 to 15 µM of docetaxel for 48 h. Cell viability was determined by a colorimetric assay, based on the tetrazolium salt MIT (3-(4, 5-dimethylthiazol-2-yl)-2,5-diphenyltetrazolium bromide), as described previously [Mossman 1983].

EXAMPLES

Example 1

Effect of Hydrophobicity on Prodrug Incorporation into LNP Preparation of DEX or DTX Prodrugs The lipid-linked prodrugs described herein may be comprised of a drug conjugated to one or more lipid moieties via a linker. A representative Dexamethasone (-DEX) based prodrug comprised of DEX linked to a single linoleyl acyl chain through an ester linkage is LD01-DEX. A representative Docetaxel (-DTX) based prodrug containing DTX linked to two linoleyl acyl chain through a hydrolysable ester linkage is LD10-DTX.

To define important properties/characteristics of these prodrugs that impact their utility, a series of DEX or DTX based prodrugs were produced. The exemplified lipid-linked prodrugs show variations to the lipid moiety (e.g. the number and length of acyl chains) as well as the linker (e.g. the presence or absence of a charged/ionizable group, degradability) to vary the release of active drug from the lipid-linked prodrug following in vivo administration. Examples of the DEX and DTX series are shown in TABLE 2 and TABLE 3, respectively, which specifies designation, lipid and linker characteristics and properties, chemical structure and hydrophobicity index (Log P). Examples of other lipid-linked prodrug including Abiraterone (-ABN), Tacrolimus (-TAC), Prednisone (-PDN), Prednisolone (—PDL), and NPC1 inhibitor NP3.47 (—NPC1B) are listed in TABLE 4.

TABLE 2

LD-DEX Prodrug Examples with Alternative Linkers and Lipids

| Compound Identifier | Active Drug | Lipid Moiety | Linker | Ionizable | Hydrophobicity Index of Prodrug (LogP) | |
|---|---|---|---|---|---|---|
| | | | | | nonionic | ionic |
| LD01-DEX | Dexamethasone | one acyl chain; linoleoyl (C18:2) | hydrolyzeable ester (succinyl) | ionizable dimethylamino function in headgroup MW = 856.1 | 8.57 | 5.07 |
| LD02-DEX | Dexamethasone | two acyl chains; linoleoyl (C18:2) | hydrolyzeable ester (succinyl) | no ionizable function in headgroup MW = 1091.5 | 14.95 | N/A |
| LD03-DEX | Dexamethasone | one acyl chain; linoleyl (C18:2) | hydrolyzeable ester (succinyl) | no ionizable function in headgroup MW = 741 | 8.92 | N/A |
| LD06-DEX | Dexamethasone | two acyl chains; linoleoyl (C18:2) | hydrolyzeable ester (succinyl) | ionizable dimethylamino function in headgroup MW = 1148.6 | 15.02 | 11.52 |
| LD07-DEX | Dexamethasone | one acyl chain; linoleoyl (C18:2) | non-hydrolyzeable ether linkage (1,4-dihydroxybutyl) | "non-degradable" analogue of LD03 MW = 729.09 | 10.36 | NA |
| LD13-DEX | Dexamethasone | one acyl chain; oleyl (C18:1) | hydrolyzeable ester (succinyl) | no ionizable function in headgroup MW = 743.01 | 9.28 | N/A |
| LD14-DEX | Dexamethasone | one acyl chain; palmityl (C16:0) | hydrolyzeable ester (succinyl) | no ionizable function in headgroup MW = 716.97 | 8.75 | N/A |
| LD17-DEX | Dexamethasone | two acyl chains; myristoyl (C14:0) | hydrolyzeable ester (succinyl) | no ionizable function in headgroup C57H91O12F MW = 987.34 | 12.84 | N/A |
| LD24-DEX | Dexamethasone | three acyl chains; ricinoleoyl (C18:1 + hydroxy at 12) | hydrolyzeable ester (succinyl) | no ionizable function in headgroup C83H135O16F MW = 1408.0 | 18.96 | N/A |

TABLE 3

LD-DTX Prodrug Examples with Alternative Linkers and Lipids

| Compound Identifier | Active Drug | Lipid Moiety | Linker | Ionizable | Hydrophobicity Index of Prodrug (LogP) | |
|---|---|---|---|---|---|---|
| | | | | | nonionic | ionic |
| LD10-DTX | Docetaxel | two acyl chains; | hydrolyzeable ester (succinyl) | no ionizable function in | 16.18 | N/A |

TABLE 3-continued

LD-DTX Prodrug Examples with Alternative Linkers and Lipids

| Compound Identifier | Active Drug | Lipid Moiety | Linker | Ionizable | Hydrophobicity Index of Prodrug (LogP) | |
|---|---|---|---|---|---|---|
| | | | | | nonionic | ionic |
| LD18-DTX | Docetaxel | linoleoyl (C18:2) one acyl chain; oleyl (C18:1) | hydrolyzeable ester (succinyl) | headgroup MW = 1506.9 no ionizable function in headgroup C65H91NO17 MW = 1158.4 | 10.51 | N/A |
| LD22-DTX | Docetaxel | two acyl chains; myristoyl (C14:0) | hydrolyzeable ester (succinyl) | no ionizable function in headgroup C78H115NO21 MW = 1402.8 | 14.07 | N/A |
| LD23-DTX | Docetaxel | two acyl chains; oleoyl (C18:1) | hydrolyzeable ester (succinyl) | no ionizable function in headgroup C86H127NO21 MW= 1511.0 | 16.9 | N/A |

TABLE 4

Other Prodrug Examples with Alternative Linkers and Lipids

| Compound Identifier | Active Drug | Lipid Moiety | Linker | Ionizable | Hydrophobicity Index of Prodrug (LogP) | |
|---|---|---|---|---|---|---|
| | | | | | nonionic | ionic |
| LD11-NPC1 | NPC1 inhibitor | one acyl chain; linoleyl (C18:2) | ester linkage; no additional linker | no ionizable function in headgroup MW = 808.16 | 10.77 | 8.43 |
| LD12-ABN | Abiraterone | one acyl chain; linoleyl (C18:2) | hydrolyzeable ester (succinyl) | no ionizable function in headgroup MW = 700.06 | 11.2 | 10.22 |
| LD15-TAC | Tacrolimus (FK-506) | one acyl chain; oleyl (C18:1) | hydrolyzeable ester (succinyl) | no ionizable function in headgroup C66H107NO15 MW = 1154.6 | 13.19 | N/A |
| LD19-PDN | Prednisone | one acyl chain; oleyl (C18:1) | hydrolyzeable ester (succinyl) | no ionizable function in headgroup C43H66O8 MW = 710.99 | 9.7 | N/A |
| LD20-PDL | Prednisolone | one acyl chain; oleyl (C18:1) | hydrolyzeable ester (succinyl) | no ionizeable function in headgroup C43H68O8 MW = 708.98 | 9.32 | N/A |
| LD25-NPC1 | NPC1 inhibitor | one acyl chain; octyl (C8:0) | hydrolyzeable ester (succinyl) | no ionizeable function in headgroup (but present in piperazine) MW = 671.9 | 7.05 | 4.71 |
| LD26-NPC1 | NPC1 inhibitor | one acyl chain; decyl (C10:0) | hydrolyzeable ester (succinyl) | no ionizeable function in headgroup (but present in piperazine) MW = 700.0 | 7.94 | 5.6 |

Example 2

Drug Loading Efficiencies

Analyses of lipid-linked prodrugs formulated as described above, confirmed that inclusion of up to 10 mol % DEX-based prodrugs in the initial formulation lipid mixture did not have any significant impacts on physicochemical or formulation characteristics such as size, and polydispersity. CryoTEM images for lipid-linked prodrugs (i.e. either LD02-DEX or LD03-DEX), two prodrugs of different lipid anchors and hydrophobicities, showed that these lipid-linked prodrugs are bilayer vesicles (see FIG. 1). As hypothesized, UHPLC lipid analyses of the final LNPs indicated that incorporation of DEX-based prodrugs was dependent of the hydrophobicity of the DEX-based prodrug. Therefore, LD01-DEX, which has a relatively low hydrophobicity, only 65-72 mol % of the input amount was found to be incorporated into the final lipid nanoparticle preparation (TABLE 5). LD06-DEX, which has a higher hydrophobicity than LD01-DEX, incorporated more in LNP than LD01-DEX. In contrast, LD02-, 03-, 07-, 13-, 14-, 17-, 21-, and 24-DEX which were designed to be more hydrophobic were efficiently (91-100%) incorporated into lipid-linked prodrugs as expected. However, while relative hydrophobicity is an essential component, it does not represent the only factor that impacts prodrug incorporation into lipid nanoparticles. The lower entrapment efficiency observed for LD01-DEX or LD06-DEX in comparison to LD03-DEX or LD02-DEX can be attributed, at least in part, to the presence of an ionizable group within the linker of LD01-DEX, which acts to alter the incorporation and disposition of the prodrugs in the lipid nanoparticles.

Similarly, UHPLC analyses of DTX-based prodrugs showed almost complete incorporation into lipid nanoparticles (TABLE 6). This is likely due to the relatively high hydrophobicity of these compounds.

TABLE 6

Efficiency of LD-DTX prodrug incorporation in lipid nanoparticles. Particle size is displayed in nm. Polydispersity index (PDI) is indicated in brackets.

| Lipid-linked Prodrug (LLP) | Predicted LogP | Particle size (PDI) PC-Chol LNP [ionizable LNP] | % Entrapment PC-Chol LNP [ionizable LNP] |
|---|---|---|---|
| LD10-DTX | 16.18 | 58 (0.06) [42 (0.06)] | 95 [100] |
| LD18-DTX | 10.51 | 80 (0.06) [40 (0.06)] | 100 [100] |
| LD22-DTX | 14.07 | 65 (0.04) [39 (0.07)] | 93 [100] |
| LD23-DTX | 16.9 | 60 (0.05) [39 (0.06)] | 100 [100] |

Example 3

Figure 2:
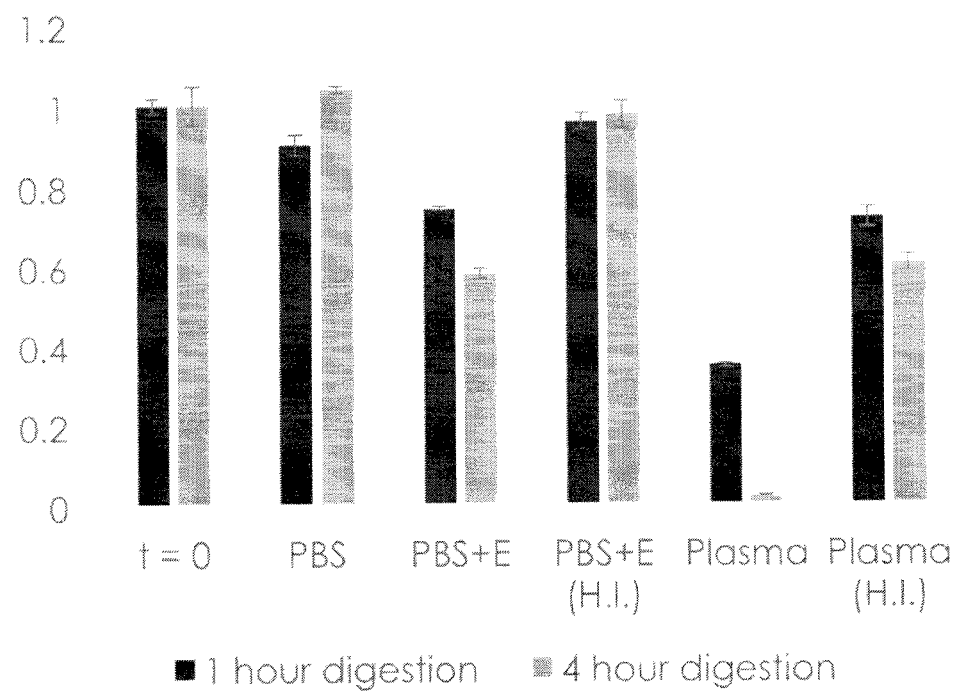
FIG. 2 shows the biodegradability of LD03-DEX LNP, wherein progressive cleavage of LD03-DEX prodrug from lipid-linked prodrug is mediated by plasma and isolated esterases over 1 and 4 h and data is normalized to the amount of respective prodrug in the pre-incubation mixture, with levels below 1 indicating degradation (Error bars represent standard deviation of at least three experiments).

Effect of Hydrophobicity on Release of Active Drug from Lipid-Linked Prodrugs The hydrophobicity may also be sufficient to promote efficient encapsulation/retention, and should ideally not result in the prodrug being substantially embedded or otherwise shielded in the lipid-linked prodrug. The drug may also be distributed in the lipid-linked prodrugs so as to allow access to the biodegradable linker, prodrug cleavage by appropriate intracellular enzymes and ultimately, release of the active drug from the lipid-linked prodrugs. UHPLC analyses showed that a 1 or 4 h incubation of LD03-DEX in either plasma or PBS containing isolated esterases resulted in progressive prodrug cleavage (FIG. 2). As expected, prodrug cleavage was suppressed by heat, likely due to enzyme inactivation.

To compare the relative cleavage rates of various DEX prodrugs, prodrug-containing lipid nanoparticles were incu

TABLE 5

Efficiency of LD-DEX prodrug incorporation in lipid nanoparticles as a function of hydrophobicity. Particle size is displayed in nm. Polydispersity index (PDI) is indicated in brackets.

Figure 3:
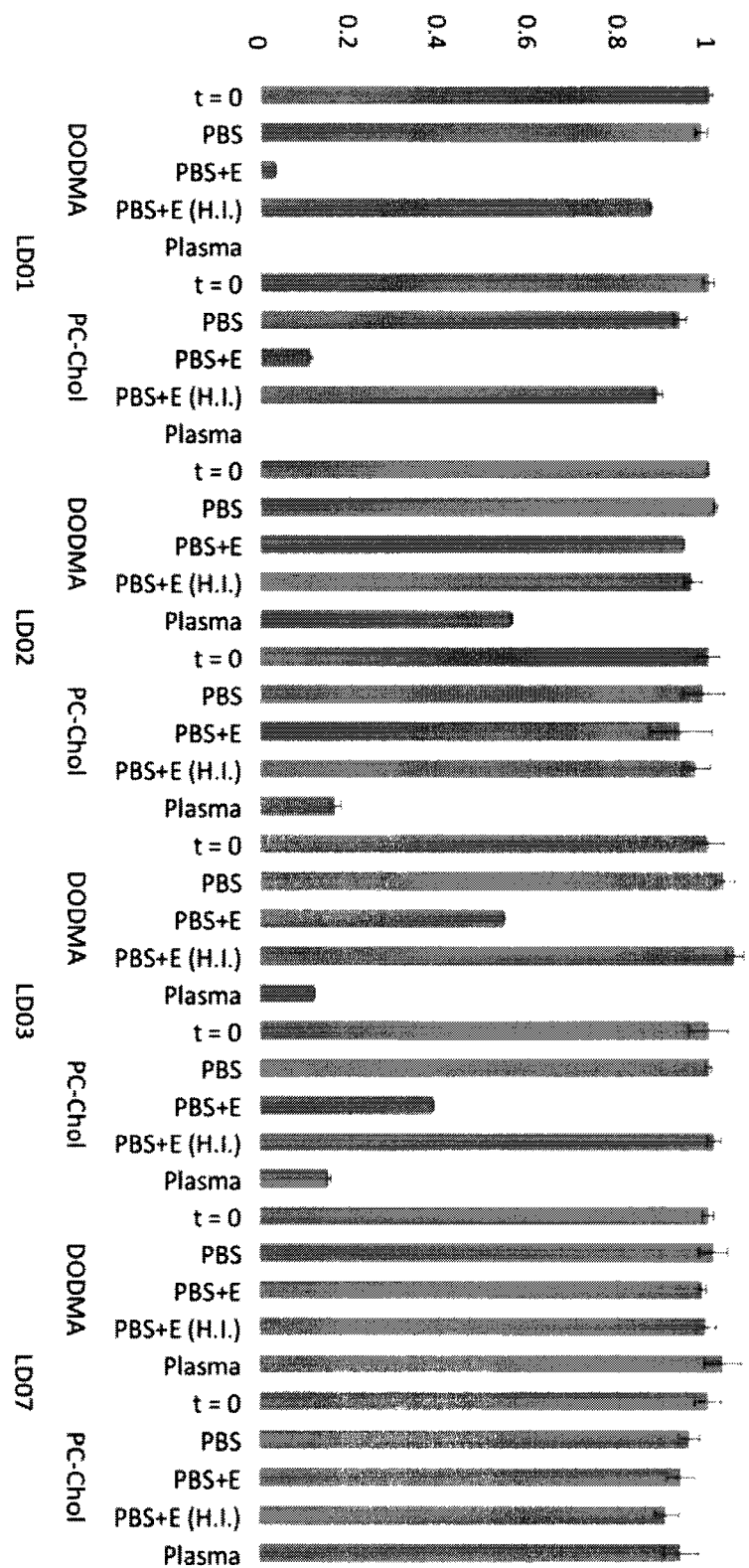
FIG. 3 shows the biodegradability of LD-DEX prodrugs, wherein the relative cleavage of LD01, LD02, LD03, and LD07-DEX prodrug from lipid-linked prodrug after 1 h incubation in plasma or PBS with/without enzyme and data is normalized to the amount of respective prodrug in the pre-incubation mixture, with levels below 1 indicating degradation (Error bars represent standard deviation of at least three experiments).
Figure 4:
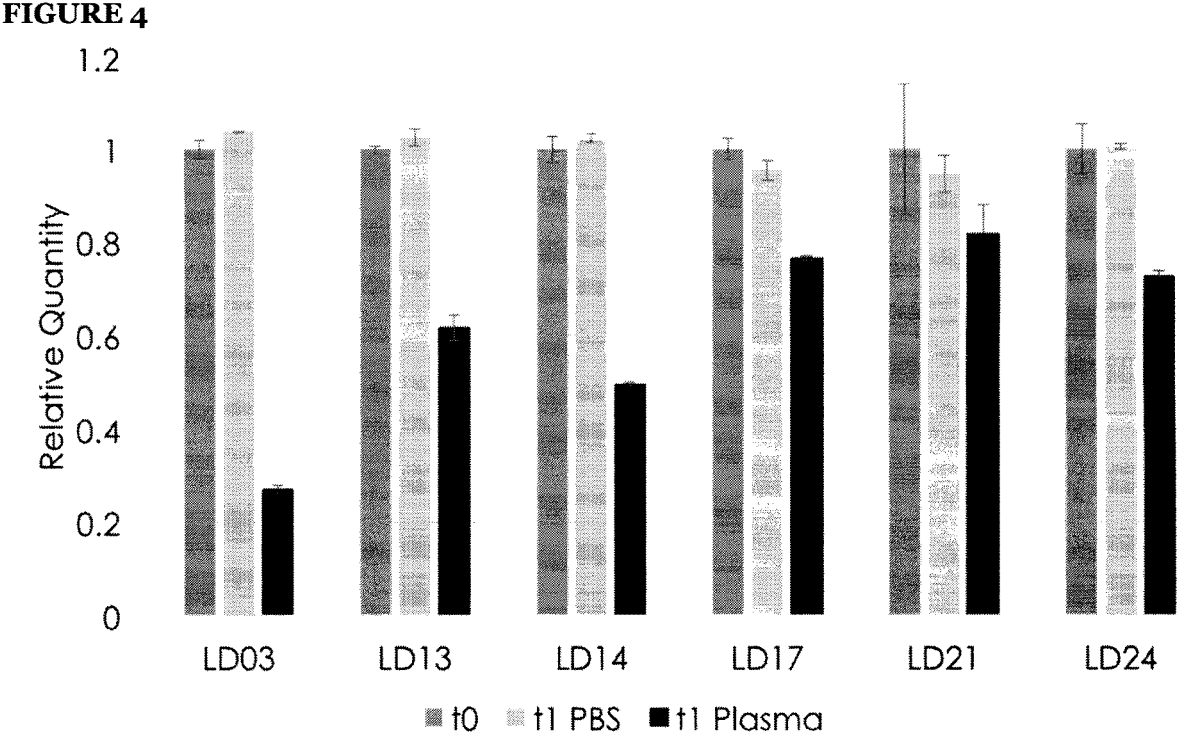
FIG. 4 shows the biodegradability of LD-DEX prodrugs in LNP, wherein LD03, LD13, LD14, LD17, LD21 and LD24 DEX prodrugs were formulated in LNP and incubated for 1 h in either PBS or mouse plasma and the amount of each prodrug was determined by UPLC analyses, and wherein the data was normalized to the amount of respective prodrug in the pre-incubation mixture, with levels below 1 indicating degradation (Error bars represent standard deviation of at least three experiments).

| Lipid-linked Prodrug (LLP) | Predicted LogP pH 5 | Predicted LogP pH 7.4 | Particle size (PDI) PC-Chol LNP [ionizable LNP] | % Entrapment PC-Chol LNP [ionizable LNP] |
|---|---|---|---|---|
| LD01-DEX | 5.07 | 8.57 | 77 (0.06) [51 (0.04)] | 72 [65] |
| LD02-DEX | | 14.95 | 53 (0.05) [49 (0.05)] | 100 [99] |
| LD03-DEX | | 8.92 | 64 (0.06) [48 (0.04)] | 94 [100] |
| LD06-DEX | 15.02 | 11.52 | 56 (0.03) [48 (0.04)] | 100 [88] |
| LD07-DEX | | 10.36 | 56 (0.03) [47 (0.04)] | 90 [88] |
| LD13-DEX | | 9.28 | 61 (0.03) [49 (0.07)] | 100 [96] |
| LD14-DEX | | 8.75 | 67 (0.05) [47 (0.06)] | 100 [95] |
| LD17-DEX | | 12.84 | [48 (0.06)] | 89 |
| LD21-DEX | | 15.67 | 54 (0.03) [48 (0.06)] | 100 [95] |
| LD24-DEX | | 18.96 | 57 (0.06) [49 (0.05)] | 100 [92] | bated for 1 h in plasma at 37° C., lipid was extracted using a modified Bligh-Dyer & Folsch method and then subjected to UHPLC analyses. As can be seen in FIG. 3, LD01-DEX and LD03-DEX demonstrated significant cleavage over this time period while in contrast, LD02-DEX showed virtually no degradation. As expected, LD07-DEX, which contains a non-degradable linker, also demonstrated no degradation. More examples of LD-DEX prodrug cleavage are shown in FIG. 4. As expected, LD-DEX prodrugs with relatively high hydrophobicities (such as LD17-, LD21- and LD24-DEX) were not susceptible to degradation in mouse plasma. In contrast, LD13- and LD14-DEX prodrugs, which have lower hydrophobicity than LD17-DEX and higher hydrophobicity than LD03-DEX, were partially degraded in plasma.

Figure 5A:
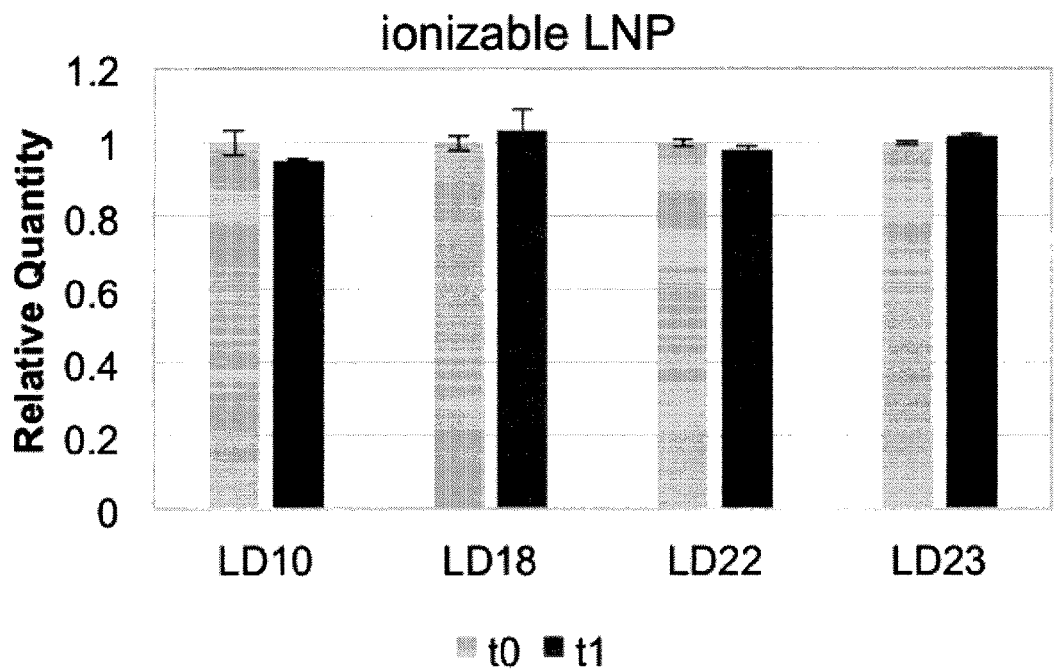
FIG. 5 shows the biodegradability of LD-DTX prodrugs in LNP, wherein LD10, LD18, LD22 and LD23 DTX prodrugs were formulated in either (B) PC-Chol, (C) PC-TO or (A) ionizable LNP and subjected to 1 h incubation in mouse plasma and the amount of each prodrug was determined by UPLC analyses, and the data was normalized to the amount of respective prodrug in the pre-incubation mixture (Error bars represent standard deviation of at least three experiments).
Figure 5B:
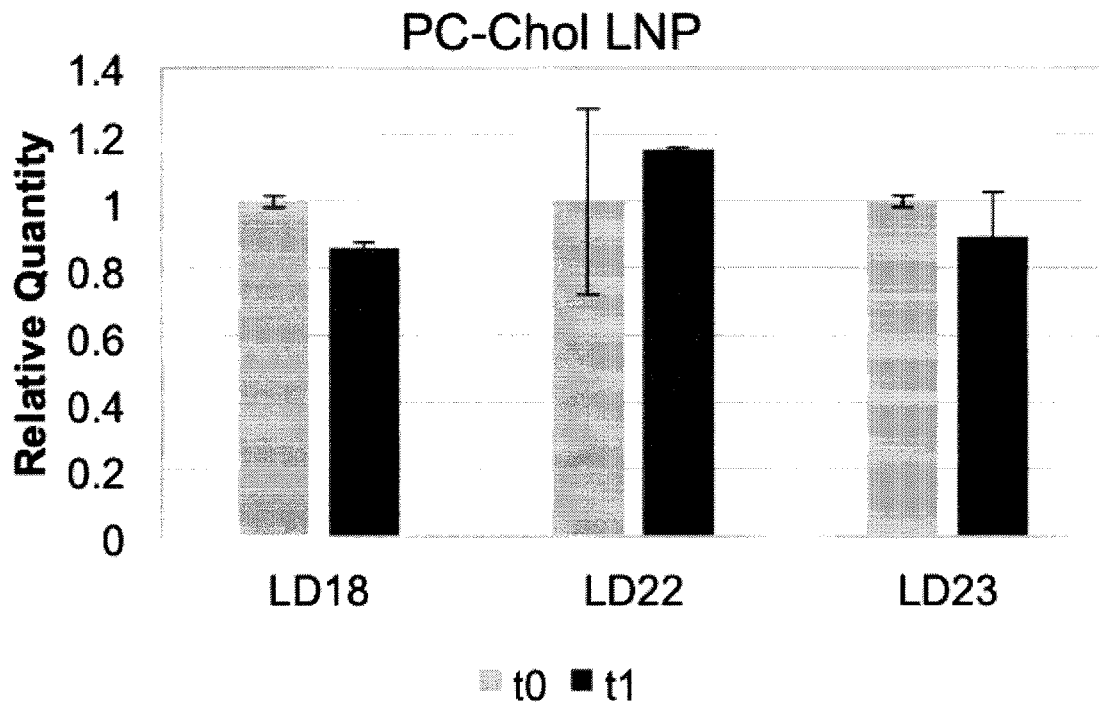
Figure 5C:
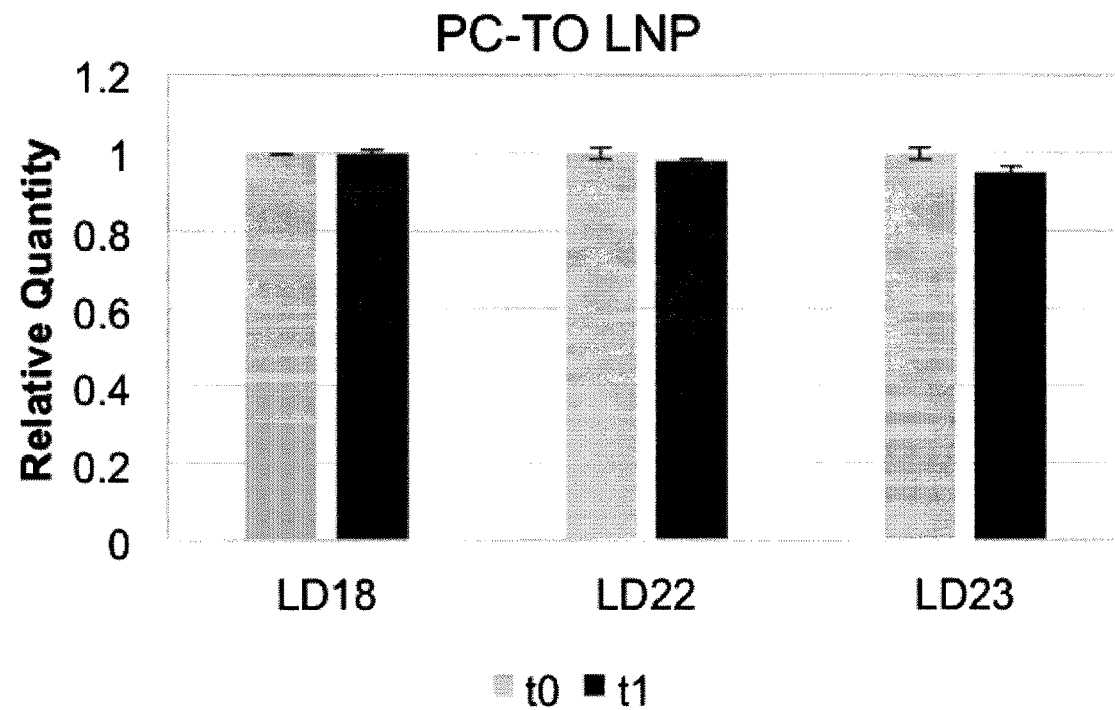

Biodegradation of LD-DTX prodrugs in lipid nanoparticles is shown in FIG. 5. LD-DTX were formulated into various lipid nanoparticle formulations and were subjected to mouse plasma incubation for 1 h at 37° C. Lipids were then extracted using a modified Bligh-Dyer & Folsch method and then subjected to UHPLC analyses for quantitation. As in the case of relatively hydrophobic LD-DEX prodrugs, LD-DTX prodrugs (LD10-, LD18-, LD22-, and LD23-DTX) were largely not degraded after 1 h incubation in mouse plasma.

Figure 6A:
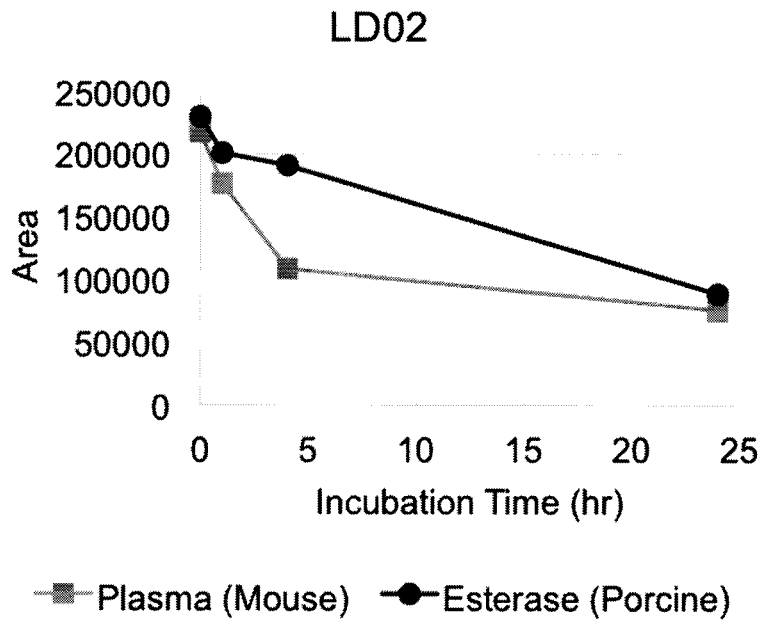
FIG. 6 shows the biodegradation of LD02 in LNP over time, wherein (A) shows LD02 prodrug was formulated into LNP and then subjected to incubation in either mouse plasma or purified porcine esterase over time and the amount of residual LD02 prodrug was analyzed by UPLC at time 0, 2, 4 and 24 h; and in (B) a UPLC chromatogram of LD02 is shown without incubation with plasma or esterase, LD02 incubated with esterase for 24 h, or LD02 incubated with mouse plasma for 24 h (Arrows indicate intact LD02 or dexamethasone (DEX)).
Figure 6B:
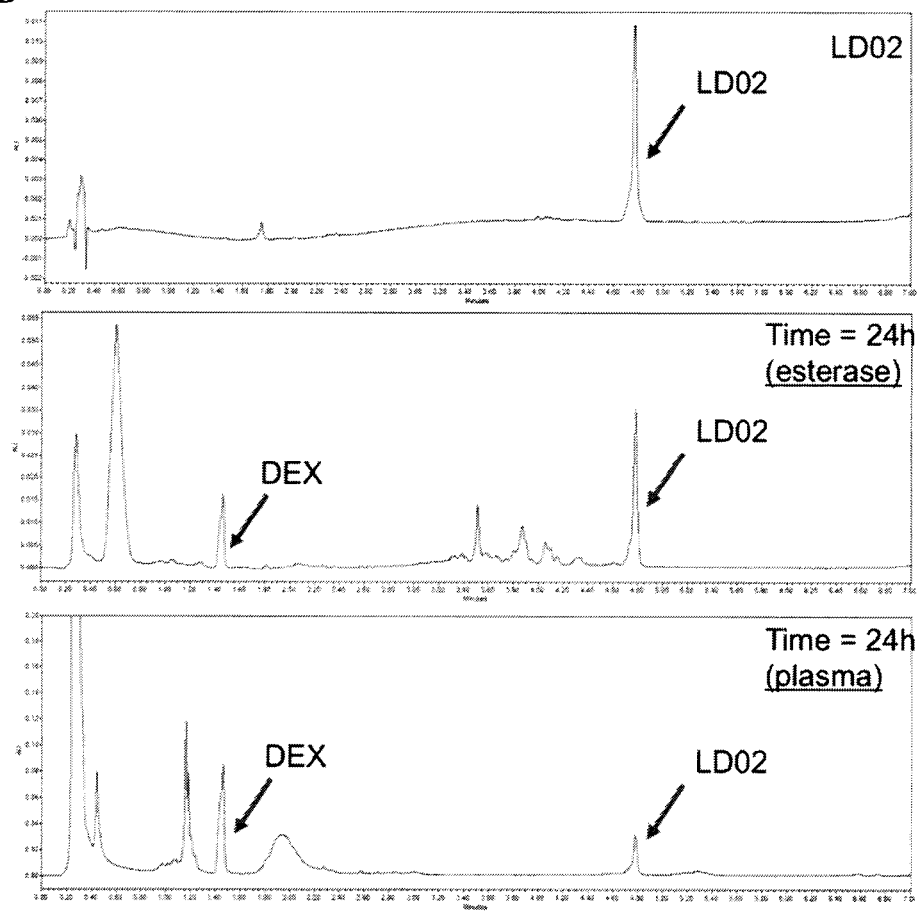
Figure 7A:
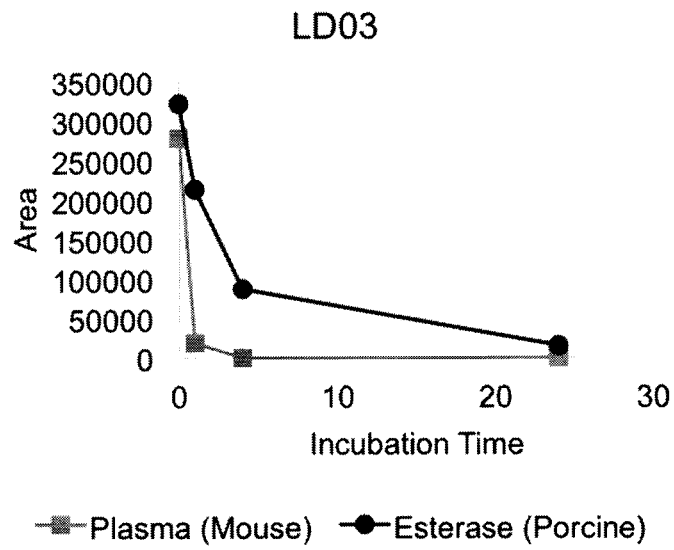
FIG. 7 shows the biodegradation of LD03 in LNP over time, wherein (A) shows LD03 prodrug was formulated into LNP and then subjected to incubation in either mouse plasma or purified porcine esterase over time and the amount of residual LD03 prodrug was analyzed by UPLC at time 0, 2, 4 and 24 h; and in (B) a UPLC chromatogram of LD03 is shown without incubation with plasma or esterase, LD03 incubated with esterase for 24 h, or LD03 incubated with mouse plasma for 24 h (Arrows indicate intact LD02 or dexamethasone (DEX)).
Figure 7B:
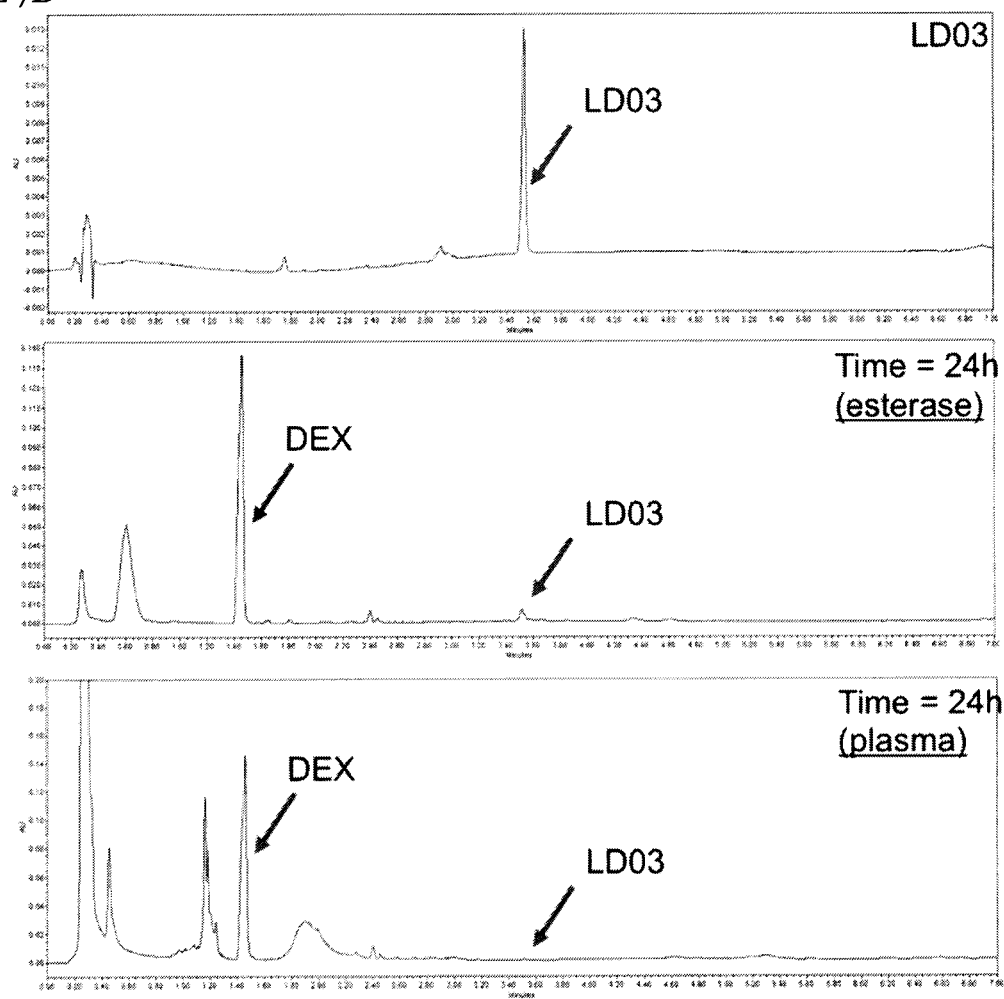
Figure 8A:
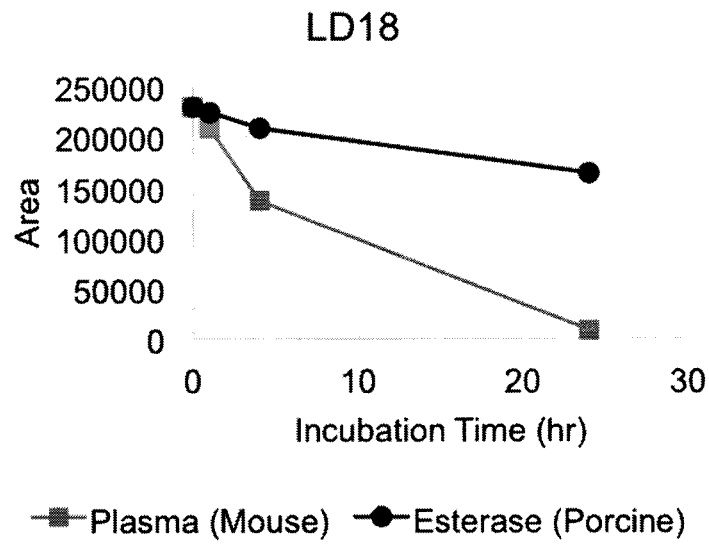
FIG. 8 shows the biodegradation of LD18 in LNP over time, wherein (A) shows LD18 prodrug was formulated into LNP and then subjected to incubation in either mouse plasma or purified porcine esterase over time and the amount of residual LD18 prodrug was analyzed by UPLC at time 0, 2, 4 and 24 h; and in (B) a UPLC chromatogram of LD18 is shown without incubation with plasma or esterase, LD18 incubated with esterase for 24 h, or LD18 incubated with mouse plasma for 24 h (Arrows indicate intact LD18 or docetaxel (DTX)).
Figure 8B:
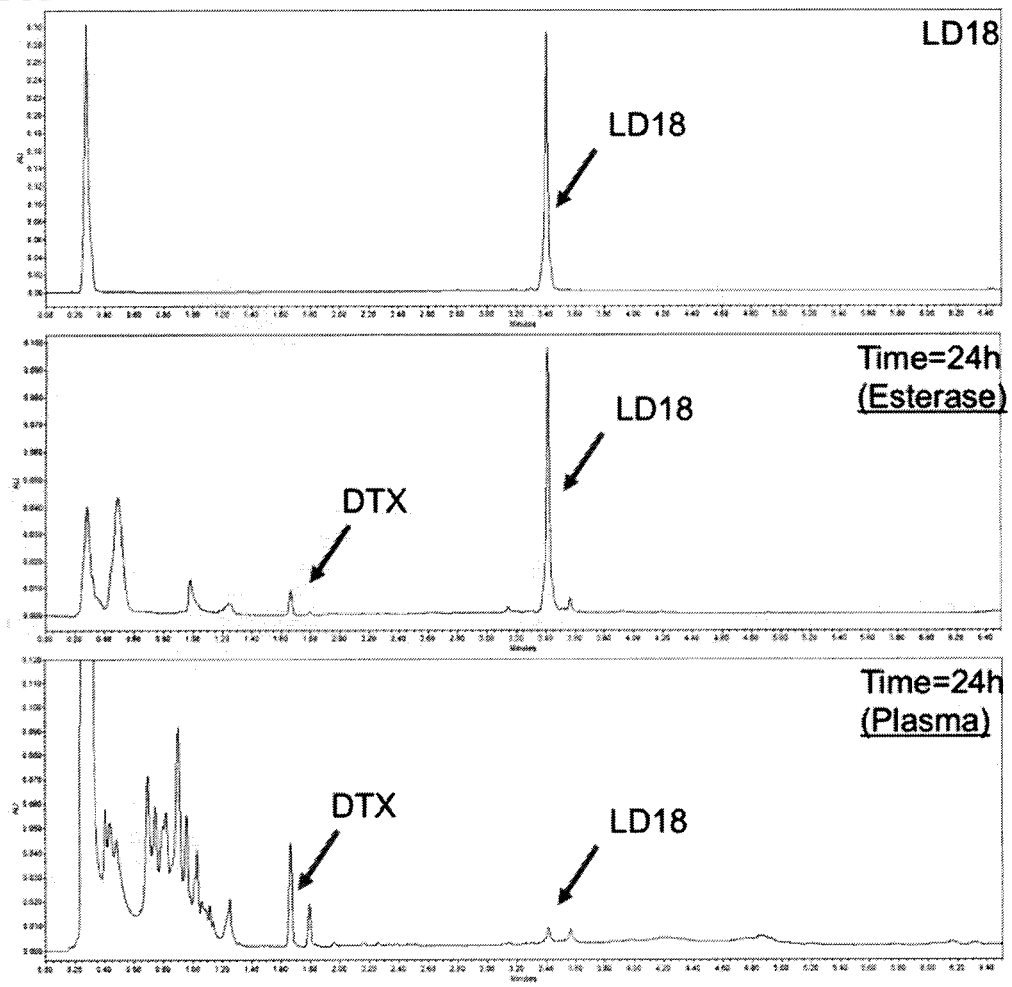
Figure 9A:
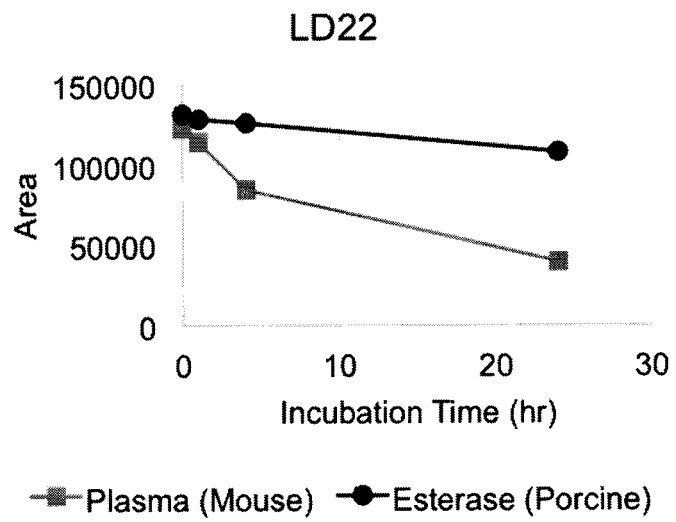
FIG. 9 shows the biodegradation of LD22 in LNP over time, wherein (A) shows LD22 prodrug was formulated into LNP and then subjected to incubation in either mouse plasma or purified porcine esterase over time. The amount of residual LD22 prodrug was analyzed by UPLC at time 0, 2, 4 and 24 h; and in (B) a UPLC chromatogram of LD22 is shown without incubation with plasma or esterase, LD22 incubated with esterase for 24 h, or LD22 incubated with mouse plasma for 24 h (Arrows indicate intact LD22 or docetaxel (DTX)).
Figure 9B:
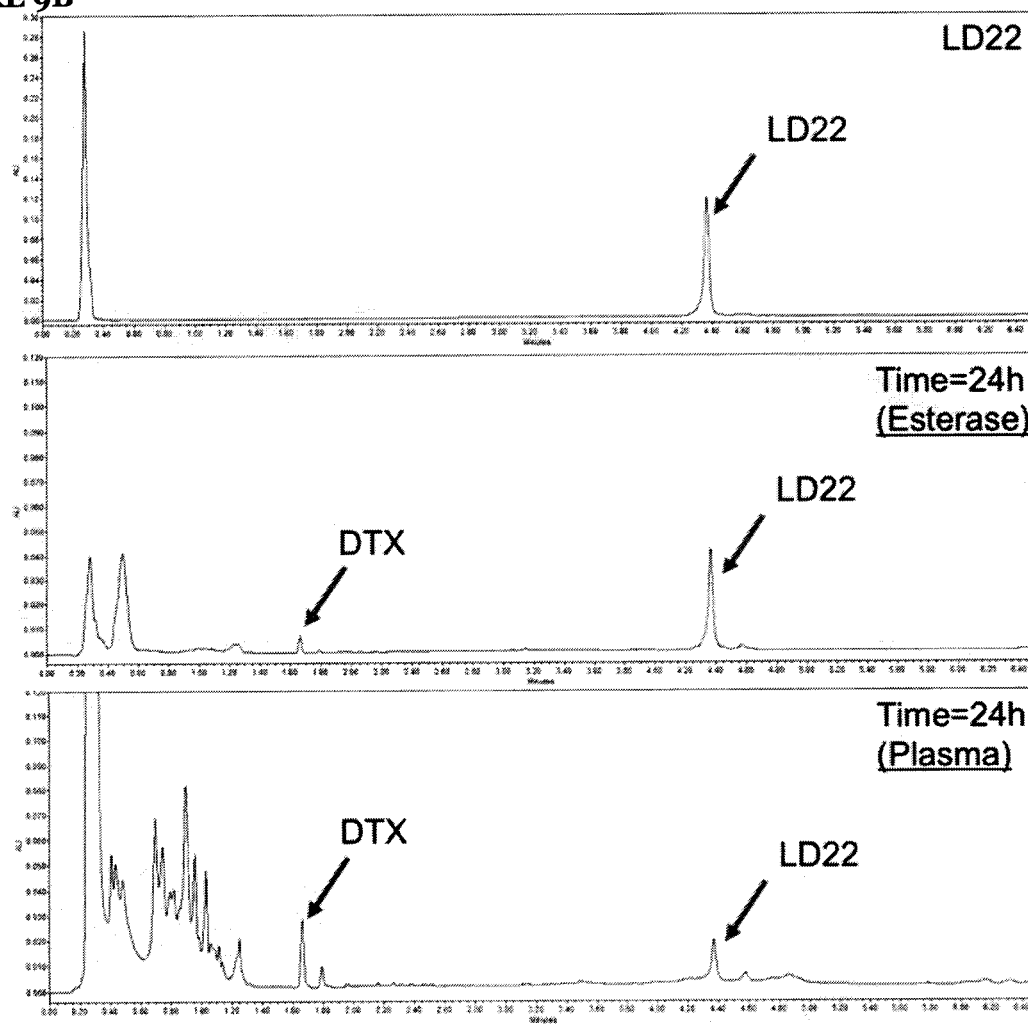

In order to demonstrate that the active drug can be released from the lipid-linked prodrug upon digestion at the biodegradable linker, representative prodrugs from the LD-DEX and LD-DTX series were formulation into lipid nanoparticles and subjected to either purified esterase or mouse plasma incubation over 24 h (FIG. 6 to FIG. 9). As shown in FIG. 6 and FIG. 7, both LD02- and LD03-DEX were progressively degraded over 24 h. As demonstrated above, LD03-DEX, which is less hydrophobic than LD02-DEX, was degraded at a faster rate than LD02-DEX. In addition, while the LD02 or LD03 prodrug peak is diminished over time, a peak corresponding to active dexamethasone (DEX) appeared in the chromatograms after 24 h incubation in either purified esterase or mouse plasma indicating that the active DEX is released (FIG. 6 and FIG. 7). Similarly, active docetaxel (DTX) was observed in the chromatograms of LD18- and LD22-DTX following 24 h in esterase or plasma incubation (FIG. 8 and FIG. 9).

Figure 10A:
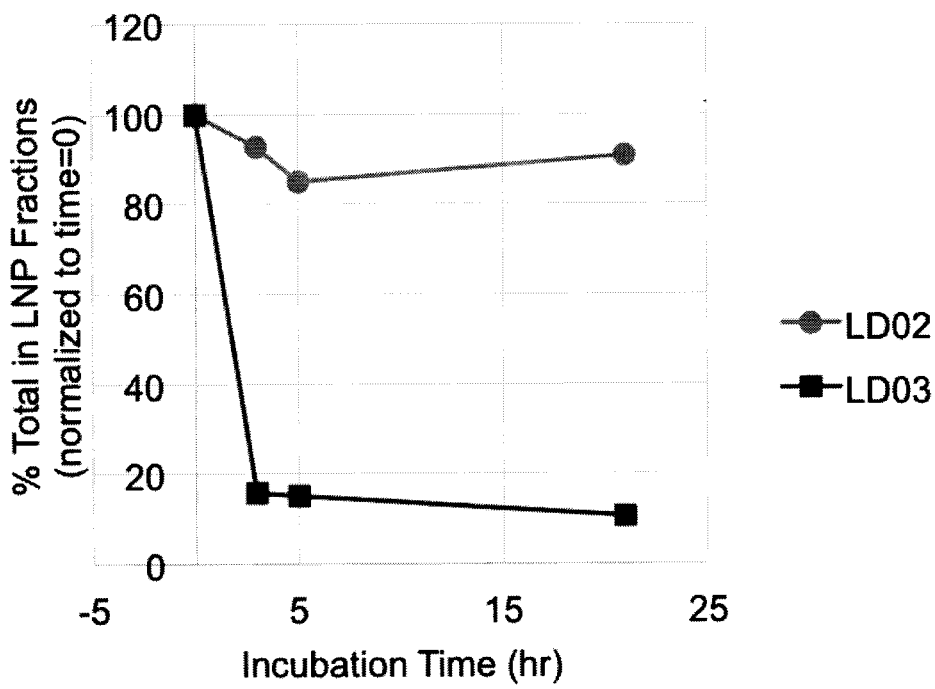
FIG. 10 shows that LD-DEX prodrug dissociation from LNP correlates with predicted hydrophobicity LD02 and LD03 DEX prodrugs were formulated in either (A) PC-Chol LNP or (B) ionizable LNP, and then subjected to incubation in human plasma over 24 h, and LNP was isolated by column chromatography before the residual amount of each prodrug at time 0, 3, 5 and 24 h was determined by UPLC analyses—LD02 dissociates from LNP at a slower rate than that of LD03.
Figure 10B:
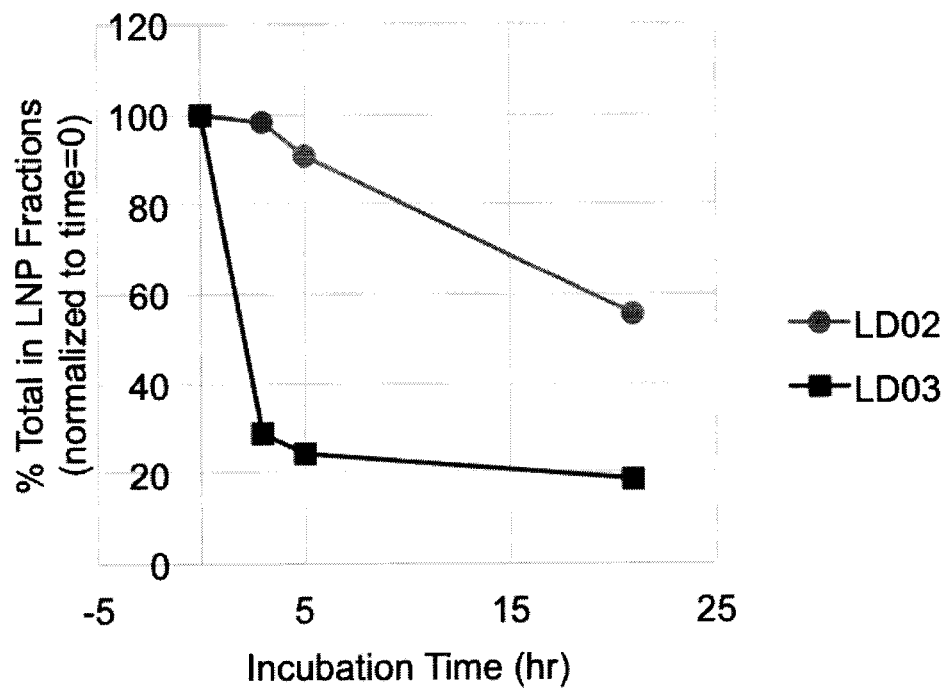
Figure 11A:
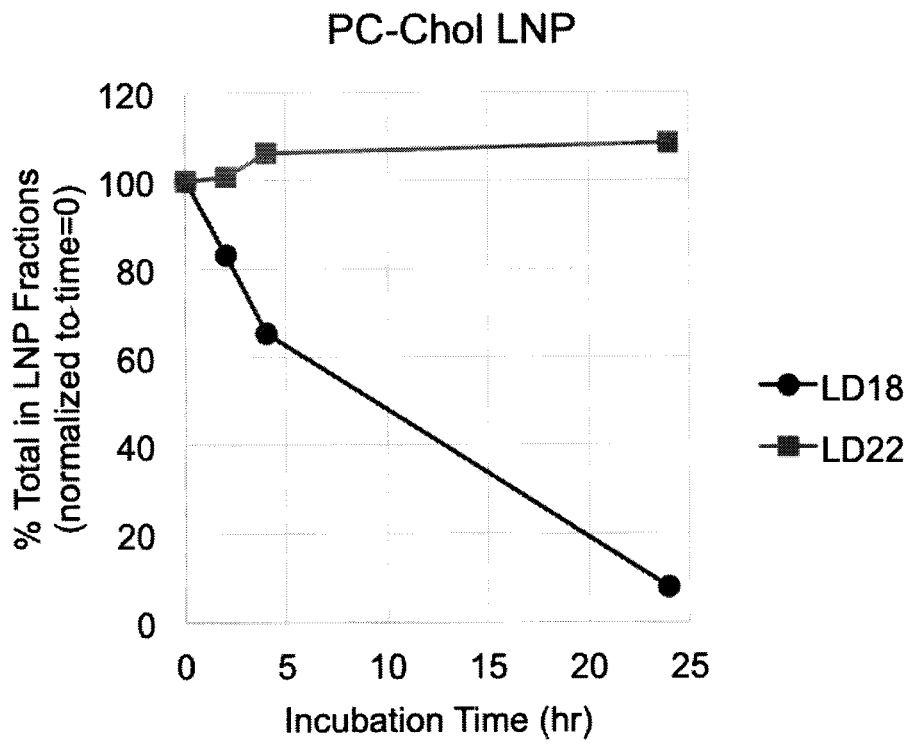
FIG. 11 shows LD-DTX prodrug dissociation from LNP correlates with predicted hydrophobicity LD18 and LD22 DTX prodrugs were formulated in either (A) PC-Chol LNP or (B) ionizable LNP, and then subjected to incubation in human plasma over 24 h, and LNP was isolated by column chromatography before the residual amount of each prodrug at time 0, 3, 5 and 24 h was determined by UPLC analyses— LD18 dissociates from LNP faster than LD22.
Figure 11B:
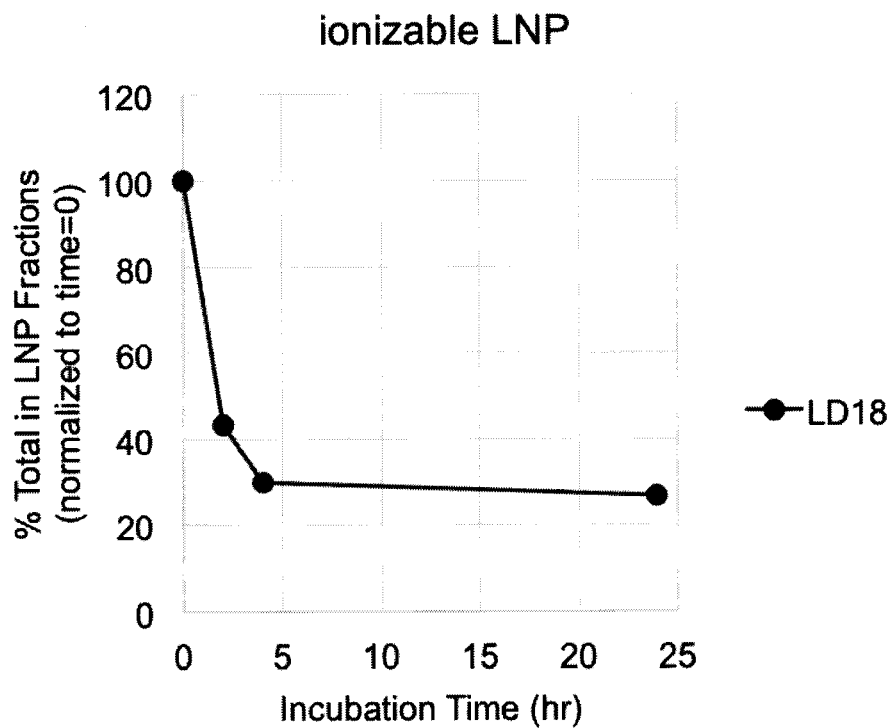

The hydrophobicity may also affect the efficient dissociation from lipid formulations. In order to detect and quantify prodrug dissociation from lipid nanoparticles, formulations containing lipid-linked prodrugs were incubated in human plasma over 24 h and then were subjected to size exclusion chromatography to recover lipid nanoparticle fractions. Lipids were extracted from these fractions using the modified Bligh-Dyer & Folsch method and then were analyzed by UHPLC to determine residual amount of prodrug (FIG. 10 and FIG. 11). Human plasma was used in these lipid dissociation experiments to remove the contribution of degradation by esterases as human plasma is known to contain substantially less carboxylesterase activity than mouse plasma. As shown in FIG. 10, LD02-DEX (with a higher hydrophobicity index than LD03-DEX) dissociated from lipid nanoparticles at a slower rate than LD03-DEX. Similar phenomenon was observed for LD-DTX series. LD18-DTX (less hydrophobic than LD22-DTX) dissociated at a faster rate from lipid nanoparticles than LD22-DTX (FIG. 11).

Example 4

Design and Synthesis of Alternative Lipid-linked Prodrugs

Additional lipid-liked prodrugs may be synthesized using the methods described herein, including prodrugs containing other active drugs such as methotrexate (LD01-METH), tacrolimus (LD15-TAC), tofacitinib (LD01-TFN), cabazitaxel (LD01-CTX), and ruxolitinib (LD01-RXN). Of the prodrugs that have been made and designed to conform to these design "rules", all have been found to be efficiently incorporated and retained in LNP as predicted.

Example 5

Anti-Inflammatory Effects of Lipid-Linked Prodrugs in Mouse and Cellular Models of Immune Stimulation In order to demonstrate the utility of LD-DEX prodrugs, both mouse and cellular models of immune stimulation were used. In particular, experimental models of immune stimulation mediated by nucleic acids are facile and provide reliable measurements of immune responses.

Nucleic acid-based macromolecules such as antisense oligonucleotides for gene silencing, RNAs for gene regulation/gene expression or plasmid DNA for gene expression/gene editing are promising therapeutics. However, they are potent inducers of the innate immune response in vertebrates [Sakurai et al. (2008) and Barbalat et al. (2011)]. Lipid or polymer-based nanoparticles are often used as delivery systems to protect these macromolecules from degradation in biological fluids and carry them to site of disease and intracellular site of action. Despite the obvious benefits, these systems give rise to "flu-like" symptoms and hypotension from the activation of toll-like receptors and increases in serum cytokine levels in animals and patients, even for payloads that have been engineered to minimize immune-stimulatory potential [Barros et al. (2012); Kumar et al. (2014); and Abe et al. (2011);]. Hence, systemic administration of lipid nanoparticles containing nucleic acid-based macromolecules such as antisense, mRNA and plasmid DNA can be valuable model to demonstrate the anti-inflammatory effects of LD-DEX prodrugs in vivo.

Figure 12:
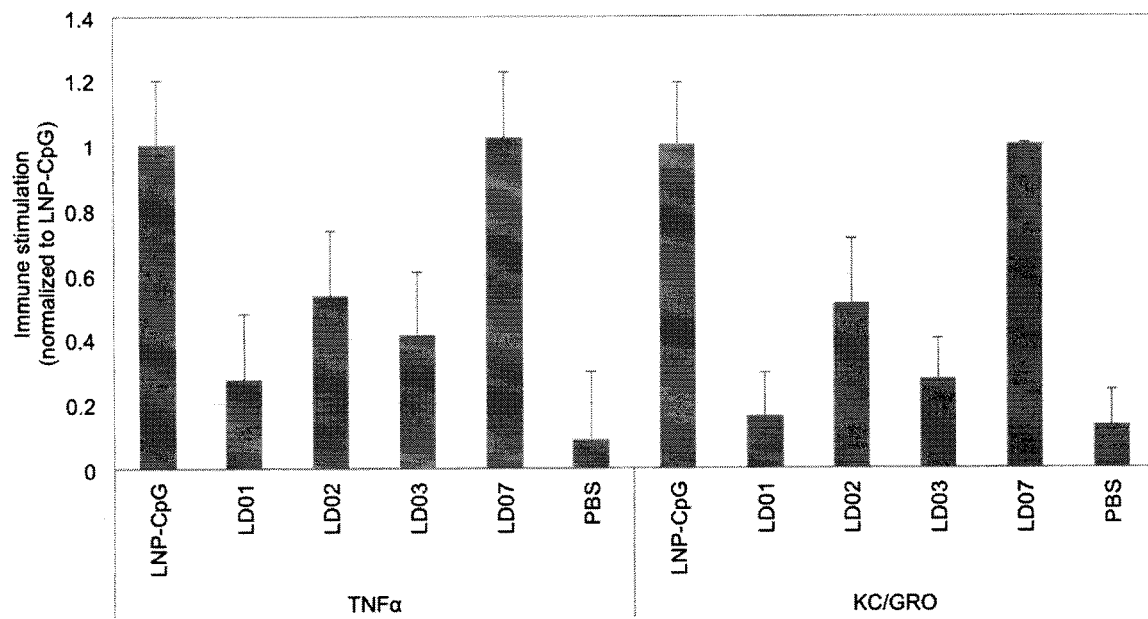
FIG. 12 shows LD-DEX prodrugs suppress the immunostimulatory effects of LNP-CpG in mice, when LD01, LD02, LD03 or LD07 was formulated into LNP containing immune stimulatory CpG oligonucleotides, mice were injected with either PBS or LNP-CpG with or without LD-DEX prodrugs at 10 mg/kg of CpG, whereby blood was collected 2 h post injection and the levels of TNFα and KC/GRO were measured, the data was normalized to the cytokine levels of mice treated with control LNP-CpG without LD-DEX and levels below 1 indicate immune suppression (Error bars represent standard deviation derived from at least 3 animals).
Figure 13:
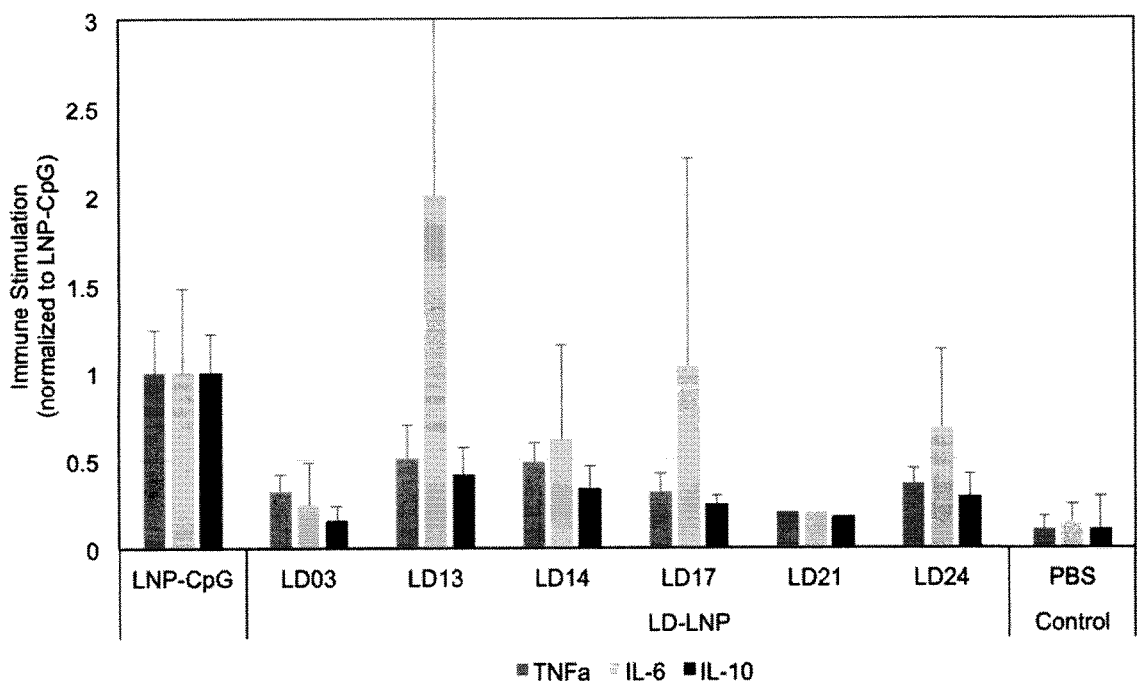
FIG. 13 shows LD-DEX prodrugs suppress the immunostimulatory effects of LNP-CpG in mice, wherein LD03, LD13, LD14, LD17, LD21 or LD24 was formulated into LNP containing immune stimulatory CpG DNA oligonucleotides, mice were injected with either PBS or LNP-CpG with or without LD-DEX prodrugs at 10 mg/kg of CpG and blood was collected 2 h post injection before the levels of TNFα, IL6 and IL10 were measured, the data was normalized to the cytokine levels of mice treated with control LNP-CpG without LD-DEX and levels below 1 indicate immune suppression (Error bars represent standard deviation derived from at least 3 animals).

LD-DEX prodrugs were formulated into lipid nanoparticles containing an immune-stimulatory CpG-containing DNA oligonucleotide (FIG. 12, FIG. 13 and FIG. 15) or mRNA (FIG. 14) using a rapid mixing technique as indicated in Materials and Methods. Using this technique, nucleic acids macromolecules are embedded in the internal aqueous space of lipid nanoparticles. All formulations had particle diameters of approximately 50 nm with polydispersity indices (PdI)<0.1 indicating that incorporation of the LD-DEX into the LNP did not significantly affect particle size or homogeneity. Mice injected with lipid nanoparticles containing immune-stimulatory CpG DNA oligonucleotide (LNP-CpG) showed elevated levels of plasma TNFα and KC/GRO (FIG. 12) 2 h post administration. In contrast, incorporation of LD01-, LD02-, and LD03-DEX in lipid nanoparticles resulted in marked reduction in cytokine levels as compared to control LNP-CpG. As expected, LD07-DEX containing non-hydrolysable linker did not exhibit any immunosuppressive effects. FIG. 13 shows other LD-DEX prodrugs that contain hydrolysable linker (LD13-, LD14-, LD17-, LD21-, and LD24-DEX) were able to suppress plasma cytokine (TNFα, IL-6 and IL-10) levels in comparison to control LNP-CpG. These results demonstrated that active dexamethasone was released from lipid-linked prodrugs to reduce immune responses caused by immune-stimulatory CpG DNA oligonucleotide containing lipid nanoparticles.

Figure 14:
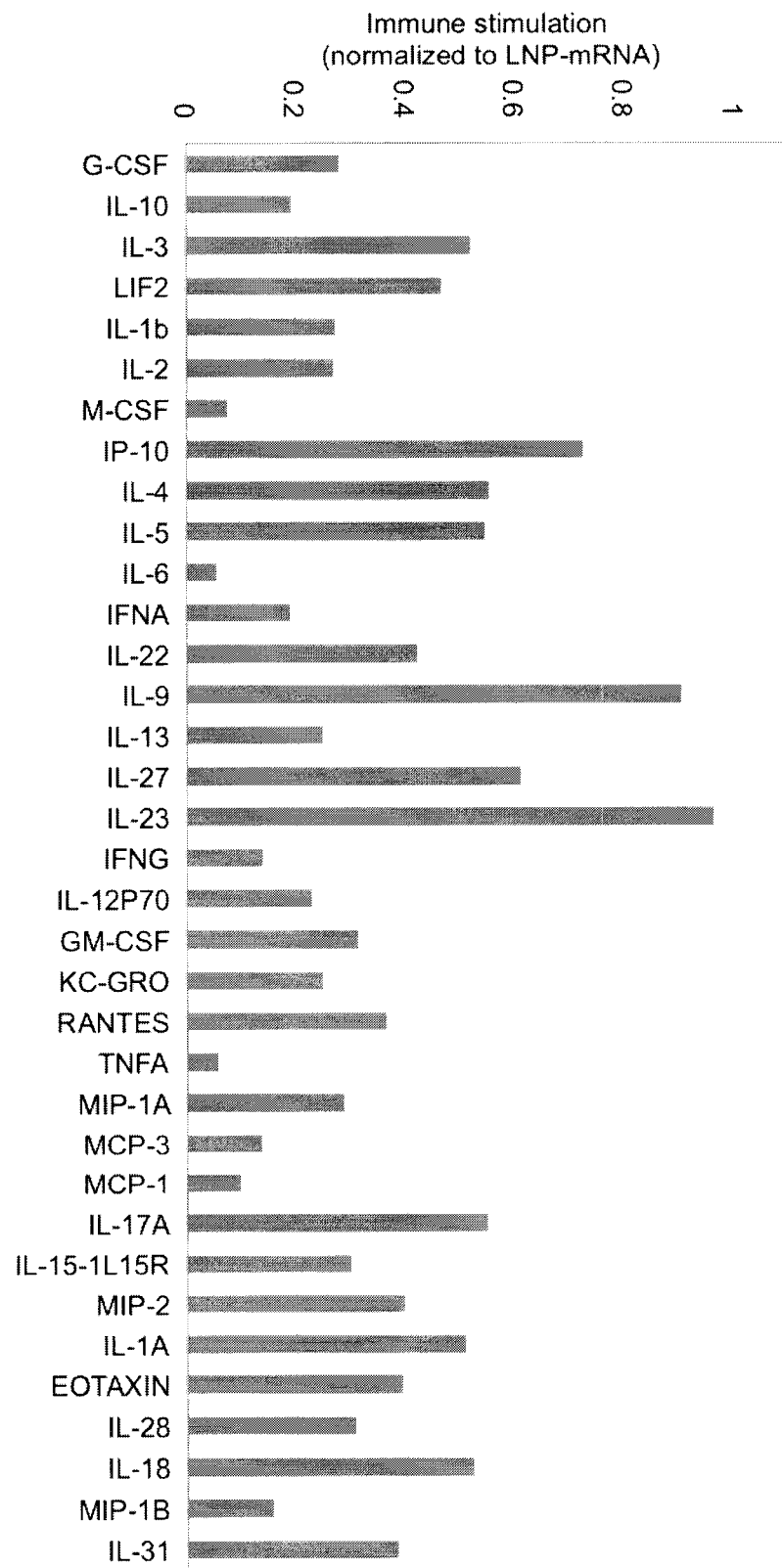
FIG. 14 shows that LD03 suppresses the immunostimulatory effects of LNP-mRNA in mice, wherein the formulation with or without LD03 was injected in mice at 3 mg/kg of mRNA, blood was collected 2 h post injection and the levels of various cytokines were determined, wherein the data was normalized to the cytokine levels of mice treated with control LNP-mRNA without LD03 and levels below 1 indicate immune suppression (Error bars represent standard deviation derived from at least 3 animals).

Mouse model of immune stimulation mediated by mRNA is shown in FIG. 14. LD03-DEX was formulated into lipid nanoparticles containing an unmodified 1.7 kb mRNA coding for firefly luciferase. Blood was collected 2 h post-injection and plasma cytokine levels were determined. Animals treated with LD03-DEX showed significantly reduced levels of a number of plasma cytokines as compared to control group injected with LNP-mRNA containing no LD-DEX prodrug. These results indicated that active dexamethasone was released from lipid-linked prodrugs to reduce immune responses caused by mRNA containing lipid nanoparticles.

Figure 15:
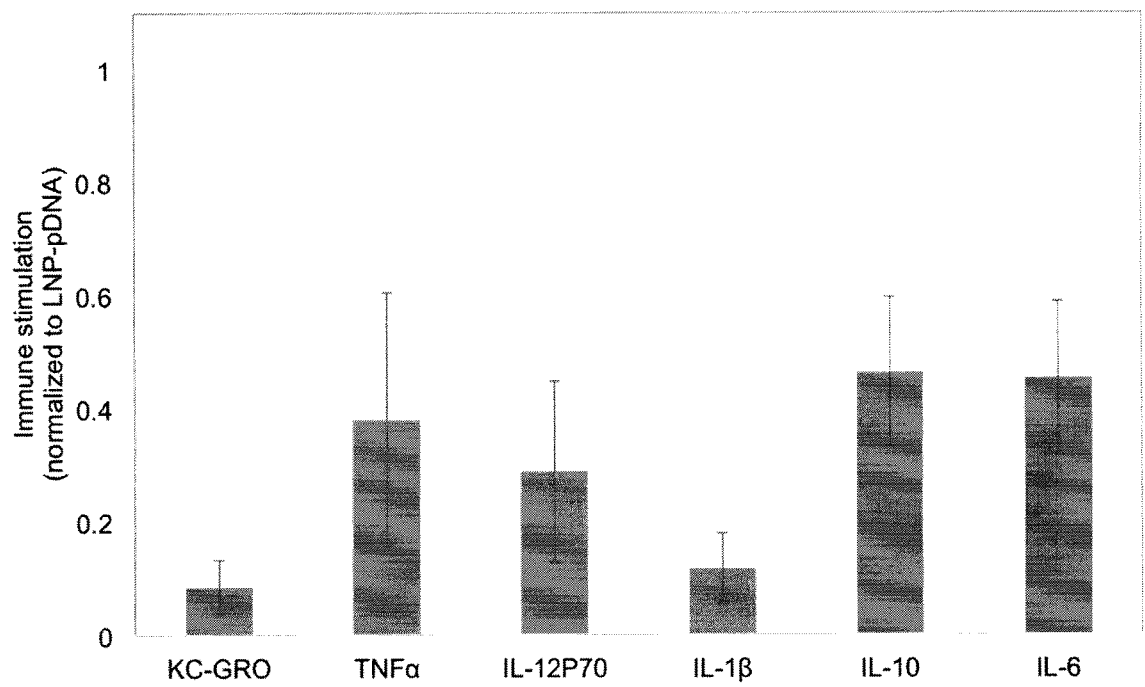
FIG. 15 shows that LD03 suppresses the immunostimulatory effects of LNP-pDNA in mice, wherein plasmid DNA LNP (LNP-pDNA) with or without LD03 was administered intravenously in mice at 1 mg/kg of pDNA, blood was collected at 2 h post injection and the levels of various cytokines were measured, wherein data was normalized to the cytokine levels of mice treated with control LNP-pDNA without LD03 and levels below 1 indicate immune suppression (Error bars represent standard deviation derived from at least 4 animals).

Plasmid DNA (pDNA) is known to stimulate the innate immunity via the stimulation of TLR receptors. In order to demonstrate immunosuppressive effects of LD-DEX in vivo, mouse model of immune stimulation mediated by pDNA was performed (FIG. 15). In this model, pDNA encoding firefly luciferase was formulated into lipid nanoparticles with or without LD03-DEX, and the resulted formulations were injected in mice. Plasma cytokine levels were determined 2 h post injection. Similar to the other immune stimulation models described above, control LNP without LD03-DEX was able to stimulate expression of various cytokines. In contrast, LNP containing LD03-DEX efficiently suppressed cytokine levels suggesting that active dexamethasone was cleaved from lipid-linked prodrug to reduce immune responses mediated by pDNA.

Figure 16:
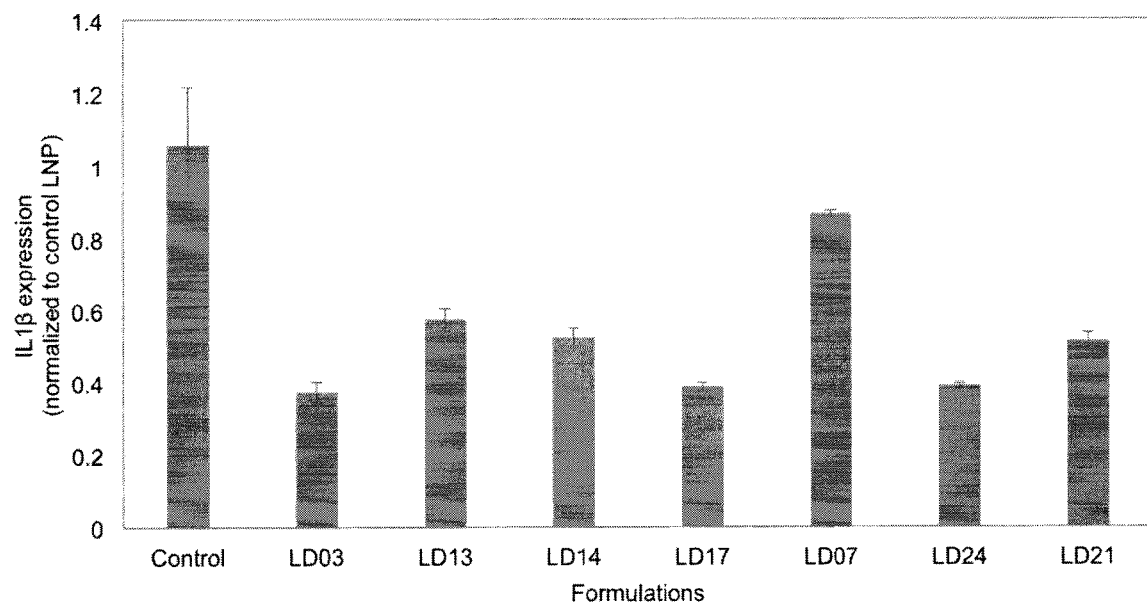
FIG. 16 shows that LD-DEX prodrugs suppress the immunostimulatory responses in Raw264.7 cells treated with lipopolysaccharide (LPS), wherein cells were incubated in medium containing 2 ng/mL of LPS and LNP formulation containing no prodrug (control), LD03, LD07, LD13, LD14, LD17, LD21 and LD24 for 4 h. the cells were then harvested for RNA isolated and levels of IL1β were determined by qRT-PCR, and the data was normalized to cells treated with control LNP without prodrug (Error bars represent standard deviation of at least three experiments).
Figure 17A:
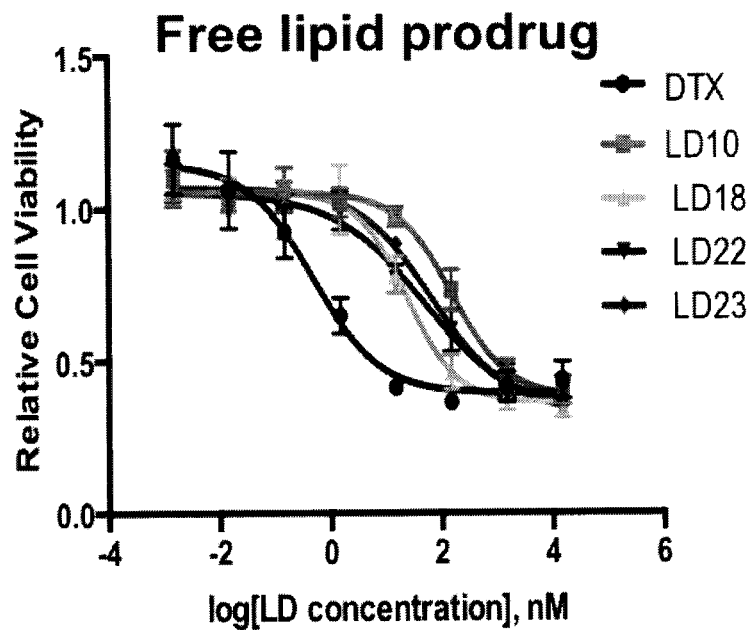
FIG. 17 shows that LD-DTX prodrugs inhibit the growth of ovarian cancer cells, in comparing LD10, LD18, LD22 or LD23, which was formulated in (D) PC-Chol, (C) PC-TO, (B) ionizable LNP or (A) free lipid prodrug, then Ovcar3 cells were incubated with PBS, free docetaxel, free LD-DTX prodrugs, or LNP with or without LD-DTX prodrugs at 0 to 15 μM of docetaxel and cell viability was determined after 48 h and reported as relative value normalized to the viability of cells treated with PBS (Error bars represent standard deviation of at least three experiments).
Figure 17B:
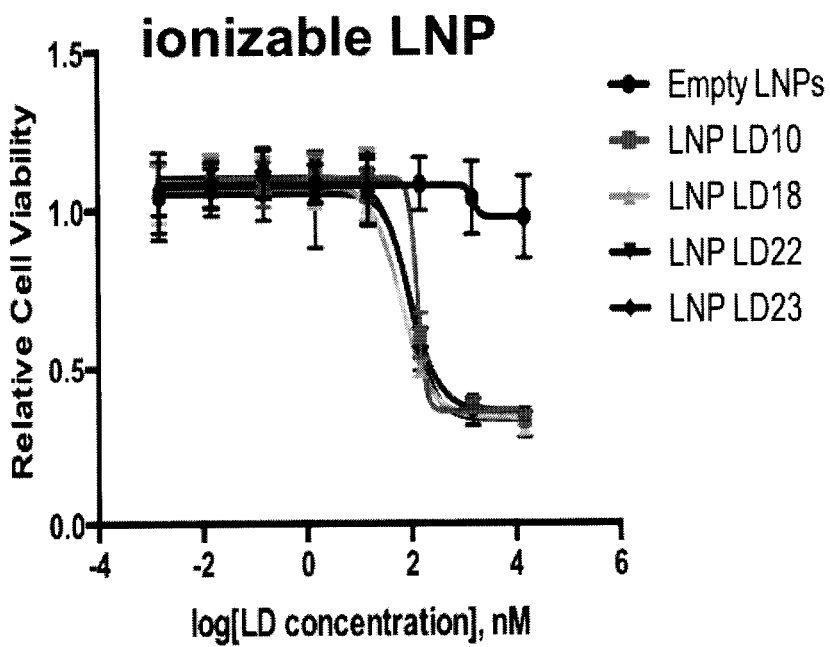
Figure 17C:
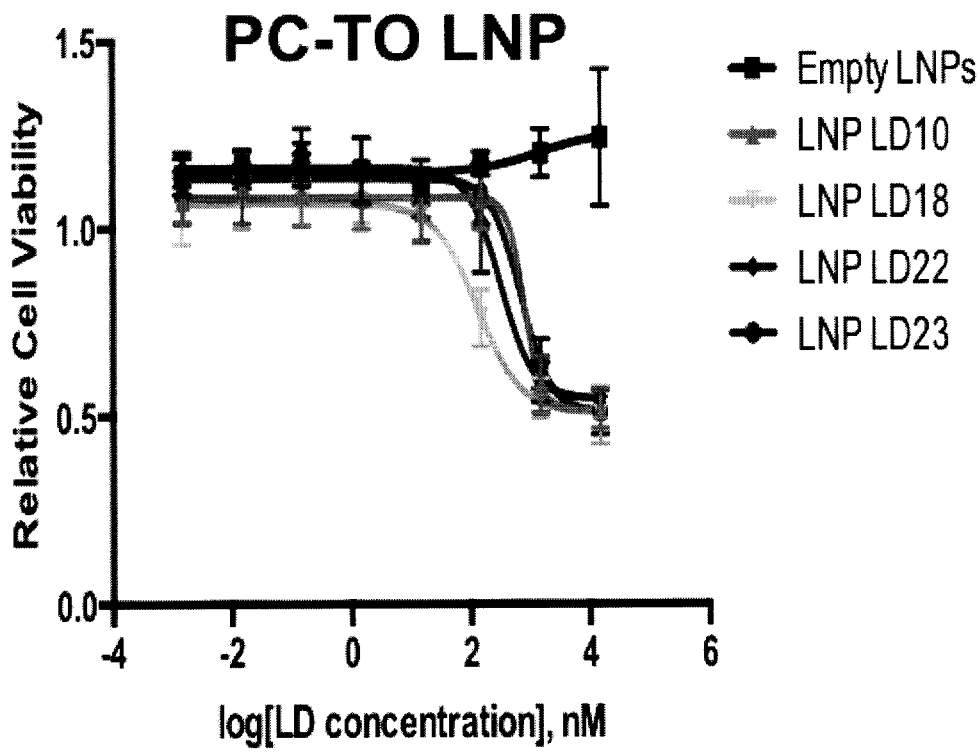
Figure 17D:
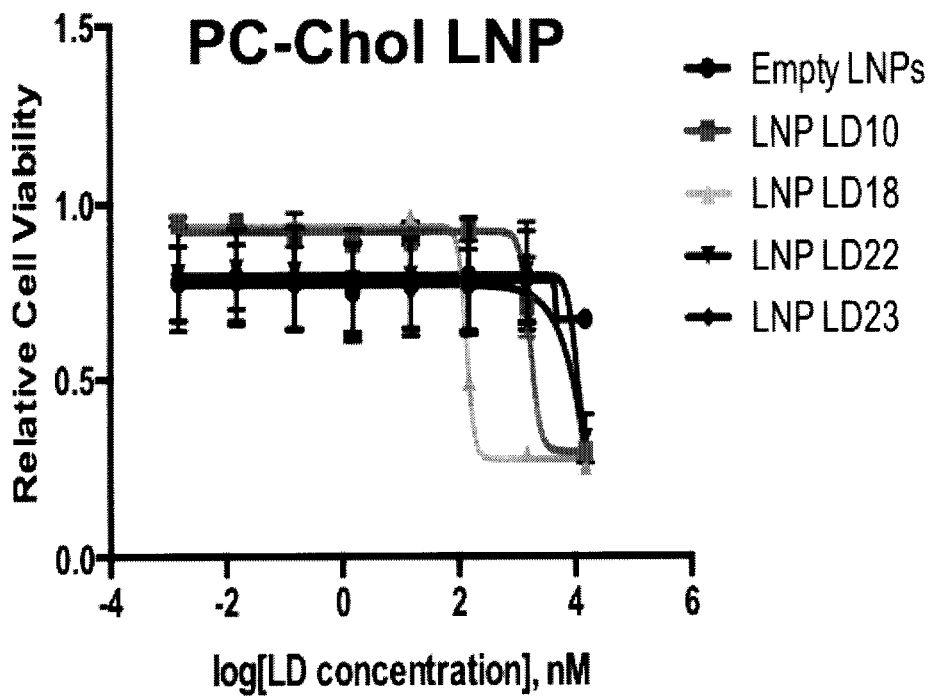

Cellular model of immune stimulation mediated by lipopolysaccharide (LPS) is shown in FIG. 16. A subset of LD-DEX prodrugs was formulated into lipid nanoparticles. Macrophage RAW264.7 incubated with LPS and control formulation (made without any prodrug) showed elevated cytokine TUB expression. In contrast, LD03-, LD13-, LD14-, LD17-, LD21-, and LD24-DEX prodrug containing lipid nanoparticles were able to reduce IL1β expression in comparison to control formulation without any prodrug. As expected, LD07-DEX showed IL1β expression at a similar level to control.

Example 6

Anti-Proliferation Effects of Lipid-Linked Prodrugs in Cancer Cells

The anti-proliferative effects of LD-DTX prodrugs were demonstrated in OVCAR3 ovarian cancer cells. LD-DTX prodrugs (LD10-, LD18-, LD22-, or LD23-DTX) were formulated into various types of lipid nanoparticles as described in Materials and Methods. Cells were treated with various concentrations of free docetaxel, free LD-DTX prodrugs or formulations with or without LD-DTX for 48 h and cell viability was analyzed by MIT assay. As shown in FIG. 17, all LD-DTX prodrugs were able to suppress cancer cell proliferation. As expected, the amount of free docetaxel needed to suppress cell growth was much lower than all the other test articles. Interestingly, LD18-DTX showed the lowest IC50 (concentration needed to inhibit 50% growth) in comparison to other prodrugs. This is likely due to the fact that LD18-DTX is the least hydrophobic, allowing it to be dissociated and/or accessed by esterases more easily than the other prodrugs.

TABLE 7

IC50 Values for LD10, LD18, LD22 and LD23
IC50 (nM)

|  | Docetaxel | LD10 | LD18 | LD22 | LD23 |
|---|---|---|---|---|---|
| Free drugs | 0.4876 | 155.8 | 23.92 | 51.73 | 64.55 |
| PC-Chol LNP | — | 373.9 | 37.31 | ~1551 | ~15584 |

TABLE 7-continued

IC50 Values for LD10, LD18, LD22 and LD23
IC50 (nM)

|  | Docetaxel | LD10 | LD18 | LD22 | LD23 |
|---|---|---|---|---|---|
| ionizable LNP | — | 132.7 | 63.99 | 92.98 | 99.91 |
| PC-TO LNP | — | 791.2 | 130.9 | 315.2 | 691.6 |

Compounds described herein may be synthesized as described herein, using modified methods described herein or by methods known to a person of skill in the art.

Although various embodiments of the invention are disclosed herein, many adaptations and modifications may be made within the scope of the invention in accordance with the common general knowledge of those skilled in this art. Such modifications include the substitution of known equivalents for any aspect of the invention in order to achieve the same result in substantially the same way. Numeric ranges are inclusive of the numbers defining the range. The word "comprising" is used herein as any open-ended term, substantially equivalent to the phrase "including, but not limited to", and the words "comprise" and "comprises" have a corresponding meaning. As used herein, the singular forms "a", "an" and "the" include plural referents unless the context clearly dictates otherwise. Thus, for example, reference to "a thing" includes more than one such thing.

Citation of references herein is not an admission that such references are prior art to the present invention nor does it constitute any admission as to the contents or date of these documents.

REFERENCES

1. Charrois, G. J. and T. M. Allen, Drug release rate influences the pharmacokinetics, biodistribution, therapeutic activity, and toxicity of pegylated liposomal doxorubicin formulations in murine breast cancer. Biochim Biophys Acta, 2004. 1663(1-2): p. 167-77.
2. Cui, J., et al., Direct comparison of two pegylated liposomal doxorubicin formulations: is AUC predictive for toxicity and efficacy? J Control Release, 2007. 118(2): p. 204-15.
3. Johnston, M. J., et al., Therapeutically optimized rates of drug release can be achieved by varying the drug-to-lipid ratio in liposomal vincristine formulations. Biochim Biophys Acta, 2006. 1758(1): p. 55-64.
4. Nichols, J. W. and D. W. Deamer, Catecholamine uptake and concentration by liposomes maintaining p/gradients. Biochim Biophys Acta, 1976. 455(1): p. 269-71.
5. Mayer, L. D., et al., Techniques for encapsulating bioactive agents into liposomes. Chem Phys Lipids, 1986. 40(2-4): P. 333-45.
6. Allen, T. M. and P. R. Cullis, Liposomal drug delivery systems: from concept to clinical applications. Advanced Drug Delivery Reviews, 2013. 65(1): p. 36-48.
7. Mao, L., et al., Conjugation of two complementary anti-cancer drugs confers molecular hydrogels as a co-delivery system. Chem Commun (Camb), 2012. 48(3): P. 395-7.
8. Maclachlan, I. and P. Cullis, "Diffusible-PEG-Lipid Stabilized Plasmid Lipid Particles". Adv Genet, 2005. 53PA: p. 157-188.

9. Jeffs, L. B., et al., A scalable, extrusion-free method for efficient liposomal encapsulation of plasmid DNA. Pharm Res, 2005. 22(3): p. 362-72.
10. Bligh, E. G. and W. J. Dyer, A rapid method of total lipid extraction and purification. Can J Biochem Physiol, 1959. 37(8): p. 911-7.
11. Leung, A. K., et al., Lipid Nanoparticles Containing siRNA Synthesized by Microfluidic Mixing Exhibit an Electron-Dense Nanostructured Core. The journal of physical chemistry. C, Nanomaterials and interfaces, 2012. 116(34): p. 18440-18450.
12. Chatham, W. W. and R. P. Kimberly, Treatment of lupus with corticosteroids. Lupus, 2001. 10(3): p. 140-7.
13. Rhen, T. and J. A. Cidlowski, Antiinflammatory Action of Glucocorticoids—New Mechanisms for Old Drugs. New England Journal of Medicine, 2005. 353(16): p. 1711-1723.
14. Inaba, H. and C.-H. Pui, Glucocorticoid use in acute lymphoblastic leukemia: comparison of prednisone and dexamethasone. The Lancet Oncology, 2010. 11(11): p. 1096-1106.
15. Teuffel, O., et al., Dexamethasone versus prednisone for induction therapy in childhood acute lymphoblastic leukemia: a systematic review and meta-analysis. Leukemia, 2011. 25(8): p. 1232-1238.
16. Wilson, K. D., et al., The combination of stabilized plasmid lipid particles and lipid nanoparticle encapsulated CpG containing oligodeoxynucleotides as a systemic genetic vaccine. The journal of gene medicine, 2009. 11(1): p. 14-25.
17. Miyabo, S., et al., A comparison of the bioavailability and potency of dexamethasone phosphate and sulphate in man. Eur J Clin Pharmacol, 1981. 20(4): p. 277-82.
18. Rohdewald, P., et al., Pharmacokinetics of dexamethasone and its phosphate ester. Biopharm Drug Dispos, 1987. 8(3): p. 205-12.
19. Mossman, T. Rapid Colorimetric assay for cellular growth and survival: application to proliferation and cytotoxicity assays. Journal of Immunological Methods, 1983. 65: p. 55-63.
20. Sakurai, H., et al., Innate immune response induced by gene delivery vectors. International journal of pharmaceutics, 2008. 354: p. 9-15.
21. Barbalat, R., et al., Nucleic acid recognition by the innate immune system. Annu Rev Immunol, 2011. 29: p. 185-214.
22. Barros, S. A., et al., Safety profile of RNAi nanomedicines. Adv Drug Deliv Rev, 2012. 64: p. 1730-1737.
23. Abrams, M. T., et al., Evaluation of efficacy, biodistribution, and inflammation for a potent siRNA nanoparticle: effect of dexamethasone co-treatment. Mol Ther, 2010. 18: p. 171-180.
24. Kumar, V., et al., Shielding of lipid nanoparticles for siRNA delivery: impact on physicochemical properties, cytokine induction, and efficacy. Mol Ther Nucleic acids, 2014. 3, e210.
25. Abe, M.; Niibayashi, R.; Koubori, S.; Moriyama, I.; Miyoshi, H.; *Biochemistry* 2011, 50, 8383.
26. Ohwada, J.; Inouye, Y.; Kimura, M.; Kakisawa, H. *Bull. Chem. Soc. Jpn.* 1990, 63, 287.
27. Fieser, L; Fieser, M. *Reagents for Organic Synthesis* 1967, 581-595.
28. Lopez, S.; Simons, Jr.; S. S. *J. Med. Chem.* 1991, 34, 1726 and reference therein.
29. Lee, K.; Ren, T.; Cote, M.; Gholamreza, B.; Misasi, J.; Bruchez, A.; Cunningham, *J. ACS Med. Chem. Lett.* 2013, 4, 239.

What is claimed is:

1. A compound, the compound having the structure of Formula III:

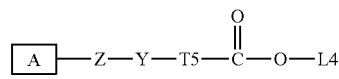

wherein:

A-Z is dexamethasone, wherein Z is an electronegative atom selected from N or O, such that the dexamethasone is represented by the formula A-Z—H when Z has lost an H to covalently bind to Y;

Y is $CH_2$ or $C(\!=\!O)$;

T5 is 0-6 carbon atoms; and

L4 is $C_9$-$C_{29}$ linear or branched carbon chain, having one or more, cis or trans C=C double bonds and optionally substituted with OH or has the Formula V:

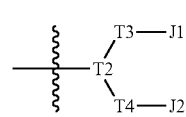

wherein,

T2 is 1-4 carbon atoms;

T3 is 0-4 carbon atoms;

T4 is 0-4 carbon atoms;

J1 is —O—C($=$O)-L1;

J2 is —COOH, —OH, —$NH_2$, —SH, —$NMe_2$, or —NHMe; and

L1 is $C_9$-$C_{29}$ linear or branched carbon chain, optionally having one or more, cis or trans C=C double bonds and optionally substituted with OH.

2. The compound of claim 1, wherein the compound has the structure of Formula II:

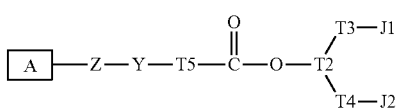

wherein:

Y is $CH_2$ or $C(\!=\!O)$;

T1 is 0-4 carbon atoms;

T2 is 1-3 carbon atoms; and

J2 is —COOH, —OH, —$NH_2$, —$NMe_2$, or —NHMe.

3. The compound of claim 1, wherein the compound has the structure of Formula III:

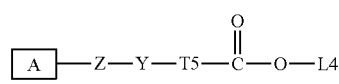

wherein:
Y is CH$_2$ or C(=O); and
T5 is 0-4 carbon atoms.

4. The compound of claim 1, wherein L4 is C$_9$-C$_{29}$ linear or branched carbon chain, having one or more, cis or trans C=C double bonds.

5. The compound of any one of claim 1, wherein Y is CH$_2$ or C(=O); and T5 are 0-2 carbon atoms.

6. A pharmaceutical composition, the pharmaceutical composition comprising a compound of claim 1 and a pharmaceutically acceptable carrier.

7. A method for suppressing immunity, the method comprising administering a compound of claim 1 to a subject in need thereof.

8. The compound of claim 1, wherein the compound is selected from one or more of the following:

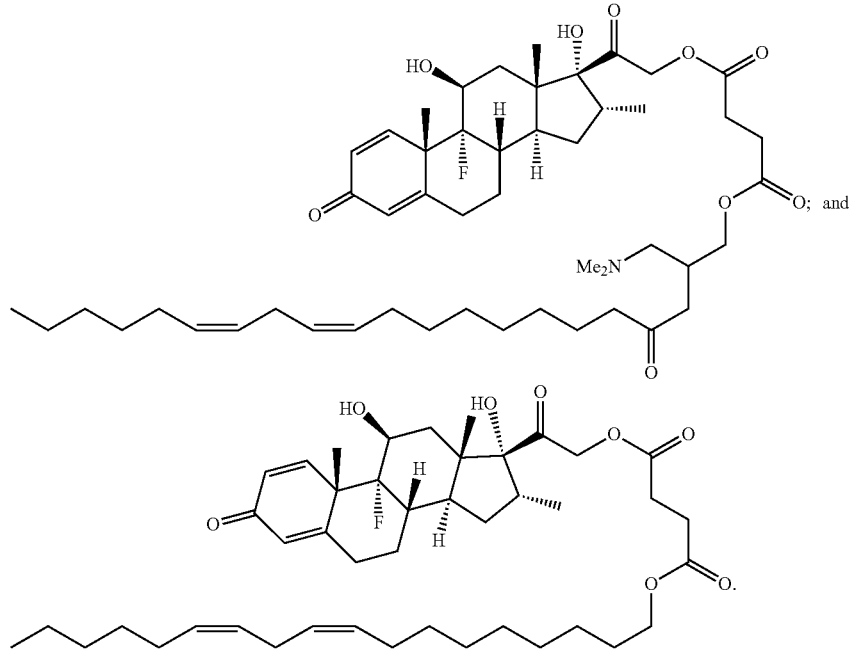

9. The method of claim 7, wherein the compound is selected from one or more of the following:

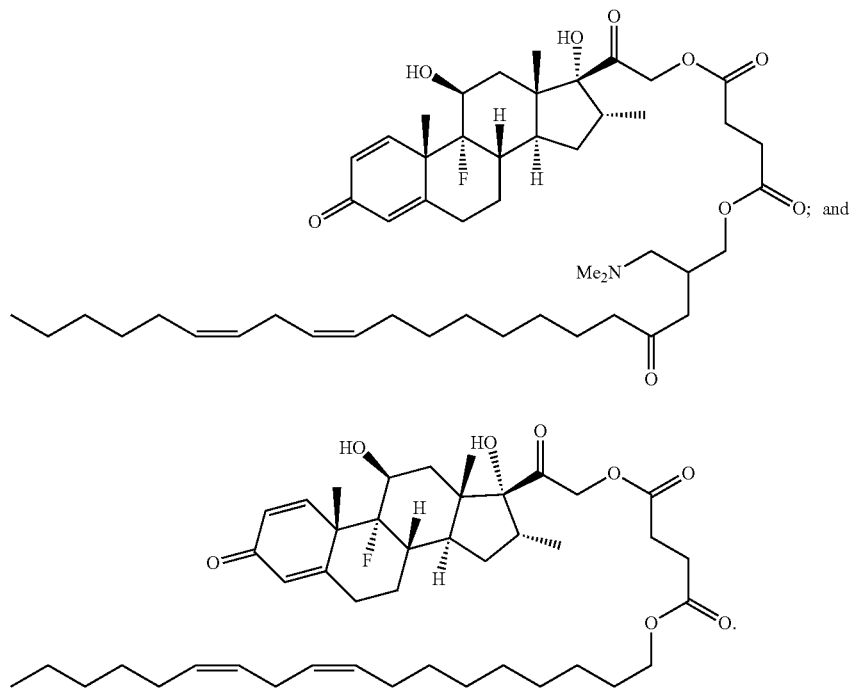

10. A method for suppressing immunity, the method comprising administering a compound of claim 2 to a subject in need thereof.

11. A method for suppressing immunity, the method comprising administering a compound of claim 3 to a subject in need thereof.

12. A method for suppressing immunity, the method comprising administering a compound of claim 4 to a subject in need thereof.

13. A pharmaceutical composition, the pharmaceutical composition comprising a compound of claim 8 and a pharmaceutically acceptable carrier.

14. A pharmaceutical composition, the pharmaceutical composition comprising a compound of claim 2 and a pharmaceutically acceptable carrier.

15. A pharmaceutical composition, the pharmaceutical composition comprising a compound of claim 3 and a pharmaceutically acceptable carrier.

16. A pharmaceutical composition, the pharmaceutical composition comprising a compound of claim 4 and a pharmaceutically acceptable carrier.

\* \* \* \* \*